(12) United States Patent
Spergel et al.

(10) Patent No.: US 10,836,770 B2
(45) Date of Patent: Nov. 17, 2020

(54) IMIDAZOPYRIDAZINE COMPOUNDS USEFUL AS MODULATORS OF IL-12, IL-23 AND/OR INF ALPHA RESPONSES

(71) Applicant: BRISTOL-MYERS SQUIBB COMPANY, Princeton, NJ (US)

(72) Inventors: Steven H. Spergel, Warrington, PA (US); Michael E. Mertzman, New Hope, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/339,744

(22) PCT Filed: Oct. 2, 2017

(86) PCT No.: PCT/US2017/054710
§ 371 (c)(1),
(2) Date: Apr. 5, 2019

(87) PCT Pub. No.: WO2018/067432
PCT Pub. Date: Apr. 12, 2018

(65) Prior Publication Data
US 2019/0225620 A1 Jul. 25, 2019

Related U.S. Application Data

(60) Provisional application No. 62/405,309, filed on Oct. 7, 2016.

(51) Int. Cl.
C07D 487/04 (2006.01)
A61P 37/04 (2006.01)
A61P 29/00 (2006.01)

(52) U.S. Cl.
CPC ............ *C07D 487/04* (2013.01); *A61P 29/00* (2018.01); *A61P 37/04* (2018.01)

(58) Field of Classification Search
CPC ........ C07D 487/04; A61P 29/00; A61P 37/04; A61K 31/5025
See application file for complete search history.

(56) References Cited

FOREIGN PATENT DOCUMENTS

| WO | WO2009100375 A1 | 8/2009 |
| WO | WO2015089143 A1 | 6/2015 |
| WO | WO2017087590 A1 | 5/2017 |

OTHER PUBLICATIONS

Sun. Cytokine, 2015, 75(2), 249-255 (Year: 2015).*
Beck. Nature Reviews: Immunology, 2010, 10, 345-52 (Year: 2010).*
Moslin.Medicinal Chemistry Communications, 2017, 8, 710-712 (Year: 2017).*
U.S. Appl. No. 15/102,991, filed Jun. 9, 2016, Granted (U.S. Pat. No. 10,273,237).
PCT/US2014/069476, filed Dec. 10, 2014 Published (WO2015/089143).
U.S. Appl. No. 16/461,479, filed May 16, 2019, Filed.
PCT/US2017/061895, filed Nov. 16, 2017, Published (WO2018/093968).
U.S. Appl. No. 15/776,094, filed May 15, 2018, Filed.
PCT/US2016/062396, filed Nov. 17, 2016, Published (WO2017/087590).

* cited by examiner

*Primary Examiner* — Noble E Jarrell
(74) *Attorney, Agent, or Firm* — Elliott Korsen

(57) ABSTRACT

Compounds of formula I or a stereoisomer or pharmaceutically-acceptable salt thereof, are useful in the modulation of IL-12, IL-23 and/or IFNa, by acting on Tyk-2 to cause signal transduction inhibition. The compounds of formula I are useful for the treatment of inflammatory or autoimmune diseases.

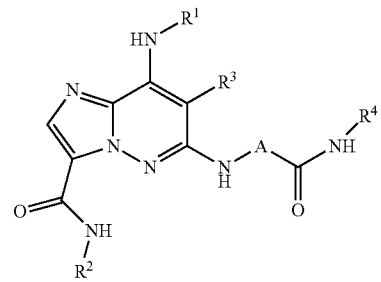

16 Claims, No Drawings
Specification includes a Sequence Listing.

SEQUENCE LISTING

<160> NUMBER OF SEQ ID NOS: 1

<210> SEQ ID NO 1
<211> LENGTH: 317
<212> TYPE: PRT
<213> ORGANISM: Homo sapiens

<400> SEQUENCE: 1

Met Gly Ser Ser His His His His His His Ser Ser Gly Glu Thr Val

-continued

```
1               5                    10                   15

Arg Phe Gln Gly His Met Asn Leu Ser Gln Leu Ser Phe His Arg Val
                20                  25                  30

Asp Gln Lys Glu Ile Thr Gln Leu Ser His Leu Gly Gln Gly Thr Arg
                35                  40                  45

Thr Asn Val Tyr Glu Gly Arg Leu Arg Val Glu Gly Ser Gly Asp Pro
                50                  55                  60

Glu Glu Gly Lys Met Asp Asp Glu Asp Pro Leu Val Pro Gly Arg Asp
65                  70                  75                  80

Arg Gly Gln Glu Leu Arg Val Val Leu Lys Val Leu Asp Pro Ser His
                85                  90                  95

His Asp Ile Ala Leu Ala Phe Tyr Glu Thr Ala Ser Leu Met Ser Gln
                100                 105                 110

Val Ser His Thr His Leu Ala Phe Val His Gly Val Cys Val Arg Gly
                115                 120                 125

Pro Glu Asn Ile Met Val Thr Glu Tyr Val Glu His Gly Pro Leu Asp
                130                 135                 140

Val Trp Leu Arg Arg Glu Arg Gly His Val Pro Met Ala Trp Lys Met
145                 150                 155                 160

Val Val Ala Gln Gln Leu Ala Ser Ala Leu Ser Tyr Leu Glu Asn Lys
                165                 170                 175

Asn Leu Val His Gly Asn Val Cys Gly Arg Asn Ile Leu Leu Ala Arg
                180                 185                 190

Leu Gly Leu Ala Glu Gly Thr Ser Pro Phe Ile Lys Leu Ser Asp Pro
                195                 200                 205

Gly Val Gly Leu Gly Ala Leu Ser Arg Glu Glu Arg Val Glu Arg Ile
                210                 215                 220

Pro Trp Leu Ala Pro Glu Cys Leu Pro Gly Gly Ala Asn Ser Leu Ser
225                 230                 235                 240

Thr Ala Met Asp Lys Trp Gly Phe Gly Ala Thr Leu Leu Glu Ile Cys
                245                 250                 255

Phe Asp Gly Glu Ala Pro Leu Gln Ser Arg Ser Pro Ser Glu Lys Glu
                260                 265                 270

His Phe Tyr Gln Arg Gln His Arg Leu Pro Glu Pro Ser Cys Pro Gln
                275                 280                 285

Leu Ala Thr Leu Thr Ser Gln Cys Leu Thr Tyr Glu Pro Thr Gln Arg
                290                 295                 300

Pro Ser Phe Arg Thr Ile Leu Arg Asp Leu Thr Arg Leu
305                 310                 315
```

IMIDAZOPYRIDAZINE COMPOUNDS USEFUL AS MODULATORS OF IL-12, IL-23 AND/OR INF ALPHA RESPONSES

CROSS-REFERENCE TO RELATED APPLICATIONS

This application claims the benefit of U.S. Provisional Application No. 62/405,309 filed Oct. 7, 2016, the disclosure of which is incorporated herein by reference in its entirety.

FIELD OF THE INVENTION

This invention relates to compounds useful in the modulation of IL-12, IL-23 and/or IFNα by acting on Tyk-2 to cause signal transduction inhibition. Provided herein are imidazopyradazine compounds, compositions comprising such compounds, and methods of their use. The invention further pertains to pharmaceutical compositions containing at least one compound according to the invention that are useful for the treatment of conditions related to the modulation of IL-12, IL-23 and/or IFNα in a mammal.

BACKGROUND OF THE INVENTION

The heterodimeric cytokines interleukin IL-12 and IL-23, which share a common p40 subunit, are produced by activated antigen-presenting cells and are critical in the differentiation and proliferation of Th1 and Th17 cells, two effector T cell lineages which play key roles in autoimmunity. IL-23 is composed of the p40 subunit along with a unique p19 subunit. IL-23, acting through a heterodimeric receptor composed of IL-23R and IL-12Rβ1, is essential for the survival and expansion of Th17 cells which produce pro-inflammatory cytokines such as IL-17A, IL-17F, IL-6 and TNF-α (McGeachy, M. J. et al., "The link between IL-23 and Th17 cell-mediated immune pathologies", Semin. Immunol., 19:372-376 (2007)). These cytokines are critical in mediating the pathobiology of a number of autoimmune diseases, including rheumatoid arthritis, multiple sclerosis, inflammatory bowel disease, and lupus. IL-12, in addition to the p40 subunit in common with IL-23, contains a p35 subunit and acts through a heterodimeric receptor composed of IL-12Rβ1 and IL-12Rβ2. IL-12 is essential for Th1 cell development and secretion of IFNγ, a cytokine which plays a critical role in immunity by stimulating MHC expression, class switching of B cells to IgG subclasses, and the activation of macrophages (Gracie, J. A. et al., "Interleukin-12 induces interferon-gamma-dependent switching of IgG alloantibody subclass", Eur. J. Immunol., 26:1217-1221 (1996); Schroder, K. et al., "Interferon-gamma: an overview of signals, mechanisms and functions", J. Leukoc. Biol., 75(2):163-189 (2004)).

The importance of the p40-containing cytokines in autoimmunity is demonstrated by the discovery that mice deficient in either p40, p19, or IL-23R are protected from disease in models of multiple sclerosis, rheumatoid arthritis, inflammatory bowel disease, lupus and psoriasis, among others (Kyttaris, V. C. et al., "Cutting edge: IL-23 receptor deficiency prevents the development of lupus nephritis in C57BL/6-lpr/lpr mice", J Immunol., 184:4605-4609 (2010); Hong, K. et al., "IL-12, independently of IFN-gamma, plays a crucial role in the pathogenesis of a murine psoriasis like skin disorder", J Immunol., 162:7480-7491 (1999); Hue, S. et al., "Interleukin-23 drives innate and T cell-mediated intestinal inflammation", J. Exp. Med., 203:2473-2483 (2006); Cua, D. J. et al., "Interleukin-23 rather than interleukin-12 is the critical cytokine for autoimmune inflammation of the brain", Nature, 421:744-748 (2003); Murphy, C. A. et al., "Divergent pro- and anti-inflammatory roles for IL-23 and IL-12 in joint autoimmune inflammation", J. Exp. Med., 198:1951-1957 (2003)).

In human disease, high expression of p40 and p19 has been measured in psoriatic lesions, and Th17 cells have been identified in active lesions in the brain from MS patients and in the gut mucosa of patients with active Crohn's disease (Lee, E. et al., "Increased expression of interleukin 23 p19 and p40 in lesional skin of patients with psoriasis vulgaris", J. Exp. Med., 199:125-130 (2004); Tzartos, J. S. et al., "Interleukin-17 production in central nervous system infiltrating T cells and glial cells is associated with active disease in multiple sclerosis", Am. J. Pathol., 172:146-155 (2008)). The mRNA levels of p19, p40, and p35 in active SLE patients were also shown to be significantly higher compared with those in inactive SLE patients (Huang, X. et al., "Dysregulated expression of interleukin-23 and interleukin-12 subunits in systemic lupus erythematosus patients", Mod. Rheumatol., 17:220-223 (2007)), and T cells from lupus patients have a predominant Th1 phenotype (Tucci, M. et al., "Overexpression of interleukin-12 and T helper 1 predominance in lupus nephritis", Clin. Exp. Immunol., 154:247-254 (2008)).

Moreover, genome-wide association studies have identified a number of loci associated with chronic inflammatory and autoimmune diseases that encode factors that function in the IL-23 and IL-12 pathways. These genes include IL23A, IL12A, IL12B, IL12RB1, IL12RB2, IL23R, JAK2, TYK2, STAT3, and STAT4 (Lees, C. W. et al., "New IBD genetics: common pathways with other diseases", Gut, 60:1739-1753 (2011); Tao, J. H. et al., "Meta-analysis of TYK2 gene polymorphisms association with susceptibility to autoimmune and inflammatory diseases", Mol. Biol. Rep., 38:4663-4672 (2011); Cho, J. H. et al., "Recent insights into the genetics of inflammatory bowel disease", Gastroenterology, 140:1704-1712 (2011)).

Indeed, anti-p40 treatment, which inhibits both IL-12 and IL-23, as well as IL-23-specific anti-p19 therapies have been shown to be efficacious in the treatment of autoimmunity in diseases including psoriasis, Crohn's Disease and psoriatic arthritis (Leonardi, C. L. et al., "PHOENIX 1 study investigators. Efficacy and safety of ustekinumab, a human interleukin-12/23 monoclonal antibody, in patients with psoriasis: 76-week results from a randomized, double-blind, placebo-controlled trial (PHOENIX 1)", Lancet, 371:1665-1674 (2008); Sandborn, W. J. et al., "Ustekinumab Crohn's Disease Study Group. A randomized trial of Ustekinumab, a human interleukin-12/23 monoclonal antibody, in patients with moderate-to-severe Crohn's disease", Gastroenterology, 135:1130-1141 (2008); Gottlieb, A. et al., "Ustekinumab, a human interleukin 12/23 monoclonal antibody, for psoriatic arthritis: randomized, double-blind, placebo-controlled, crossover trial", Lancet, 373:633-640 (2009)). Therefore, agents which inhibit the action of IL-12 and IL-23 may be expected to have therapeutic benefit in human autoimmune disorders.

The Type I group of interferons (IFNs), which include the IFNα members as well as IFNβ, IFNε, IFNκ and IFNω, act through a heterodimer IFNα/β receptor (IFNAR). Type I IFNs have multiple effects in both the innate and adaptive immune systems including activation of both the cellular and humoral immune responses as well as enhancing the expression and release of autoantigens (Hall, J. C. et al., "Type I interferons: crucial participants in disease amplification in autoimmunity", *Nat. Rev. Rheumatol.,* 6:40-49 (2010)).

In patients with systemic lupus erythematosus (SLE), a potentially fatal autoimmune disease, increased serum levels of interferon (IFN)-α (a type I interferon) or increased expression of type I IFN-regulated genes (a so-called IFNα signature) in peripheral blood mononuclear cells and in affected organs has been demonstrated in a majority of patients (Bennett, L. et al., "Interferon and granulopoiesis signatures in systemic lupus erythematosus blood", *J. Exp. Med.,* 197:711-723 (2003); Peterson, K. S. et al., "Characterization of heterogeneity in the molecular pathogenesis of lupus nephritis from transcriptional profiles of laser-captured glomeruli", *J. Clin. Invest.,* 113:1722-1733 (2004)), and several studies have shown that serum IFNα levels correlate with both disease activity and severity (Bengtsson, A. A. et al., "Activation of type I interferon system in systemic lupus erythematosus correlates with disease activity but not with antiretroviral antibodies", *Lupus,* 9:664-671 (2000)). A direct role for IFNα in the pathobiology of lupus is evidenced by the observation that the administration of IFNα to patients with malignant or viral diseases can induce a lupus-like syndrome. Moreover, the deletion of the IFNAR in lupus-prone mice provides high protection from autoimmunity, disease severity and mortality (Santiago-Raber, M. L. et al., "Type-I interferon receptor deficiency reduces lupus-like disease in NZB mice", *J. Exp. Med.,* 197:777-788 (2003)), and genome-wide association studies have identified loci associated with lupus that encode factors that function in the type I interferon pathway, including IRF5, IKBKE, TYK2, and STAT4 (Deng, Y. et al., "Genetic susceptibility to systemic lupus erythematosus in the genomic era", *Nat. Rev. Rheumatol.,* 6:683-692 (2010); Sandling, J. K. et al., "A candidate gene study of the type I interferon pathway implicates IKBKE and IL8 as risk loci for SLE", *Eur. J. Hum. Genet.,* 19:479-484 (2011)). In addition to lupus, there is evidence that aberrant activation of type I interferon-mediated pathways are important in the pathobiology of other autoimmune diseases such as Sjögren's syndrome and scleroderma (Bave, U. et al., "Activation of the type I interferon system in primary Sjögren's syndrome: a possible etiopathogenic mechanism", *Arthritis Rheum.,* 52:1185-1195 (2005); Kim, D. et al., "Induction of interferon-alpha by scleroderma sera containing autoantibodies to topoisomerase I: association of higher interferon-alpha activity with lung fibrosis", *Arthritis Rheum.,* 58:2163-2173 (2008)). Therefore, agents which inhibit the action of type I interferon responses may be expected to have therapeutic benefit in human autoimmune disorders.

Tyrosine kinase 2 (Tyk2) is a member of the Janus kinase (JAK) family of nonreceptor tyrosine kinases and has been shown to be critical in regulating the signal transduction cascade downstream of receptors for IL-12, IL-23 and type I interferons in both mice (Ishizaki, M. et al., "Involvement of Tyrosine Kinase-2 in Both the IL-12/Th1 and IL-23/Th17 Axes In Vivo" *J. Immunol.,* 187:181-189 (2011); Prchal-Murphy, M. et al., "TYK2 kinase activity is required for functional type I interferon responses in vivo" *PLoS One,* 7:e39141 (2012)) and humans (Minegishi, Y. et al., "Human tyrosine kinase 2 deficiency reveals its requisite roles in multiple cytokine signals involved in innate and acquired immunity" *Immunity,* 25:745-755 (2006)). Tyk2 mediates the receptor-induced phosphorylation of members of the STAT family of transcription factors, an essential signal that leads to the dimerization of STAT proteins and the transcription of STAT-dependent pro-inflammatory genes. Tyk2-deficient mice are resistant to experimental models of colitis, psoriasis and multiple sclerosis, demonstrating the importance of Tyk2-mediated signaling in autoimmunity and related disorders (Ishizaki, M. et al., "Involvement of Tyrosine Kinase-2 in Both the IL-12/Th1 and IL-23/Th17 Axes In Vivo" *J. Immunol.,* 187:181-189 (2011); Oyamada, A. et al., "Tyrosine kinase 2 plays critical roles in the pathogenic CD4 T cell responses for the development of experimental autoimmune encephalomyelitis" *J. Immunol.* 183:7539-7546 (2009)).

In humans, individuals expressing an inactive variant of Tyk2 are protected from multiple sclerosis and possibly other autoimmune disorders (Couturier, N. et al., "Tyrosine kinase 2 variant influences T lymphocyte polarization and multiple sclerosis susceptibility" *Brain* 134:693-703 (2011)). Genome-wide association studies have shown other variants of Tyk2 to be associated with autoimmune disorders such as Crohn's Disease, psoriasis, systemic lupus erythematosus, and rheumatoid arthritis, further demonstrating the importance of Tyk2 in autoimmunity (Ellinghaus, D. et al., "Combined Analysis of Genome-wide Association Studies for Crohn Disease and Psoriasis Identifies Seven Shared Susceptibility Loci" *Am. J. Hum. Genet.* 90:636-647 (2012); Graham, D. et al. "Association of polymorphisms across the tyrosine kinase gene, TYK2 in UK SLE families" *Rheumatology (Oxford)* 46:927-930 (2007); Eyre, S. et al. "High-density genetic mapping identifies new susceptibility loci for rheumatoid arthritis" *Nat. Genet.* 44:1336-1340 (2012)).

In view of the conditions that may benefit by treatment involving the modulation of cytokines and/or interferons, new compounds capable of modulating cytokines and/or interferons, such as IL-12, IL-23 and/or IFNα, and methods of using these compounds may provide substantial therapeutic benefits to a wide variety of patients in need thereof.

SUMMARY OF THE INVENTION

The invention is directed to compounds of Formula I, infra, that which are useful as modulators of IL-12, IL-23 and/or IFNα by inhibiting Tyk2-mediated signal transduction.

The present invention also provides processes and intermediates for making the compounds of the present invention.

The present invention also provides pharmaceutical compositions comprising a pharmaceutically acceptable carrier and at least one of the compounds of the present invention.

The present invention also provides a method for the modulation of IL-12, IL-23 and/or IFNα by inhibiting Tyk-2-mediated signal transduction comprising administering to a host in need of such treatment a therapeutically effective amount of at least one of the compounds of the present invention.

The present invention also provides a method for treating proliferative, metabolic, allergic, autoimmune and inflammatory diseases, comprising administering to a host in need of such treatment a therapeutically effective amount of at least one of the compounds of the present invention.

A preferred embodiment is a method for treating inflammatory and autoimmune diseases or diseases. For the purposes of this invention, an inflammatory and autoimmune disease or disorder includes any disease having an inflammatory or autoimmune component.

A preferred embodiment is a method for treating inflammatory and autoimmune diseases or diseases wherein the disease is multiple sclerosis, rheumatoid arthritis, inflammatory bowel disease, systemic lupus erythematosus, psoriasis, psoriatic arthritis, Crohn's Disease, Sjögren's syndrome or scleroderma.

An alternate preferred embodiment is a method for treating metabolic diseases, including type 2 diabetes and atherosclerosis.

The present invention also provides the use of the compounds of the present invention for the manufacture of a medicament for the treatment of cancers.

The present invention also provides the compounds of the present invention for use in therapy.

These and other features of the invention will be set forth in the expanded form as the disclosure continues.

DETAILED DESCRIPTION OF THE EMBODIMENTS OF THE INVENTION

In a first aspect of the present invention, there is provided a compound of formula (I)

wherein

A is a 5 membered heteroaryl group containing 1-2 heteroatoms independently selected from —N—, —O— or —S— substituted with 0-2 $R^x$;

$R^x$ is H or $C_1$-$C_6$ alkyl;

$R^1$ is H, $C_1$-$C_6$ alkyl, $C_3$-$C_8$ cycloalkyl, hydroxy $C_1$-$C_6$ alkyl or alkoxy $C_1$-$C_6$ alkyl;

$R^2$ is H, $C_1$-$C_6$ alkyl, $C_3$-$C_8$ cycloalkyl, hydroxy $C_1$-$C_6$ alkyl, alkoxy $C_1$-$C_6$ alkyl, $C_3$-$C_8$ cycloalkyl $C_1$-$C_6$ alkyl-, di ($C_1$-$C_4$) alkyl aminoalkyl-, aryl, heteroaryl, or heterocyclyl $C_1$-$C_6$ alkyl-, substituted with 0-2 $R^{2a}$;

$R^{2a}$ is halo or $C_1$-$C_6$ alkyl;

$R^3$ is H, $C_1$-$C_6$ alkyl, $C_3$-$C_8$ cycloalkyl, hydroxy $C_1$-$C_6$ alkyl or alkoxy $C_1$-$C_6$ alkyl;

$R^4$ is H, $CD_3$, $C_1$-$C_6$ alkyl, alkoxy $C_1$-$C_6$ alkyl, 3- to 10-membered mono or bicyclic cycloalkyl, 4- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-2 $R^{4a}$;

$R^{4a}$ is H, $NR^5R^6$, $C_1$-$C_6$ alkyl, $C_3$-$C_8$ cycloalkyl, hydroxy $C_1$-$C_6$ alkyl or alkoxy $C_1$-$C_6$ alkyl;

$R^5$ and $R^6$ are independently H or $C_1$-$C_4$ alkyl; or $R^5$ and $R^6$ are taken together with the nitrogen atom to which they are attached to form a 3-10 membered heterocyclyl ring substituted with 0-2 substituents selected from H, $C_1$-$C_4$ alkyl and OH;

or a pharmaceutically acceptable salt, tautomer or stereoisomer thereof.

In a second embodiment, there is provided a compound of the formula wherein
A is $R^x$ is H or $C_1$-$C_6$ alkyl;

$R^1$ is H, $C_1$-$C_6$ alkyl, $C_3$-$C_8$ cycloalkyl, hydroxy $C_1$-$C_6$ alkyl or alkoxy $C_1$-$C_6$ alkyl;

$R^2$ is H, $C_1$-$C_6$ alkyl, $C_3$-$C_8$ cycloalkyl, hydroxy $C_1$-$C_6$ alkyl, alkoxy $C_1$-$C_6$ alkyl, $C_3$-$C_8$ cycloalkyl $C_1$-$C_6$ alkyl-, di ($C_1$-$C_4$) alkyl aminoalkyl-, aryl, heteroaryl, or heterocyclyl $C_1$-$C_6$ alkyl-, substituted with 0-2 $R^{2a}$;

$R^{2a}$ is halo or $C_1$-$C_6$ alkyl;

$R^3$ is H, $C_1$-$C_6$ alkyl, $C_3$-$C_8$ cycloalkyl, hydroxy $C_1$-$C_6$ alkyl or alkoxy $C_1$-$C_6$ alkyl;

$R^4$ is H, $CD_3$, $C_1$-$C_6$ alkyl, alkoxy $C_1$-$C_6$ alkyl, 3- to 10-membered mono or bicyclic cycloalkyl, 4- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-2 $R^{4a}$;

$R^{4a}$ is H, $NR^5R^6$, $C_1$-$C_6$ alkyl, $C_3$-$C_8$ cycloalkyl, hydroxy $C_1$-$C_6$ alkyl or alkoxy $C_1$-$C_6$ alkyl $R^5$ and $R^6$ are independently H or $C_1$-$C_4$ alkyl; or $R^5$ and $R^6$ are taken together with the nitrogen atom to which they are attached to form a 3-10 membered heterocyclyl ring substituted with 0-2 substituents selected from H, $C_1$-$C_4$ alkyl and OH;

or a pharmaceutically acceptable salt, tautomer or stereoisomer thereof.

In a third embodiment, there is provided a compound of the formula

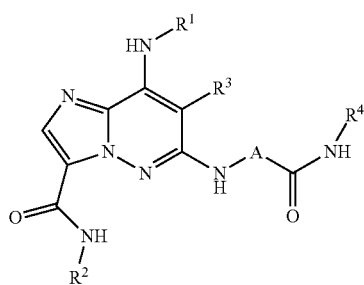
(I)

wherein
A is

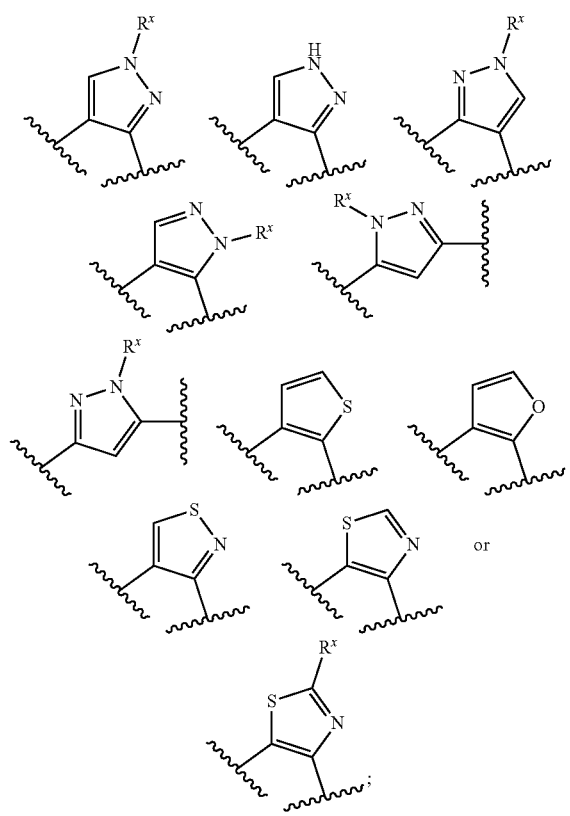

$R^x$ is $C_1$-$C_3$ alkyl;

$R^1$ is H, $C_1$-$C_6$ alkyl, $C_3$-$C_8$ cycloalkyl, hydroxy $C_1$-$C_6$ alkyl or alkoxy $C_1$-$C_6$ alkyl;

$R^2$ is H, $C_1$-$C_6$ alkyl, $C_3$-$C_8$ cycloalkyl, hydroxy $C_1$-$C_6$ alkyl, alkoxy $C_1$-$C_6$ alkyl, $C_3$-$C_8$ cycloalkyl $C_1$-$C_6$ alkyl-, di($C_1$-$C_4$) alkyl aminoalkyl-, aryl, heteroaryl, or heterocyclyl $C_1$-$C_6$ alkyl-, substituted with 0-2 $R^{2a}$;

$R^{2a}$ is halo or $C_1$-$C_6$ alkyl;

$R^3$ is H, $C_1$-$C_6$ alkyl, $C_3$-$C_8$ cycloalkyl, hydroxy $C_1$-$C_6$ alkyl or alkoxy $C_1$-$C_6$ alkyl;

$R^4$ is H, $CD_3$, $C_1$-$C_6$ alkyl, alkoxy $C_1$-$C_6$ alkyl, 3- to 10-membered mono or bicyclic cycloalkyl, 4- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-2 $R^{4a}$;

$R^{4a}$ is H, $NR^5R^6$, $C_1$-$C_6$ alkyl, $C_3$-$C_8$ cycloalkyl, hydroxy $C_1$-$C_6$ alkyl or alkoxy $C_1$-$C_6$ alkyl;

$R^5$ and $R^6$ are independently H or $C_1$-$C_4$ alkyl; or $R^5$ and $R^6$ are taken together with the nitrogen atom to which they are attached to form a 3-10 membered heterocyclyl ring substituted with 0-2 substituents selected from H, $C_1$-$C_4$ alkyl and OH;

or a pharmaceutically acceptable salt, tautomer or stereoisomer thereof.

In a 4th embodiment, there is provided a compound of formula II,

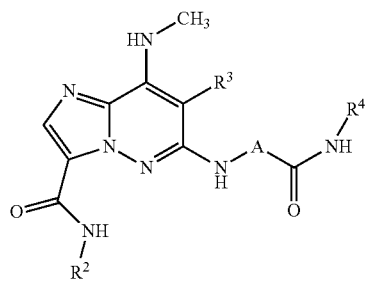
(II)

wherein
A is

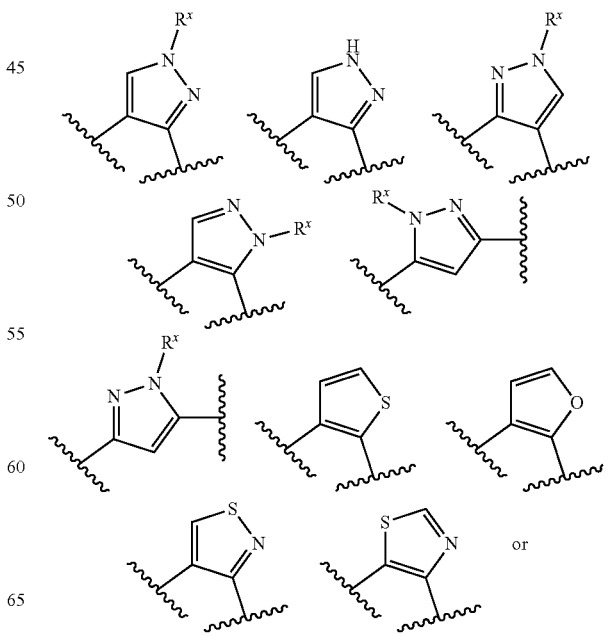

-continued

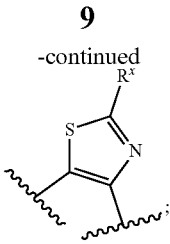

$R^x$ is $C_1$-$C_3$ alkyl;

$R^2$ is H, $C_1$-$C_6$ alkyl, $C_3$-$C_8$ cycloalkyl, hydroxy $C_1$-$C_6$ alkyl, alkoxy $C_1$-$C_6$ alkyl, $C_3$-$C_8$ cycloalkyl $C_1$-$C_6$ alkyl-, di ($C_1$-$C_4$) alkyl aminoalkyl-, aryl, heteroaryl, or heterocyclyl $C_1$-$C_6$ alkyl-, substituted with 0-2 $R^{2a}$;

$R^{2a}$ is halo or $C_1$-$C_6$ alkyl;

$R^3$ is H, $C_1$-$C_6$ alkyl, $C_3$-$C_8$ cycloalkyl, hydroxy $C_1$-$C_6$ alkyl or alkoxy $C_1$-$C_6$ alkyl;

$R^4$ is H, $CD_3$, $C_1$-$C_6$ alkyl, alkoxy $C_1$-$C_6$ alkyl, 3- to 10-membered mono or bicyclic cycloalkyl, 4- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-2 $R^{4a}$;

$R^{4a}$ is H, $NR^5R^6$, $C_1$-$C_6$ alkyl, $C_3$-$C_8$ cycloalkyl, hydroxy $C_1$-$C_6$ alkyl or alkoxy $C_1$-$C_6$ alkyl;

$R^5$ and $R^6$ are independently H or $C_1$-$C_4$ alkyl; or $R^5$ and $R^6$ are taken together with the nitrogen atom to which they are attached to form a 3-10 membered heterocyclyl ring substituted with 0-2 substituents selected from H, $C_1$-$C_4$ alkyl and OH;

or a pharmaceutically acceptable salt, tautomer or stereoisomer thereof.

In a 5th embodiment, there is provided a compound of formula II

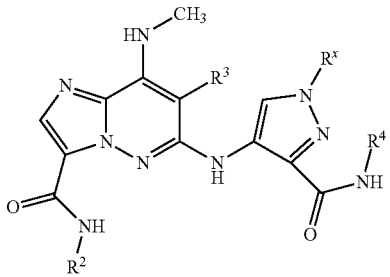

(II)

wherein $R^x$ is $C_1$-$C_3$ alkyl;

$R^2$ is H, $C_1$-$C_6$ alkyl, $C_3$-$C_8$ cycloalkyl, hydroxy $C_1$-$C_6$ alkyl, alkoxy $C_1$-$C_6$ alkyl, $C_3$-$C_8$ cycloalkyl $C_1$-$C_6$ alkyl-, di ($C_1$-$C_4$) alkyl aminoalkyl-, aryl, heteroaryl, or heterocyclyl $C_1$-$C_6$ alkyl-, substituted with 0-2 $R^{2a}$;

$R^{2a}$ is halo or $C_1$-$C_6$ alkyl;

$R^3$ is H, $C_1$-$C_6$ alkyl, $C_3$-$C_8$ cycloalkyl, hydroxy $C_1$-$C_6$ alkyl or alkoxy $C_1$-$C_6$ alkyl;

$R^4$ is H, $CD_3$, $C_1$-$C_6$ alkyl, alkoxy $C_1$-$C_6$ alkyl, 3- to 10-membered mono or bicyclic cycloalkyl, 4- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-2 $R^{4a}$;

$R^{4a}$ is H, $NR^5R^6$, $C_1$-$C_6$ alkyl, $C_3$-$C_8$ cycloalkyl, hydroxy $C_1$-$C_6$ alkyl or alkoxy $C_1$-$C_6$ alkyl;

$R^5$ and $R^6$ are independently H or $C_1$-$C_4$ alkyl; or $R^5$ and $R^6$ are taken together with the nitrogen atom to which they are attached to form a 3-10 membered heterocyclyl ring substituted with 0-2 substituents selected from H, $C_1$-$C_4$ alkyl and OH;

or a pharmaceutically acceptable salt, tautomer or stereoisomer thereof.

In another embodiment, there is provided a compound of the formula,

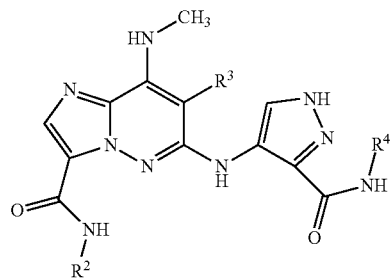

wherein $R^2$ is H, $C_1$-$C_6$ alkyl, $C_3$-$C_8$ cycloalkyl, hydroxy $C_1$-$C_6$ alkyl, alkoxy $C_1$-$C_6$ alkyl, $C_3$-$C_8$ cycloalkyl $C_1$-$C_6$ alkyl-, di ($C_1$-$C_4$) alkyl aminoalkyl-, aryl, heteroaryl, or heterocyclyl $C_1$-$C_6$ alkyl-, substituted with 0-2 $R^{2a}$;

$R^{2a}$ is halo or $C_1$-$C_6$ alkyl;

$R^3$ is H, $C_1$-$C_6$ alkyl, $C_3$-$C_8$ cycloalkyl, hydroxy $C_1$-$C_6$ alkyl or alkoxy $C_1$-$C_6$ alkyl;

$R^4$ is H, $CD_3$, $C_1$-$C_6$ alkyl, alkoxy $C_1$-$C_6$ alkyl, 3- to 10-membered mono or bicyclic cycloalkyl, 4- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-2 $R^{4a}$;

$R^{4a}$ is H, $NR^5R^6$, $C_1$-$C_6$ alkyl, $C_3$-$C_8$ cycloalkyl, hydroxy $C_1$-$C_6$ alkyl or alkoxy $C_1$-$C_6$ alkyl;

$R^5$ and $R^6$ are independently H or $C_1$-$C_4$ alkyl; or $R^5$ and $R^6$ are taken together with the nitrogen atom to which they are attached to form a 3-10 membered heterocyclyl ring substituted with 0-2 substituents selected from H, $C_1$-$C_4$ alkyl and OH;

or a pharmaceutically acceptable salt, tautomer or stereoisomer thereof.

In another preferred embodiment, there is provided a compound of the formula,

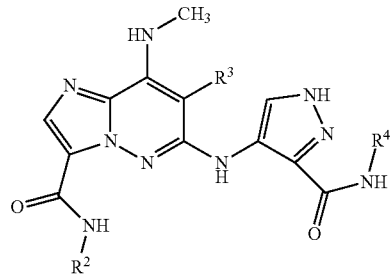

wherein
R² is H, C₁-C₆ alkyl, C₃-C₈ cycloalkyl, hydroxy C₁-C₆ alkyl, alkoxy C₁-C₆ alkyl, C₃-C₈ cycloalkyl C₁-C₆ alkyl-, di (C₁-C₄) alkyl aminoalkyl-, aryl, heteroaryl, or heterocyclyl C₁-C₆ alkyl-, substituted with 0-2 R²ᵃ;

R²ᵃ is halo or C₁-C₆ alkyl;

R³ is H, C₁-C₆ alkyl, C₃-C₈ cycloalkyl, hydroxy C₁-C₆ alkyl or alkoxy C₁-C₆ alkyl;

R⁴ is H, CD₃, C₁-C₆ alkyl, alkoxy C₁-C₆ alkyl, 3- to 10-membered mono or bicyclic cycloalkyl, 4- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-2 R⁴ᵃ;

R⁴ᵃ is H, NR⁵R⁶, C₁-C₆ alkyl, C₃-C₈ cycloalkyl, hydroxy C₁-C₆ alkyl or alkoxy C₁-C₆ alkyl;

R⁵ and R⁶ are independently H or C₁-C₄ alkyl; or

R⁵ and R⁶ are taken together with the nitrogen atom to which they are attached to form a 3-10 membered heterocyclyl ring substituted with 0-2 substituents selected from H, C₁-C₄ alkyl and OH;

or a pharmaceutically acceptable salt, tautomer or stereoisomer thereof.

In another preferred embodiment, there is provided a compound of the formula,

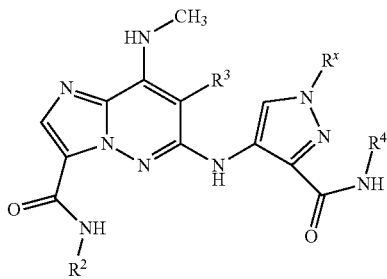

wherein
Rˣ is C₁-C₃ alkyl;

R² is H, C₁-C₆ alkyl, C₃-C₈ cycloalkyl, hydroxy C₁-C₆ alkyl, alkoxy C₁-C₆ alkyl, C₃-C₈ cycloalkyl C₁-C₆ alkyl-, di (C₁-C₄) alkyl aminoalkyl-, aryl, heteroaryl, or heterocyclyl C₁-C₆ alkyl-, substituted with 0-2 R²ᵃ;

R²ᵃ is halo or C₁-C₆ alkyl;

R³ is H, C₁-C₆ alkyl, C₃-C₈ cycloalkyl, hydroxy C₁-C₆ alkyl or alkoxy C₁-C₆ alkyl;

R⁴ is H, CD₃, C₁-C₆ alkyl, alkoxy C₁-C₆ alkyl, 3- to 10-membered mono or bicyclic cycloalkyl, 4- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-2 R⁴ᵃ;

R⁴ᵃ is H, NR⁵R⁶, C₁-C₆ alkyl, C₃-C₈ cycloalkyl, hydroxy C₁-C₆ alkyl or alkoxy C₁-C₆ alkyl;

R⁵ and R⁶ are independently H or C₁-C₄ alkyl; or

R⁵ and R⁶ are taken together with the nitrogen atom to which they are attached to form a 3-10 membered heterocyclyl ring substituted with 0-2 substituents selected from H, C₁-C₄ alkyl and OH;

or a pharmaceutically acceptable salt, tautomer or stereoisomer thereof.

In another preferred embodiment, there is provided a compound of the formula,

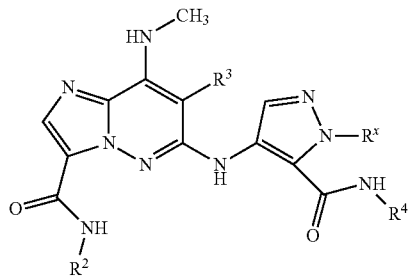

wherein
Rˣ is C₁-C₃ alkyl;

R² is H, C₁-C₆ alkyl, C₃-C₈ cycloalkyl, hydroxy C₁-C₆ alkyl, alkoxy C₁-C₆ alkyl, C₃-C₈ cycloalkyl C₁-C₆ alkyl-, di (C₁-C₄) alkyl aminoalkyl-, aryl, heteroaryl, or heterocyclyl C₁-C₆ alkyl-, substituted with 0-2 R²ᵃ;

R²ᵃ is halo or C₁-C₆ alkyl;

R³ is H, C₁-C₆ alkyl, C₃-C₈ cycloalkyl, hydroxy C₁-C₆ alkyl or alkoxy C₁-C₆ alkyl;

R⁴ is H, CD₃, C₁-C₆ alkyl, alkoxy C₁-C₆ alkyl, 3- to 10-membered mono or bicyclic cycloalkyl, 4- to 10-membered mono or bicyclic aryl, 4- to 10-membered mono or bicyclic heterocyclyl, or substituted 4- to 10-mono or bicy- In another preferred embodiment, there is provided a compound of the formula,

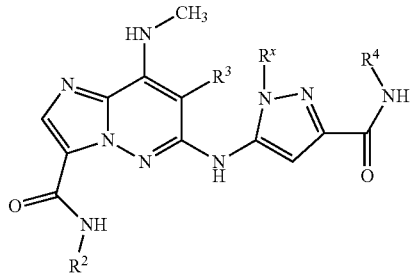

clic heteroaryl, each heterocyclyl or heteroaryl containing 1-3 heteroatoms selected from N, O, and S, any of said groups other than H substituted with 0-2 $R^{4a}$;

$R^{4a}$ is H, $NR^5R^6$, $C_1$-$C_6$ alkyl, $C_3$-$C_8$ cycloalkyl, hydroxy $C_1$-$C_6$ alkyl or alkoxy $C_1$-$C_6$ alkyl;

$R^5$ and $R^6$ are independently H or $C_1$-$C_4$ alkyl; or $R^5$ and $R^6$ are taken together with the nitrogen atom to which they are attached to form a 3-10 membered heterocyclyl ring substituted with 0-2 substituents selected from H, $C_1$-$C_4$ alkyl and OH;

or a pharmaceutically acceptable salt, tautomer or stereoisomer thereof.

In another preferred embodiment, there is provided a compound of the formula,

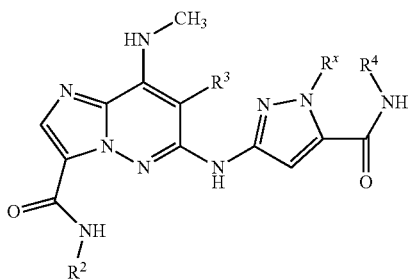

wherein $R^x$ is $C_1$-$C_3$ alkyl;

$R^2$ is H, $C_1$-$C_6$ alkyl, $C_3$-$C_8$ cycloalkyl, hydroxy $C_1$-$C_6$ alkyl, alkoxy $C_1$-$C_6$ alkyl, $C_3$-$C_8$ cycloalkyl $C_1$-$C_6$ alkyl-, di ($C_1$-$C_4$) alkyl aminoalkyl-, aryl, heteroaryl, or heterocyclyl $C_1$-$C_6$ alkyl-, substituted with 0-2 $R^{2a}$;

$R^{2a}$ is halo or $C_1$-$C_6$ alkyl;

$R^3$ is H, $C_1$-$C_6$ alkyl, $C_3$-$C_8$ cycloalkyl, hydroxy $C_1$-$C_6$ alkyl or alkoxy $C_1$-$C_6$ alkyl;

$R^4$ is H, $CD_3$, $C_1$-$C_6$ alkyl, alkoxy $C_1$-$C_6$ alkyl, 3- to 10-membered mono or bicyclic cycloalkyl, 4- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-2 $R^{4a}$;

$R^{4a}$ is H, $NR^5R^6$, $C_1$-$C_6$ alkyl, $C_3$-$C_8$ cycloalkyl, hydroxy $C_1$-$C_6$ alkyl or alkoxy $C_1$-$C_6$ alkyl;

$R^5$ and $R^6$ are independently H or $C_1$-$C_4$ alkyl; or $R^5$ and $R^6$ are taken together with the nitrogen atom to which they are attached to form a 3-10 membered heterocyclyl ring substituted with 0-2 substituents selected from H, $C_1$-$C_4$ alkyl and OH;

or a pharmaceutically acceptable salt, tautomer or stereoisomer thereof.

In another preferred embodiment, there is provided a compound of the formula,

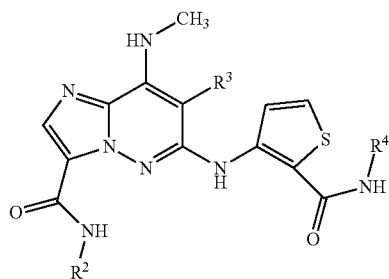

wherein $R^2$ is H, $C_1$-$C_6$ alkyl, $C_3$-$C_8$ cycloalkyl, hydroxy $C_1$-$C_6$ alkyl, alkoxy $C_1$-$C_6$ alkyl, $C_3$-$C_8$ cycloalkyl $C_1$-$C_6$ alkyl-, di ($C_1$-$C_4$) alkyl aminoalkyl-, aryl, heteroaryl, or heterocyclyl $C_1$-$C_6$ alkyl-, substituted with 0-2 $R^{2a}$;

$R^{2a}$ is halo or $C_1$-$C_6$ alkyl;

$R^3$ is H, $C_1$-$C_6$ alkyl, $C_3$-$C_8$ cycloalkyl, hydroxy $C_1$-$C_6$ alkyl or alkoxy $C_1$-$C_6$ alkyl;

$R^4$ is H, $CD_3$, $C_1$-$C_6$ alkyl, alkoxy $C_1$-$C_6$ alkyl, 3- to 10-membered mono or bicyclic cycloalkyl, 4- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-2 $R^{4a}$;

$R^{4a}$ is H, $NR^5R^6$, $C_1$-$C_6$ alkyl, $C_3$-$C_8$ cycloalkyl, hydroxy $C_1$-$C_6$ alkyl or alkoxy $C_1$-$C_6$ alkyl;

$R^5$ and $R^6$ are independently H or $C_1$-$C_4$ alkyl; or $R^5$ and $R^6$ are taken together with the nitrogen atom to which they are attached to form a 3-10 membered heterocyclyl ring substituted with 0-2 substituents selected from H, $C_1$-$C_4$ alkyl and OH;

or a pharmaceutically acceptable salt, tautomer or stereoisomer thereof.

In another preferred embodiment, there is provided a compound of the formula,

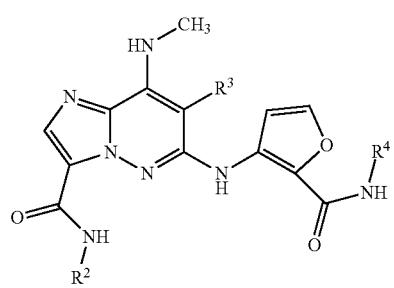

wherein $R^2$ is H, $C_1$-$C_6$ alkyl, $C_3$-$C_8$ cycloalkyl, hydroxy $C_1$-$C_6$ alkyl, alkoxy $C_1$-$C_6$ alkyl, $C_3$-$C_8$ cycloalkyl $C_1$-$C_6$ alkyl-, di ($C_1$-$C_4$) alkyl aminoalkyl-, aryl, heteroaryl, or heterocyclyl $C_1$-$C_6$ alkyl-, substituted with 0-2 $R^{2a}$;

$R^{2a}$ is halo or $C_1$-$C_6$ alkyl;

$R^3$ is H, $C_1$-$C_6$ alkyl, $C_3$-$C_8$ cycloalkyl, hydroxy $C_1$-$C_6$ alkyl or alkoxy $C_1$-$C_6$ alkyl;

$R^4$ is H, $CD_3$, $C_1$-$C_6$ alkyl, alkoxy $C_1$-$C_6$ alkyl, 3- to 10-membered mono or bicyclic cycloalkyl, 4- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-2 $R^{4a}$;

$R^{4a}$ is H, $NR^5R^6$, $C_1$-$C_6$ alkyl, $C_3$-$C_8$ cycloalkyl, hydroxy $C_1$-$C_6$ alkyl or alkoxy $C_1$-$C_6$ alkyl;

$R^5$ and $R^6$ are independently H or $C_1$-$C_4$ alkyl; or $R^5$ and $R^6$ are taken together with the nitrogen atom to which they are attached to form a 3-10 membered heterocyclyl ring substituted with 0-2 substituents selected from H, $C_1$-$C_4$ alkyl and OH;

or a pharmaceutically acceptable salt, tautomer or stereoisomer thereof.

In another preferred embodiment, there is provided a compound of the formula,

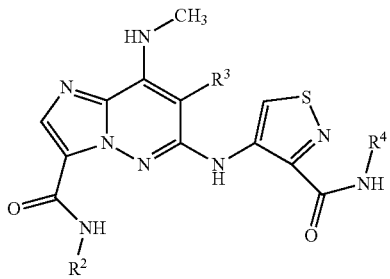

wherein $R^2$ is H, $C_1$-$C_6$ alkyl, $C_3$-$C_8$ cycloalkyl, hydroxy $C_1$-$C_6$ alkyl, alkoxy $C_1$-$C_6$ alkyl, $C_3$-$C_8$ cycloalkyl $C_1$-$C_6$ alkyl-, di ($C_1$-$C_4$) alkyl aminoalkyl-, aryl, heteroaryl, or heterocyclyl $C_1$-$C_6$ alkyl-, substituted with 0-2 $R^{2a}$;

$R^{2a}$ is halo or $C_1$-$C_6$ alkyl;

$R^3$ is H, $C_1$-$C_6$ alkyl, $C_3$-$C_8$ cycloalkyl, hydroxy $C_1$-$C_6$ alkyl or alkoxy $C_1$-$C_6$ alkyl;

$R^4$ is H, $CD_3$, $C_1$-$C_6$ alkyl, alkoxy $C_1$-$C_6$ alkyl, 3- to 10-membered mono or bicyclic cycloalkyl, 4- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-2 $R^{4a}$;

$R^{4a}$ is H, $NR^5R^6$, $C_1$-$C_6$ alkyl, $C_3$-$C_8$ cycloalkyl, hydroxy $C_1$-$C_6$ alkyl or alkoxy $C_1$-$C_6$ alkyl;

$R^5$ and $R^6$ are independently H or $C_1$-$C_4$ alkyl; or $R^5$ and $R^6$ are taken together with the nitrogen atom to which they are attached to form a 3-10 membered heterocyclyl ring substituted with 0-2 substituents selected from H, $C_1$-$C_4$ alkyl and OH;

or a pharmaceutically acceptable salt, tautomer or stereoisomer thereof.

In another preferred embodiment, there is provided a compound of the formula,

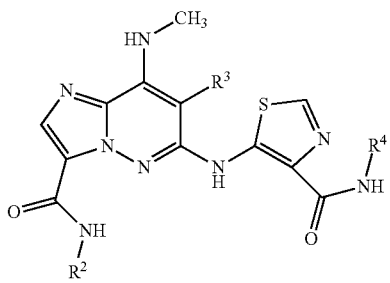

wherein $R^2$ is H, $C_1$-$C_6$ alkyl, $C_3$-$C_8$ cycloalkyl, hydroxy $C_1$-$C_6$ alkyl, alkoxy $C_1$-$C_6$ alkyl, $C_3$-$C_8$ cycloalkyl $C_1$-$C_6$ alkyl-, di ($C_1$-$C_4$) alkyl aminoalkyl-, aryl, heteroaryl, or heterocyclyl $C_1$-$C_6$ alkyl-, substituted with 0-2 $R^{2a}$;

$R^{2a}$ is halo or $C_1$-$C_6$ alkyl;

$R^3$ is H, $C_1$-$C_6$ alkyl, $C_3$-$C_8$ cycloalkyl, hydroxy $C_1$-$C_6$ alkyl or alkoxy $C_1$-$C_6$ alkyl;

$R^4$ is H, $CD_3$, $C_1$-$C_6$ alkyl, alkoxy $C_1$-$C_6$ alkyl, 3- to 10-membered mono or bicyclic cycloalkyl, 4- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-2 $R^{4a}$;

$R^{4a}$ is H, $NR^5R^6$, $C_1$-$C_6$ alkyl, $C_3$-$C_8$ cycloalkyl, hydroxy $C_1$-$C_6$ alkyl or alkoxy $C_1$-$C_6$ alkyl;

$R^5$ and $R^6$ are independently H or $C_1$-$C_4$ alkyl; or $R^5$ and $R^6$ are taken together with the nitrogen atom to which they are attached to form a 3-10 membered heterocyclyl ring substituted with 0-2 substituents selected from H, $C_1$-$C_4$ alkyl and OH;

or a pharmaceutically acceptable salt, tautomer or stereoisomer thereof.

In another preferred embodiment, there is provided a compound of the formula,

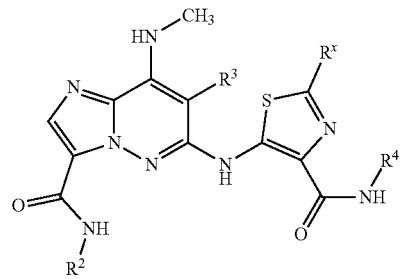

wherein $R^x$ is $C_1$-$C_3$ alkyl;

$R^2$ is H, $C_1$-$C_6$ alkyl, $C_3$-$C_8$ cycloalkyl, hydroxy $C_1$-$C_6$ alkyl, alkoxy $C_1$-$C_6$ alkyl, $C_3$-$C_8$ cycloalkyl $C_1$-$C_6$ alkyl-, di ($C_1$-$C_4$) alkyl aminoalkyl-, aryl, heteroaryl, or heterocyclyl $C_1$-$C_6$ alkyl-, substituted with 0-2 $R^{2a}$;

$R^{2a}$ is halo or $C_1$-$C_6$ alkyl;

$R^3$ is H, $C_1$-$C_6$ alkyl, $C_3$-$C_8$ cycloalkyl, hydroxy $C_1$-$C_6$ alkyl or alkoxy $C_1$-$C_6$ alkyl;

$R^4$ is H, $CD_3$, $C_1$-$C_6$ alkyl, alkoxy $C_1$-$C_6$ alkyl, 3- to 10-membered mono or bicyclic cycloalkyl, 4- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-2 $R^{4a}$;

$R^{4a}$ is H, $NR^5R^6$, $C_1$-$C_6$ alkyl, $C_3$-$C_8$ cycloalkyl, hydroxy $C_1$-$C_6$ alkyl or alkoxy $C_1$-$C_6$ alkyl;

$R^5$ and $R^6$ are independently H or $C_1$-$C_4$ alkyl; or $R^5$ and $R^6$ are taken together with the nitrogen atom to which they are attached to form a 3-10 membered heterocyclyl ring substituted with 0-2 substituents selected from H, $C_1$-$C_4$ alkyl and OH;

or a pharmaceutically acceptable salt, tautomer or stereoisomer thereof.

In another aspect, there is provided a compound selected from the exemplified examples within the scope of the first aspect, or a pharmaceutically acceptable salt, tautomer or stereoisomer thereof.

In another aspect, there is provided a compound selected from any subset list of compounds within the scope of any of the above aspects.

In another embodiment, there is provided a pharmaceutical composition comprising one or more compounds of formula (I), or stereoisomers, tautomers, pharmaceutically acceptable salts, solvates, or prodrugs thereof, and a pharmaceutically acceptable carrier or diluent.

The present invention is also directed to pharmaceutical compositions useful in treating diseases associated with the modulation of IL-12, IL-23 and/or IFNα by acting on Tyk-2 to cause signal transduction inhibition, comprising compounds of formula I, or pharmaceutically-acceptable salts thereof, and pharmaceutically-acceptable carriers or diluents.

The invention further relates to methods of treating diseases associated with the modulation of IL-12, IL-23, and/or IFNα, comprising administering to a patient in need of such treatment a therapeutically-effective amount of a compound according to formula I.

The present invention also provides processes and intermediates for making the compounds of the present invention.

The present invention also provides a method for treating proliferative, metabolic, allergic, autoimmune and inflammatory diseases (or use of the compounds of the present invention for the manufacture of a medicament for the treatment of these diseases), comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method of treating an inflammatory or autoimmune disease (or use of the compounds of the present invention for the manufacture of a medicament for the treatment of these diseases) comprising administering to a patient in need of such treatment a therapeutically-effective amount of a compound of Formula I.

The present invention also provides a method for treating a disease (or use of the compounds of the present invention for the manufacture of a medicament for the treatment of these diseases), comprising administering to a patient in need of such treatment a therapeutically-effective amount of a compound of Formula I, wherein the disease is rheumatoid arthritis, multiple sclerosis, systemic lupus erythematosus (SLE), lupus nephritis, cutaneous lupus, inflammatory bowel disease, psoriasis, Crohn's Disease, psoriatic arthritis, Sjögren's syndrome, systemic scleroderma, ulcerative colitis, Graves' disease, discoid lupus erythematosus, adult onset Stills, systemic onset juvenile idiopathic arthritis, gout, gouty arthritis, type 1 diabetes, insulin dependent diabetes mellitus, sepsis, septic shock, Shigellosis, pancreatitis (acute or chronic), glomerulonephritis, autoimmune gastritis, diabetes, autoimmune hemolytic anemia, autoimmune neutropenia, thrombocytopenia, atopic dermatitis, myasthenia gravis, pancreatitis (acute or chronic), ankylosing spondylitis, pemphigus vulgaris, Goodpasture's disease, antiphospholipid syndrome, idiopathic thrombocytopenia, ANCA-associated vasculitis, pemphigus, Kawasaki disease, Chronic Inflammatory Demyelinating Polyneuropathy (CIDP), dermatomyositis, polymyositis, uveitis, Guillain-Barre syndrome, autoimmune pulmonary inflammation, autoimmune thyroiditis, autoimmune inflammatory eye disease, and chronic demyelinating polyneuropathy.

The present invention also provides a method of treating an inflammatory or autoimmune disease (or use of the compounds of the present invention for the manufacture of a medicament for the treatment of these diseases), comprising administering to a patient in need of such treatment a therapeutically-effective amount of a compound of Formula I, wherein the disease is selected from systemic lupus erythematosus (SLE), lupus nephritis, cutaneous lupus, Crohn's Disease, ulcerative colitis, type 1 diabetes, psoriasis, rheumatoid arthritis, systemic onset juvenile idiopathic arthritis, ankylosing spondylitis, and multiple sclerosis.

The present invention also provides a method for treating a rheumatoid arthritis (or use of the compounds of the present for the manufacture of a medicament for the treatment of rheumatoid arthritis, comprising administering to a patient in need of such treatment a therapeutically-effective amount of a compound of Formula I.

In addition, the present invention also provides a method of treating a condition (or use of the compounds of the present invention for the manufacture of a medicament for the treatment of these conditions) comprising administering to a patient in need of such treatment a therapeutically-effective amount of a compound of Formula I, wherein the condition is selected from acute myelogenous leukemia, chronic myelogenous leukemia, metastatic melanoma, Kaposi's sarcoma, multiple myeloma, solid tumors, ocular neovascularization, and infantile haemangiomas, B cell lymphoma, systemic lupus erythematosus (SLE), rheumatoid arthritis, psoriatic arthritis, multiple vasculitides, idiopathic thrombocytopenic purpura (ITP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evans syndrome, hemolytic uremic syndrome/thrombotic thrombocytopenic purpura (HUS/TTP), sarcoidosis, Sjögren's syndrome, peripheral neuropathies, pemphigus vulgaris and asthma.

The present invention also provides a method of treating a IL-12, IL-23, and/or IFNα mediated disease (or use of the compounds of the present invention for the manufacture of a medicament for the treatment of said diseases), comprising administering to a patient in need of such treatment a therapeutically-effective amount of a compound of formula I The present invention also provides a method of treating a IL-12, IL-23 and/or IFNα mediated disease (or use of the compounds of the present invention for the manufacture of a medicament for the treatment of these diseases), comprising administering to a patient in need of such treatment a therapeutically-effective amount of a compound of formula I, wherein the IL-12, IL-23 and/or IFNα mediated disease is a disease modulated by IL-12, IL-23 and/or IFNα.

The present invention also provides a method of treating diseases, comprising administering to a patient in need of such treatment a therapeutically-effective amount of a compound of formula I in combination with other therapeutic agents.

The present invention also provides the compounds of the present invention use in therapy.

In another embodiment, compounds of formula I are selected from exemplified compounds or combinations of exemplified compounds or other embodiments herein.

In another embodiment are compounds having an $IC_{50}$<1000 nM in at least one of the assays described below.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DETAILED DESCRIPTION OF THE INVENTION

The following are definitions of terms used in this specification and appended claims. The initial definition provided for a group or term herein applies to that group or term throughout the specification and claims, individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —CONH$_2$ is attached through the carbon atom.

The term "optionally substituted" in reference to a particular moiety of the compound of Formula I (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "at least one chemical entity" is interchangeable with the term "a compound."

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of both straight or branched configuration and having one or more triple carbon-carbon bonds that may occur in any stable point along the chain. For example, "$C_2$-6 alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

One skilled in the field will understand that, when the designation "CO$_2$" is used herein, this is intended to refer to the group

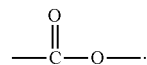

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl(C$_{0-4}$)alkyl includes a substituted lower alkyl having at least one aryl substituent and also includes an aryl directly bonded to another group, i.e., aryl(C$_0$)alkyl. The term "heteroarylalkyl" refers to a substituted alkyl group as defined above where at least one of the substituents is a heteroaryl.

When reference is made to a substituted alkenyl, alkynyl, alkylene, alkenylene, or alkynylene group, these groups are substituted with one to three substituents as defined above for substituted alkyl groups.

The term "alkoxy" refers to an oxygen atom substituted by alkyl or substituted alkyl, as defined herein. For example, the term "alkoxy" includes the group —O—C$_{1-6}$alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto, (i.e., =O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion. Ring double bonds, as used herein, are double bonds that are formed between two adjacent ring atoms (e.g., C=C, C=N, or N=N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, S(O)$_2$H, or S(O)H group.

The term "cycloalkyl" refers to cyclized alkyl groups, including mono-, bi- or poly-cyclic ring systems. C$_3$-7 cycloalkyl is intended to include C$_3$, C$_4$, C$_5$, C$_6$, and C$_7$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3, 4, 5, 6, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted.

Accordingly, in compounds of formula I, the term "cycloalkyl" includes cyclopropyl, cyclobutyl, cyclopentyl, cyclohexyl, cycloheptyl, bicyclooctyl etc., as well as the ring systems such as the following:

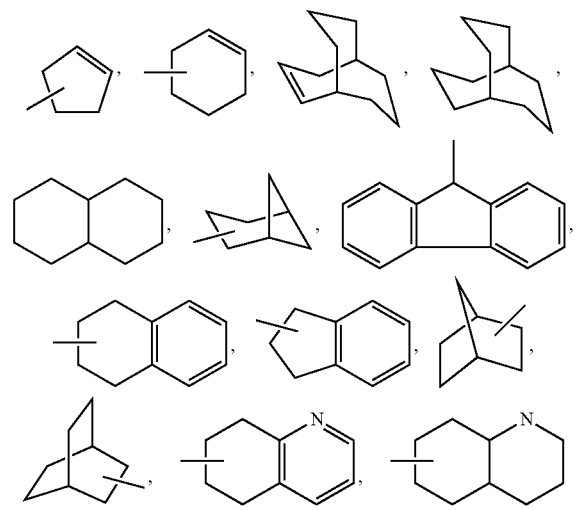

and the like, which optionally may be substituted at any available atoms of the ring(s). Preferred cycloalkyl groups include cyclopropyl, cyclopentyl, cyclohexyl, and

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes OCF$_3$.

Thus, examples of aryl groups include:

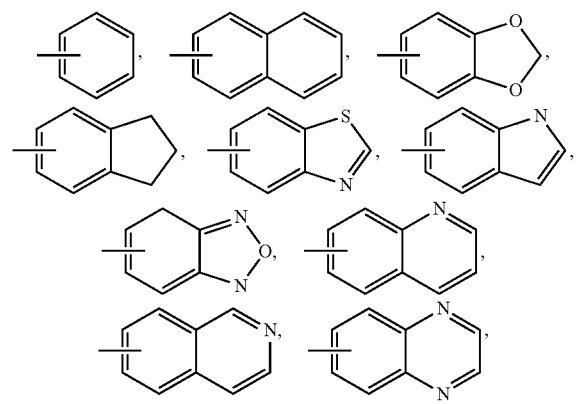

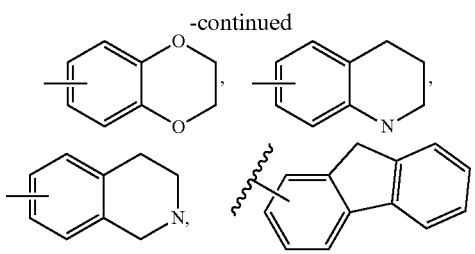

(fluorenyl) and the like, which optionally may be substituted at any available carbon or nitrogen atom. A preferred aryl group is optionally-substituted phenyl.

The terms "heterocycle", "heterocycloalkyl", "heterocyclo", "heterocyclic", or "heterocyclyl" may be used interchangeably and refer to substituted and unsubstituted 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or fully unsaturated. The heterocyclo group may be attached at any available nitrogen or carbon atom. As used herein the terms "heterocycle", "heterocycloalkyl", "heterocyclo", "heterocyclic", and "heterocyclyl" include "heteroaryl" groups, as defined below.

In addition to the heteroaryl groups described below, exemplary monocyclic heterocyclyl groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl. Additional monocyclic heterocyclyl groups include

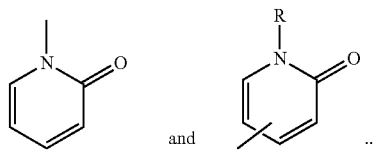

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (0, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzindolyl, phenanthrollinyl, acridinyl, phenanthridinyl, xanthenyl and the like.

In compounds of formula I, preferred heteroaryl groups include

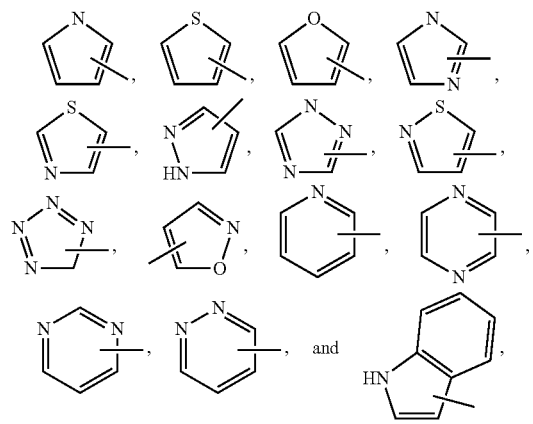

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0 to 2, substituents selected from those recited above for the aryl, cycloalkyl, heterocyclo and/or heteroaryl groups, as appropriate.

The term "carbocyclyl" or "carbocyclic" refers to a saturated or unsaturated monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl. The carbocyclic ring may be substituted in which case the substituents are selected from those recited above for cycloalkyl and aryl groups.

The term "heteroatoms" shall include oxygen, sulfur and nitrogen.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula I may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s) may include zwitterions (inner salts), e.g., when a compound of formula I, contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs and solvates of the inventive compounds are also contemplated. The term "prodrug" denotes a compound which, upon administration to a subject, undergoes chemical conversion by metabolic or chemical processes to yield a compound of the formula I, and/or a salt and/or solvate thereof. Any compound that will be converted in vivo to provide the bioactive agent (i.e., the compound for formula I) is a prodrug within the scope and spirit of the invention. For example, compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$alkanoyloxy-$C_{1-6}$alkyl, e.g., acetoxymethyl, pivaloyloxymethyl or propionyloxymethyl, $C_{1-6}$alkoxycarbonyloxy-$C_{1-6}$alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well-known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:
a) Bundgaard, H., ed., *Design of Prodrugs*, Elsevier (1985), and Widder, K. et al., eds., *Methods in Enzymology*, 112:309-396, Academic Press (1985);
b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991); and
c) Bundgaard, H., *Adv. Drug Deliv. Rev.*, 8:1-38 (1992), each of which is incorporated herein by reference.

Compounds of the formula I and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers.

It should further be understood that solvates (e.g., hydrates) of the compounds of Formula I are also with the scope of the present invention. Methods of solvation are generally known in the art.

Utility

The compounds of the invention modulate IL-23-stimulated and IFNα-stimulated cellular functions, including gene transcription. Other types of cellular functions that may be modulated by the compounds of the instant invention include, but are not limited to, IL-12-stimulated responses.

Accordingly, compounds of formula I have utility in treating conditions associated with the modulation of the function of IL-23 or IFNα, and particularly the selective inhibition of function of IL-23, IL-12 and/or IFNα, by acting on Tyk2 to mediate signal transduction. Such conditions include IL-23-, IL-12-, or IFNα-associated diseases in which pathogenic mechanisms are mediated by these cytokines.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as modulators of IL-23-, IL-12 and IFNα-stimulated cellular responses, compounds of Formula I are useful in treating IL-23-, IL-12- or IFNα-associated diseases including, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosis, cutaneous lupus, lupus nephritis, discoid lupus erythematosus, psoriasis; auto-inflammatory diseases including CAPS, TRAPS, FMF, adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, cutaneous lupus, lupus nephritis, discoid lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia [should this be hypoxia], vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's disease, ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

When the terms "IL-23-, IL-12- and/or IFNα-associated condition" or "IL-23-, IL-12- and/or IFNα-associated disease or disorder" are used herein, each is intended to encompass all of the conditions identified above as if repeated at length, as well as any other condition that is affected by IL-23, IL-12 and/or IFNα.

The present invention thus provides methods for treating such conditions, comprising administering to a subject in need thereof a therapeutically-effective amount of at least one compound of Formula I or a salt thereof. "Therapeutically effective amount" is intended to include an amount of a compound of the present invention that is effective when administered alone or in combination to inhibit IL-23, IL-12 and/or IFNα function and/or treat diseases.

The methods of treating IL-23-, IL-12 and/or IFNα-associated conditions may comprise administering compounds of Formula I alone or in combination with each other and/or other suitable therapeutic agents useful in treating such conditions. Accordingly, "therapeutically effective amount" is also intended to include an amount of the combination of compounds claimed that is effective to inhibit IL-23, IL-12 and/or IFNα function and/or treat diseases associated with IL-23, IL-12 and/or IFNα.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating IL-23-, IL-12- or IFNα-associated conditions by inhibiting Tyk2-mediated signal transduction, including IL-23-, IL-12- and/or IFNα-mediated diseases, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula I and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Remington's Pharmaceutical Sciences, 17th Edition (1985), which is incorporated herein by reference in its entirety.

The compounds of Formula I may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrastemal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5 250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species that are affected by modulation of IL-23, IL-12 and/or IFNα-mediated functions.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the preparations and examples section set out hereinafter. Some of the compounds described were chiral and were prepared homochiral from commercially available starting material.

Scheme 1

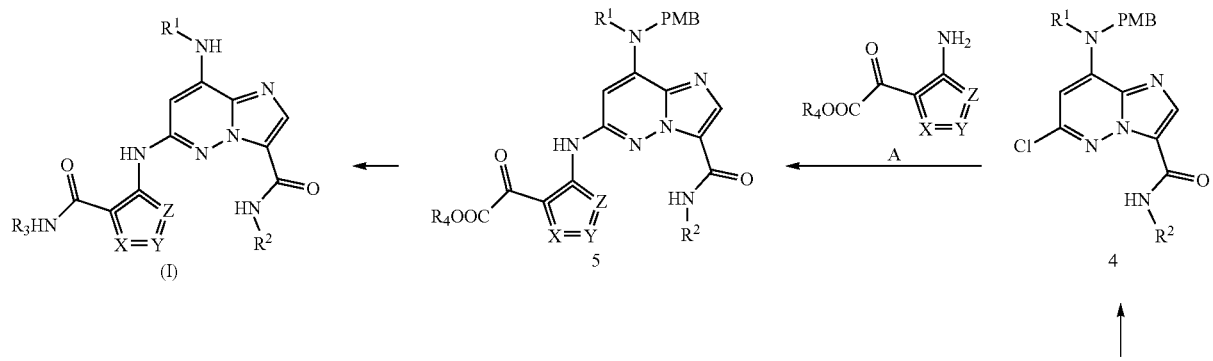

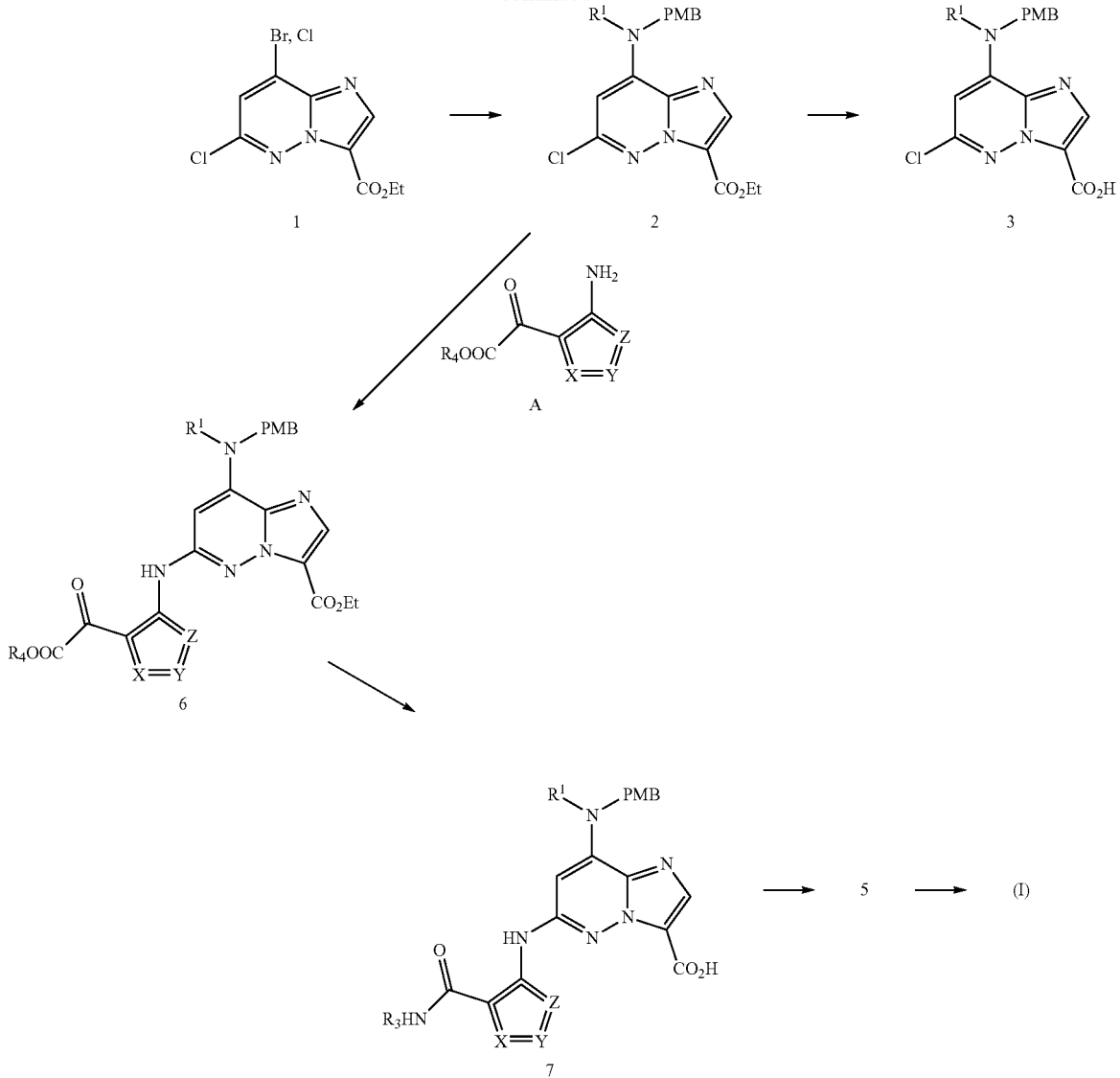

The compounds of Formula (I) can be prepared according to Scheme 1. Treatment of imidazopyridazine derivative (1) (WO 2009/100375) with p-methoxybenzyl protected amine ($R^1$NHPMB) provides ester 2. The latter is hydrolyzed to acid 3, which is subsequently converted to amide 4 by standard coupling reaction. Buchwald reaction of 4 with A, promoted by catalysts such as tris(dibenzylideneacetone)dipalladium(0)/XantPhos and palladium(II) acetate/BrettPhos, affords 5. Compound 5, which in the case of the methyl or ethyl ester is hydrolyzed to the carboxylic acid under basic conditions (whereas in some cases the Buchwald reaction produces the carboxylic acid). The carboxylic acid is coupled to primary amines using coupling reagents such as, BOP-reagent, EDCI/HOBT or HATU. Removal of the PMB protection group under acidic conditions leads to the formation of compound (I). Alternatively, Buchwald reaction can be performed with 2 and A, followed by hydrolysis and coupling steps to give rise to an intermediate, which is then transformed to compound (I) by hydrolysis, followed by amide formation and deprotection.

Intermediate A: Intermediate A, when X=N; Y=N—$CH_3$; Z=CH is commercially available as the methyl or ethyl ester. Intermediate A, when X=N—$CH_3$; Y=N; Z=CH is commercially available as the methyl or ethyl ester. Intermediate A, when X=CH; Y=N—$CH_3$; X=N is commercially available as the methyl or ethyl ester. Intermediate A, when X=N; Y=N—$CH_2CH_3$; Z=CH is commercially available as the methyl or ethyl ester. Intermediate A, when X=S; Y=N—CH; Z=CH is commercially available as the methyl or ethyl ester. Intermediate A, when X=O; Y=N—CH; Z=CH is commercially available as the methyl or ethyl ester.

Intermediate A, when X=N; Y=N—NH; Z=CH can be prepared from commercially available 15 (Scheme 2). Compound 15 can be N-alkylated in a variety of ways to provide 16. It can be N-alkylated with 4-methoxybenzyl chloride in the presence of a base such as potassium carbonate, cesium carbonate, and sodium hydride. Then, 16 can be converted to A using methods such as ammonium chloride, zinc in EtOH or tin(II)chloride, dihydrate in refluxing ethyl acetate to afford A. The 4-methoxybenyl group can be removed in the last step under acidic conditions that remove other protecting groups.

Scheme 2

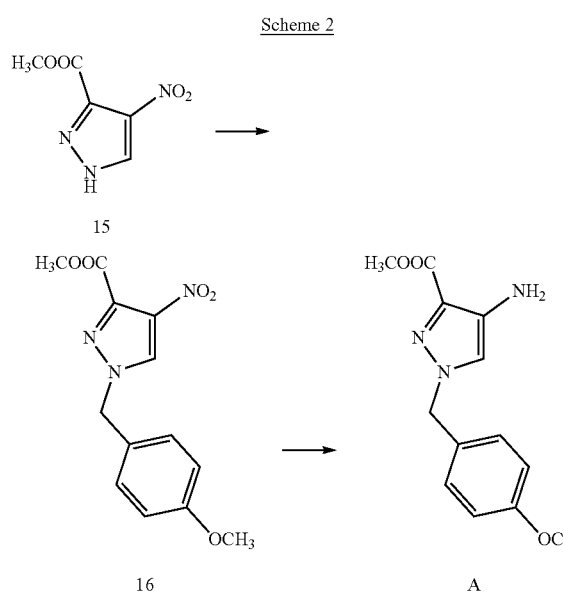

Intermediate A, when X=N; Y=S; Z=CH can be prepared from commercially available 17 (Scheme 3). 17 can be sulfonylated with 4-toluenesulfonyl chloride to afford 18 which can be treated with thiomethyl acetate under basic conditions to give 19. Treatment with acid gives A.

Scheme 3

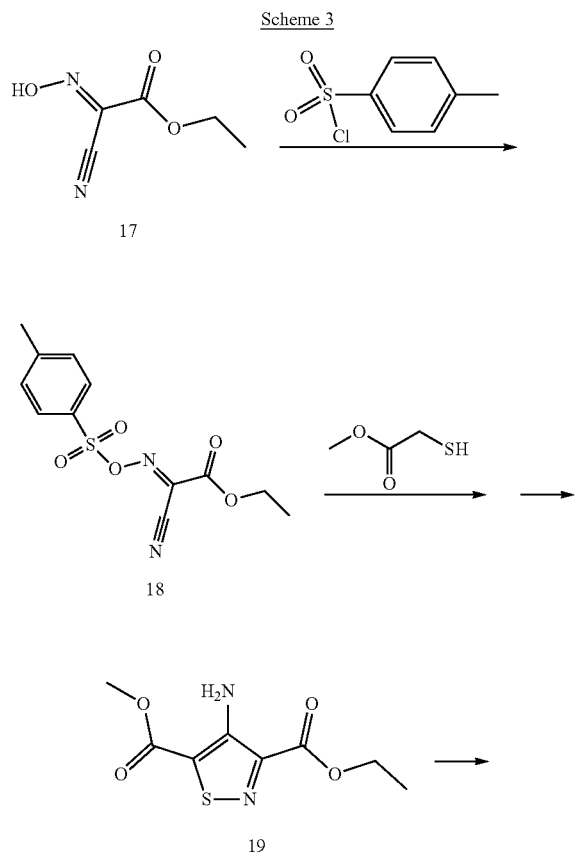

Intermediate A, when X=N; Y=CH; Z=S can be prepared from commercially available 20 (Scheme 4). 20 can be treated with benzophenone imine under Buchwald conditions to give 21. Treatment with acid gives A.

Scheme 4

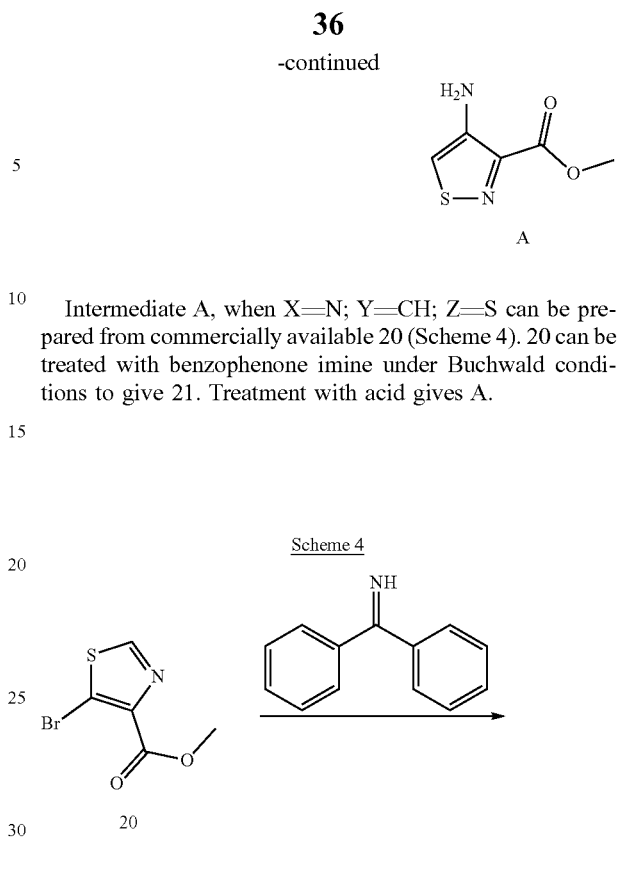

Intermediate A, when X=N; Y=C—CH₃; Z=S can be prepared from commercially available 22 (Scheme 5). 22 can be treated with acetic anhydride under basic conditions, followed by Lawesson's reagent to give A.

Scheme 5

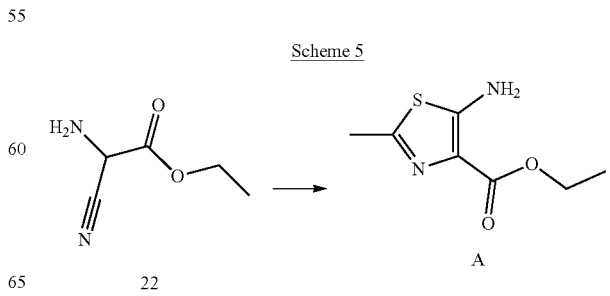

Scheme 6
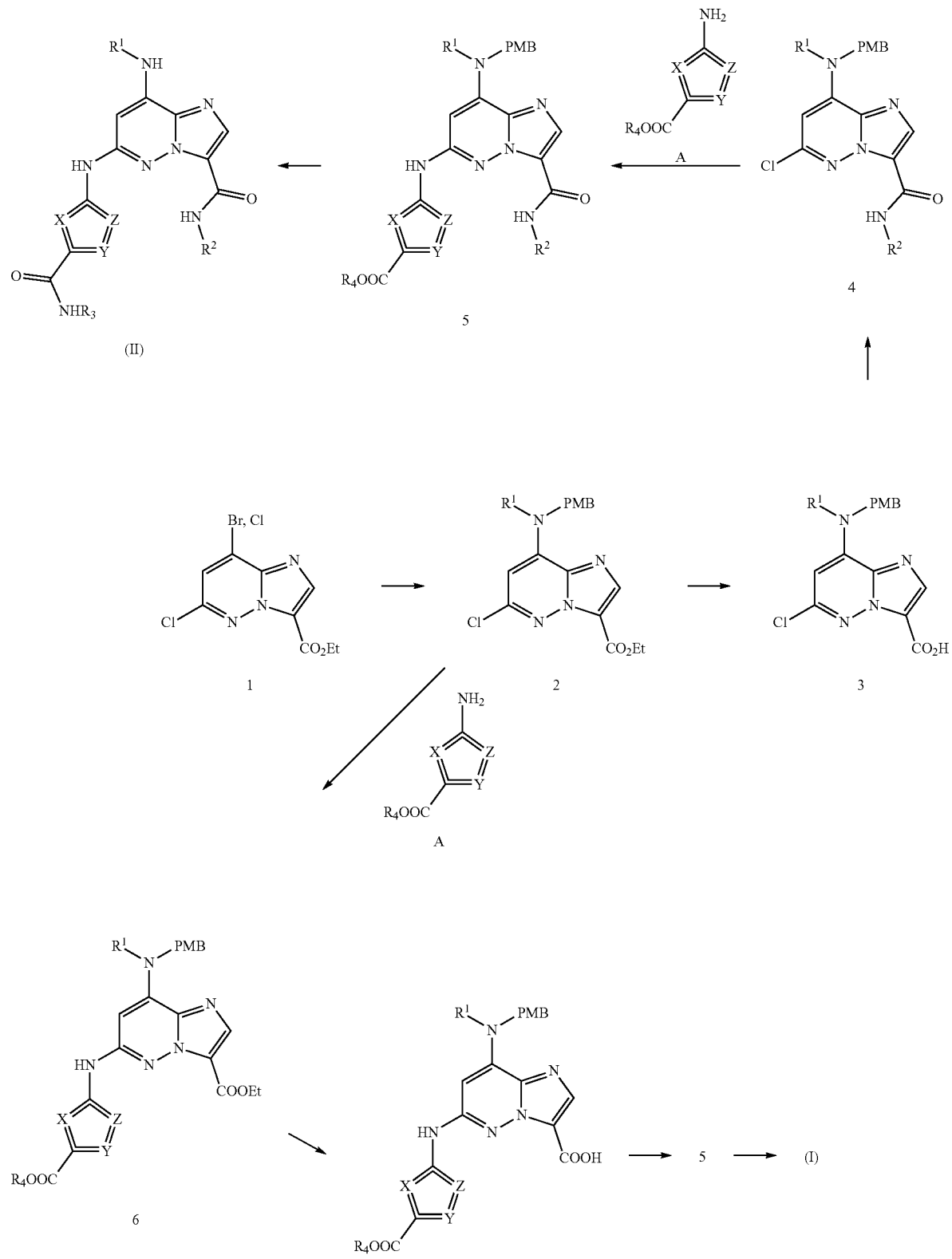

The compounds of Formula (II) can be prepared according to Scheme 6. Treatment of imidazopyridazine derivative (1) (WO 2009/100375) with p-methoxybenzyl protected amine ($R^1$NHPMB) provides ester 2. The latter is hydrolyzed to acid 3, which is subsequently converted to amide 4 by standard coupling reaction. Buchwald reaction of 4 with A, promoted by catalysts such as tris(dibenzylideneacetone)dipalladium(0)/XantPhos and palladium(II) acetate/BrettPhos, affords 5. Compound 5, which in the case of the methyl or ethyl ester is hydrolyzed to the carboxylic acid under basic conditions (whereas in some cases the Buchwald reaction produces the carboxylic acid). The carboxylic acid is coupled to primary amines using coupling reagents such as, BOP-reagent, EDCI/HOBT or HATU. Removal of the PMB protection group under acidic conditions leads to the formation of compound (II). Alternatively, Buchwald reaction can be performed with 2 and A, followed by hydrolysis and coupling steps to give rise to an intermediate, which is then transformed to compound (II) by hydrolysis, followed by amide formation and deprotection.

Intermediate A: Intermediate A, when X=CH; Y=N; Z=N—$CH_3$ is commercially available as the methyl or ethyl ester. Intermediate A, when X=CH; Y=N—$CH_3$; Z=N is commercially available as the methyl or ethyl ester.

Analytical HPLC Method Employed in Characterization of Examples:
Analytical HPLC was performed using the following methods:

Method A:
Column—Water Acquity UPLC (LCMS) BEH C18, 2.1×50 mm, 1.7 μm particles; Mobile Phase—(A) water+0.05% TFA, (B) acetonitrile+0.05% TFA, 2%-98% B (0 to 1 min) 98% B (to 1.5 min) 98%-2% B (to 1.6 min); Gradient Time—1.6 min; Flow Rate—0.8 mL/min; Analysis Time—2.2 min; Detector 1: UV at 254 nm, Detector 2: MS (ESI+).

Method B:
Column—(LCMS) Zorbax SB C18, 2.1×30 mm, 3.5 μm particles; Mobile Phase—(A) acetonitrile+10 mM ammonium formate in water (2:98), (B) acetonitrile+10 mM ammonium formate in water (98:2), 6%-100% B (0 to 1.5 min) 100% B (to 2.2 min) 100%-6% B (to 2.6 min) 6% B (to 3 min); Gradient Time—3 min; Flow Rate—1.5 mL/min; Analysis Time—3 min; Detector 1: UV at 254 nm, Detector 2: MS (ESI+).

Method C:
Column—(HPLC) YMC CombiScreen ODS-A C18, 4.6×50 mm, 3.5 μm particles; Mobile Phase—(A) 90:10 water:MeOH+0.1% TFA, (B) 90:10 MeOH:water+0.1% TFA, 0 to 100% B (to 4 min, 100% B (to 5 min); Gradient Time—4 min; Flow Rate—4 mL/min; Analysis Time—5 min; Detector 1: UV at 220 nm, Detector 2: UV at 254 nm.

Method D:
Column—Water Acquity UPLC (LCMS) BEH C18, 2.1×50 mm, 1.7 μm particles; Mobile Phase—(A) 5:95 acetonitrile:water+0.1% TFA; (B) 95:5 acetonitrile:water+0.1% TFA, 0-100% B (0 to 3 min) 100% B (to 3.75 min); Gradient Time—3 min; Flow Rate—1.11 mL/min; Analysis Time—3.75 min; Detector 1: UV at 220 nm, Detector 2: MS (ESI+).

Method E:
Column: Waters Acquity UPLC BEH C18, 2.1×50 mm, 1.7-im particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Method F:
Column: Waters Acquity UPLC BEH C18, 2.1×50 mm, 1.7-im particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min.

Example 1

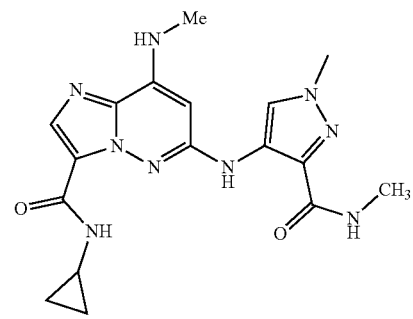

Example 1

1a

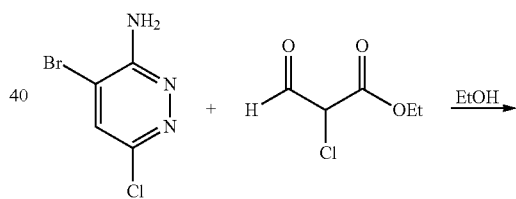

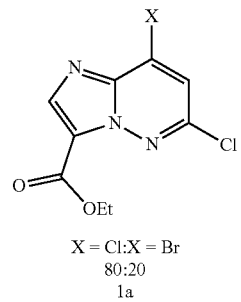

X = Cl:X = Br
80:20
1a

To a solution of 4-bromo-6-chloropyridazin-3-amine (175 g, 840 mmol) in ethanol (2 L) was added ethyl 2-chloro-3-oxopropanoate (202 g, 1343 mmol) and the reaction was heated to 80° C. for 16 hours. The solvent was removed in vacuo and the residual material was diluted with water and dichloromethane. The biphasic mixture was passed through a celite bed and the filtrate was separated into two layers. The dichloromethane layer was separated and then washed with water and saturated aqueous sodium chloride (brine), it was then dried over anhydrous sodium sulfate, filtered and concentrated. The resulting crude product was purified using silica gel chromatography (0 to 20% ethyl acetate in petroleum ether). The product fractions were dried and then triturated with 10% methyl tert-butyl ether in petroleum ether (500 mL). The product was filtered off and rinsed with petroleum ether to provide 1a (73 g, 33% yield) as a mixture of the C8-bromo and C8-chloro species (~80:20), the mixture was used as such in the subsequent steps (referred to as the chloride for simplicity).

$^1$H NMR (300 MHz, CDCl$_3$):

Chloro: δ 8.37 (s, 1H), 7.38 (s, 1H), 4.47 (q, J=7.2 Hz, 2H), 1.44 (t, J=7.2 Hz, 3H).

Bromo: δ 8.38 (s, 1H), 7.57 (s, 1H), 4.47 (q, J=7.2 Hz, 2H), 1.44 (t, J=7.2 Hz, 3H).

LC retention time chloro: 1.04 min [B]; bromo: 1.07 [B]. Mass Spectrometry ("MS") (E+) m/z: 260 (chloro); 304 (bromo) (MH$^+$).

1b

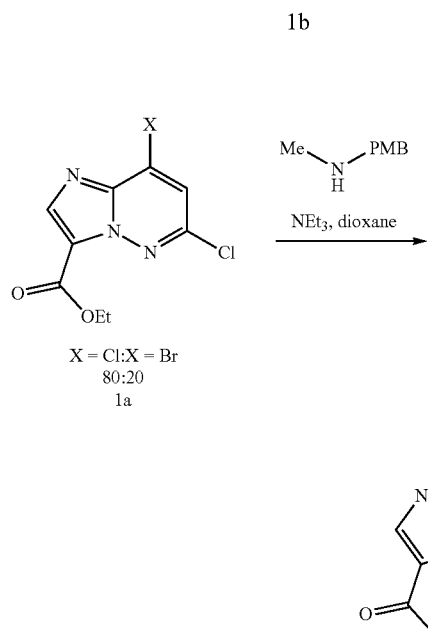

X = Cl:X = Br
80:20
1a

A solution of ethyl 8-chloro-6-chloroimidazo[1,2-b]pyridazine-3-carboxylate (1a) (7.35 g, 28.3 mmol), 1-(4-methoxyphenyl)-N-methylmethanamine (4.74 g, 31.4 mmol) and triethylamine (6.73 mL, 48.3 mmol) in dioxane (75 mL) was heated in an oil bath at 90° C. for 2.5 hours. The reaction was cooled to room temperature and concentrated to provide a sludge that was triturated with water to provide a solid which was filtered, rinsed with water and then collected with dichloromethane. The solution was dried over anhydrous sodium sulfate, filtered and concentrated to provide 1b (8.95 g, 84% yield). $^1$H NMR (400 MHz, CHLOROFORM-d) δ 8.13 (s, 1H), 7.17 (d, J=8.6 Hz, 2H), 6.87 (d, J=8.6 Hz, 2H), 6.12 (s, 1H), 5.50 (s, 2H), 4.46 (q, J=7.1 Hz, 2H), 3.81 (s, 3H), 3.18 (s, 3H), 1.74-1.58 (m, 1H), 1.44 (t, J=7.2 Hz, 3H). LC retention time 1.04 min [A]. MS (E+) m/z: 375 (MH$^+$).

1c

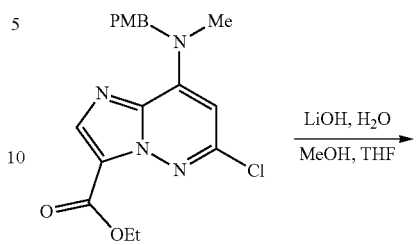

1b

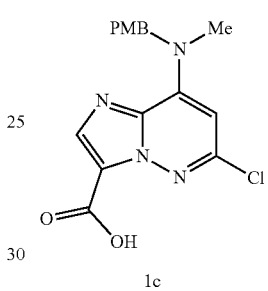

1c

To a solution of ethyl 6-chloro-8-((4-methoxybenzyl)(methyl)amino)imidazo[1,2-b]pyridazine-3-carboxylate (1b) (1.20 g, 3.20 mmol) in methanol (15 mL) and tetrahydrofuran (15 mL) was added 0.5 M (aqueous) lithium hydroxide (25.6 mL, 12.81 mmol) and the reaction was stirred overnight. The reaction was diluted with water and then the methanol was removed in vacuo, the resulting solution was adjusted to pH ~4 using hydrochloric acid (1 M aqueous) the product was extracted with dichloromethane and the combined organic layers were dried over sodium sulfate, filtered, and concentrated to provide 1c (1.00 g, 81% yield), which was used without further purification. LC retention time 0.90 min [A]. MS (E+) m/z: 347 (MH$^+$).

1d

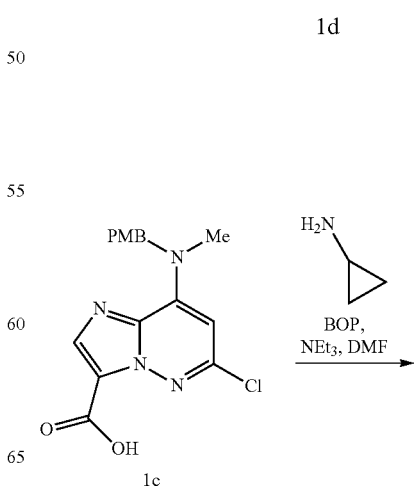

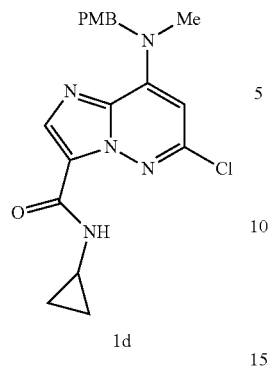

1d

A mixture of 6-chloro-8-((4-methoxybenzyl)(methyl)amino)imidazo[1,2-b]pyridazine-3-carboxylic acid (1c) (536 mg, 1.546 mmol), cyclopropanamine (0.321 mL, 4.64 mmol), and triethylamine (0.646 mL, 4.64 mmol) in dimethylformamide (3 mL) was treated with (benzotriazol-1-yloxy)tris(dimethylamino)phosphonium hexafluorophosphate (BOP, 752 mg, 1.700 mmol), and the reaction was stirred at room temperature for 5 hours. The desired product was precipitated with water (5 mL), and collected by filtration. The solids were rinsed twice with water, once with a small amount of methanol, and dried under vacuum to yield 6-chloro-N-cyclopropyl-8-((4-methoxybenzyl)(methyl)amino)imidazo[1,2-b]pyridazine-3-carboxamide (1d) (480 mg, 80% yield). $^1$H NMR (400 MHz, DMSO-$d_6$) δ 8.55 (d, J=3.5 Hz, 1H), 8.06 (s, 1H), 7.19 (d, J=8.6 Hz, 2H), 6.89 (d, J=8.8 Hz, 2H), 6.39 (s, 1H), 5.52 (br. s., 2H), 3.73 (s, 3H), 3.31 (s, 3H), 2.88 (tq, J=7.2, 3.8 Hz, 1H), 0.89-0.75 (m, 2H), 0.63-0.51 (m, 2H). LC retention time 1.04 min [A]. MS (E+) m/z: 386 (MH$^+$).

1e

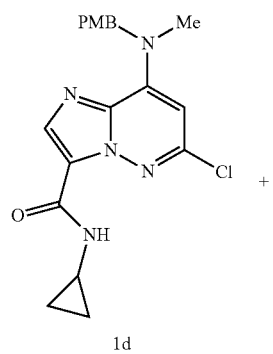

1d

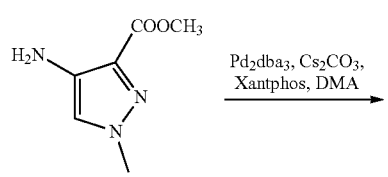

Pd$_2$dba$_3$, Cs$_2$CO$_3$,
Xantphos, DMA
→

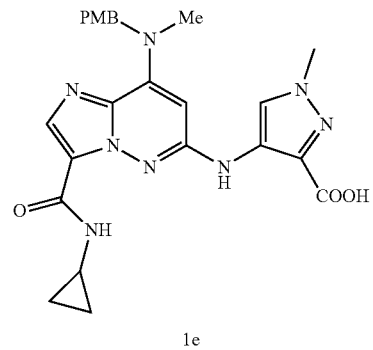

1e

A mixture of 6-chloro-N-cyclopropyl-8-((4-methoxybenzyl)(methyl) amino)imidazo[1,2-b]pyridazine-3-carboxamide (1d) (125 mg, 0.324 mmol), methyl 4-amino-1-methyl-1H-pyrazole-3-carboxylate (101 mg, 0.648 mmol) [Free based (sodium bicarbonate solution/EtOAc) from HCl salt purchased from Art-Chem-BB], Pd2(dba)3 (29.7 mg, 0.032 mmol), XANTPHOS (37.5 mg, 0.065 mmol) and Cs$_2$CO$_3$ (422 mg, 1.296 mmol) in DMA (2 mL) was degassed by bubbling N$_2$ through the mixture for 5 minutes. The reaction vessel was sealed and heated to 125° C. for 8 hr. After cooling to rt, the reaction mixture was partitioned between EtOAc (30 ml) and water (20 ml). The organic layer was extracted with 1N NaOH (10 ml) and the combined aqueous layers were washed with EtOAc (20 ml). The aqueous layer was acidified to pH 1 with 1N HCl and the mixture was transferred to a separatory funnel and the aqueous layer was extracted with EtOAc (3×25 ml). The combined organic layers were washed with 10% LiCl solution (2×50 ml) and brine (50 ml). After drying (Na$_2$SO$_4$) and filtration the organic layer was concentrated to afford 4-((3-(cyclopropylcarbamoyl)-8-((4-methoxybenzyl)-(methyl)amino)imidazo[1,2-b]pyridazin-6-yl)amino)-1-methyl-1H-pyrazole-3-carboxylic acid (1e) (126 mg, 0.257 mmol, 79% yield) as a tan solid. LC retention time 2.60 min [C]. MS (E+) m/z: 491 (MH$^+$).

1) BOP-reagent, DMF, Et$_3$N, CH$_3$NH$_2$
2) HCl in dioxane, DCM
→

1e

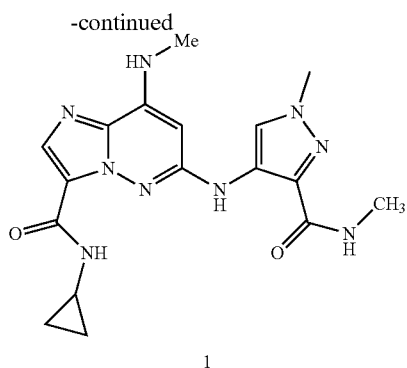

Example 1

A mixture of 4-((3-(cyclopropylcarbamoyl)-8-((4-methoxybenzyl)(methyl)amino)imidazo[1,2-b]pyridazin-6-yl)amino)-1-methyl-1H-pyrazole-3-carboxylic acid (1e) (12 mg, 0.024 mmol), methanamine, 2M in THF (0.061 mL, 0.122 mmol), BOP-reagent (14.07 mg, 0.032 mmol) and triethylamine (10.23 μl, 0.073 mmol) in DMF (0.25 mL) was allowed to stand at rt for 1 hr. The volatiles were removed in vacuo to afford a yellow residue that was treated with HCl, 4N in dioxane (0.060 mL, 0.238 mmol) in DCM (0.2 mL) and was allowed to stand at rt for 1 hr. The reaction mixture was concentrated and the residue was dissolved in DMF. The solution was purified via preparative LC/MS with the following conditions: Column: Waters XBridge C18, 19×250 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 0-100% B over 25 minutes, then a 5-minute hold at 100% B; Flow: 20 mL/min. Fractions containing the desired product were combined and dried via centrifugal evaporation to afford N-cyclopropyl-6-((1-methyl-3-(methylcarbamoyl)-1H-pyrazol-4-yl)amino)-8-(methylamino)imidazo[1,2-b]pyridazine-3-carboxamide (1) (5.8 mg, 0.015 mmol, 63% yield). LC retention time 0.99 min [D]. MS (E+) m/z: 384 (MH+). $^1$H NMR (500 MHz, DMSO-$d_6$) δ 8.88 (s, 1H), 8.64 (d, J=3.7 Hz, 1H), 8.22 (d, J=4.9 Hz, 1H), 8.14 (s, 1H), 7.81 (s, 1H), 7.39 (d, J=5.5 Hz, 1H), 5.98 (s, 1H), 3.93 (s, 3H), 2.92-2.89 (m, 1H), 2.86 (d, J=4.9 Hz, 3H), 2.76 (d, J=4.9 Hz, 3H), 0.84-0.72 (m, 2H), 0.57-0.47 (m, 2H).

The following Examples were prepared in a similar manner to Example 1

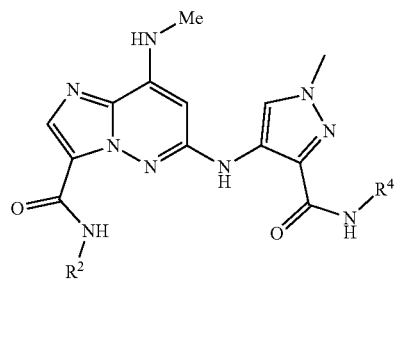

| Example number | R² | R⁴ | Rt (min) [Method] | m/z [M + H]⁺ |
|---|---|---|---|---|
| 2 | cyclopropyl | phenyl | 1.35 [D] | 446 |
| 3 | cyclopropyl | CH₂CH₂OMe | 0.99 [D] | 428 |
| 4 | cyclopropyl | 2-pyridyl | 0.99 [D] | 447 |
| 5 | cyclopropyl | 3-pyridyl | 0.78 [D] | 447 |
| 6 | cyclopropyl | 4-pyridyl | 0.87 [D] | 447 |

-continued

| Example number | R² | R⁴ | Rt (min) [Method] | m/z [M + H]⁺ |
|---|---|---|---|---|
| 7 | cyclopropyl | 3,4-dimethylpyridazin-6-yl | 1.01 [D] | 476 |
| 8 | cyclopropyl | pyrimidin-5-yl | 0.99 [D] | 448 |
| 9 | cyclopropyl | isopropyl | 2.38 [C] | 412 |
| 10 | cyclopropyl | CD₂H (CHD₂) | 0.94 [D] | 387 |
| 11 | cyclopropyl | 6-methoxypyridin-3-yl | 1.27 [D] | 477 |
| 12 | cyclopropyl | 4-methoxyphenyl | 1.46 [D] | 476 |
| 13 | cyclopropyl | benzo[1,3]dioxol-5-yl | 1.45 [D] | 490 |
| 14 | (1S,2R)-2-fluorocyclopropyl | CH₃ | 0.95 [D] | 402 |
| 15 | (1S,2R)-2-fluorocyclopropyl | phenyl | 1.58 [D] | 464 |
| 16 | cyclopropyl | cyclopropyl | 1.20 [E] | 410 |
| 17 | cyclopropyl | isobutyl | 1.38 [F] | 426 |

-continued
| Example number | R² | R⁴ | Rt (min) [Method] | m/z [M + H]⁺ |
|---|---|---|---|---|
| 18 | 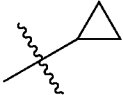 [SMILES: *C1CC1] | 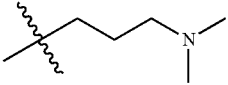 [SMILES: *CCCN(C)C] | 0.73 [F] | 455 |
| 19 |  | 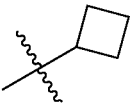 | 1.42 [E] | 424 |
| 20 |  | 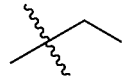 [SMILES: *CC] | 1.08 [F] | 398 |
| 21 |  | 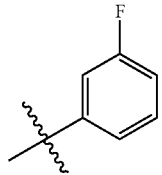 [SMILES: *c1cccc(F)c1] | 1.52 [E] | 464 |
| 22 |  | 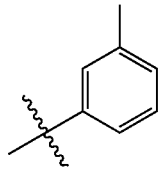 [SMILES: *c1cccc(C)c1] | 1.47 [F] | 460 |
| 23 |  | 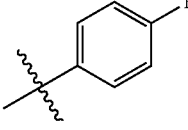 | 1.38 [F] | 464 |
| 24 |  | 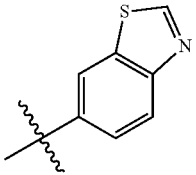 [SMILES: *c1ccc2ncsc2c1] | 1.34 [E] | 503 |
| 25 |  | 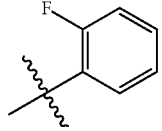 [SMILES: *c1ccccc1F] | 1.60 [F] | 464 |
| 26 |  | 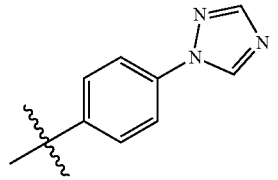 [SMILES: *c1ccc(-n2cncn2)cc1] | 1.20 [F] | 513 |

-continued

| Example number | R² | R⁴ | Rt (min) [Method] | m/z [M + H]⁺ |
|---|---|---|---|---|
| 27 | cyclopropyl | 4-(dimethylamino)phenyl | 0.93 [F] | 489 |

| Compound | ¹H NMR |
|---|---|
| 2 | ¹H NMR (500 MHz, DMSO-d₆) δ 10.17 (s, 1H), 8.80(s, 1H), 8.65 (d, J = 2.4 Hz, 1H), 8.28 (s, 1H), 7.89-7.79 (m, 3H), 7.41 (d, J = 4.3 Hz, 1H), 7.33 (t, J = 7.9 Hz, 2H), 7.09 (t, J = 7.6 Hz, 1H), 6.09 (s, 1H), 4.02 (s, 3H), 3.16 (d, J = 5.5 Hz, 3H), 2.91 (d, J = 3.7 Hz, 1H), 0.80 (d, J = 4.9 Hz, 2H), 0.54 (br. s., 2H). |
| 3 | ¹H NMR (500 MHz, DMSO-d₆) δ 8.83 (s, 1H), 8.64 (d, J = 3.7 Hz, 1H), 8.15 (s, 1H), 8.13 (t, J = 5.5 Hz, 1H), 7.81 (s, 1H), 7.39 (d, J = 4.9 Hz, 1H), 6.00 (s, 1H), 3.94 (s, 3H), 3.50-3.40 (m, 4H), 3.25 (s, 3H), 2.90 (td, J = 7.3, 3.7 Hz, 1H), 2.86 (d, J = 4.9 Hz, 3H), 0.86-0.71 (m, 2H), 0.56-0.49 (m, 2H). |
| 4 | ¹H NMR (500 MHz, DMSO-d₆) δ 9.45 (s, 1H), 8.66 (s, 1H), 8.63 (br. s., 1H), 8.37 (br. s., 1H), 8.31 (s, 1H), 8.16 (d, J = 8.4 Hz, 1H), 7.86 (s, 1H), 7.42 (br. s., 1H), 7.18 (d, J = 5.4 Hz, 1H), 6.54 (s, 1H), 6.11 (s, 1H), 4.01 (s, 3H), 2.94-2.82 (m, 4H), 0.78 (d, J = 5.4 Hz, 2H), 0.49 (br. s., 2H). |
| 5 | ¹H NMR (500 MHz, DMSO-d₆) δ 10.48 (s, 1H), 9.02 (d, J = 1.8 Hz, 1H), 8.75 (s, 1H), 8.64 (d, J = 3.7 Hz, 1H), 8.35-8.27 (m, 2H), 8.22 (d, J = 8.5 Hz, 1H), 7.83 (s, 1H), 7.44-7.33 (m, 2H), 6.10 (s, 1H), 4.02 (s, 3H), 2.96-2.81 (m, 4H), 0.85-0.74 (m, 2H), 0.59-0.47 (m, 2H). |
| 6 | ¹H NMR (500 MHz, DMSO-d₆) δ 10.56 (s, 1H), 8.70(s, 1H), 8.62(d, J = 3.3 Hz, 1H), 8.45 (d, J = 6.1 Hz, 2H), 8.32 (s, 1H), 7.87 (d, J = 6.4 Hz, 2H), 7.83 (s, 1H), 7.39 (d, J = 4.7 Hz, 1H), 6.11 (s, 1H), 4.03 (s, 3H), 2.95-2.82 (m, 4H), 0.83-0.69 (m, 2H), 0.53 (dd, J = 3.7, 2.1 Hz, 2H). |
| 7 | ¹H NMR (500 MHz, DMSO-d₆) δ 9.92 (s, 1H), 8.69-8.59 (m, 2H), 8.33 (s, 1H), 8.18 (s, 1H), 7.84 (s, 1H), 7.44 (br. s., 1H), 6.10 (s, 1H), 4.03 (s, 3H), 2.95-2.81 (m, 4H), 2.55 (s, 3H), 2.33 (s, 3H), 0.79 (d, J = 5.7 Hz, 2H), 0.51 (br. s., 2H). |
| 8 | ¹H NMR (500 MHz, DMSO-d₆) δ 10.72 (s, 1H), 9.24 (s, 2H), 8.91 (s, 1H), 8.70 (s, 1H), 8.63 (d, J = 3.7 Hz, 1H), 8.34 (s, 1H), 7.83 (s, 1H), 7.41 (d, J = 4.9 Hz, 1H), 6.12 (s, 1H), 4.03 (s, 3H), 2.95-2.81 (m, 4H), 0.84-0.71 (m, 2H), 0.60-0.45 (m, 2H). |
| 9 | ¹H NMR (400 MHz, DMSO-d₆) δ 8.98 (s, 1H), 8.66 (d, J = 3.5 Hz, 1H), 8.18 (s, 1H), 8.00-7.89 (m, 2H), 7.52 (br. s., 1H), 6.13 (s, 1H), 4.18-4.05 (m, 1H), 3.94 (s, 3H), 2.97-2.80 (m, 4H), 1.17 (d, J = 6.6 Hz, 6H), 0.85-0.73 (m, 2H), 0.59-0.47 (m, 2H). |
| 10 | ¹H NMR (500 MHz, DMSO-d₆) δ 8.89 (s, 1H), 8.63 (d, J = 3.7 Hz, 1H), 8.20 (s, 1H), 8.12 (s, 1H), 7.81 (s, 1H), 7.44-7.34 (m, 1H), 5.97 (s, 1H), 3.93 (s, 3H), 2.90 (td, J = 7.2, 3.4 Hz, 1H), 2.86 (d, J = 4.9 Hz, 3H), 0.86-0.72 (m, 2H), 0.57-0.48 (m, 2H). |
| 11 | ¹H NMR (500 MHz, DMSO-d₆) δ 10.30(s, 1H), 8.76(s, 1H), 8.65 (d, J = 3.1 Hz, 1H), 8.57 (s, 1H), 8.27 (s, 1H), 8.10 (dd, J = 8.5, 2.4 Hz, 1H), 7.83 (s, 1H), 7.39 (d, J = 4.3 Hz, 1H), 6.82 (d, J = 8.5 Hz, 1H), 6.07 (s, 1H), 4.01 (s, 3H), 3.83 (s, 3H), 2.96-2.82 (m, 4H), 0.79 (d, J = 5.5 Hz, 2H), 0.53 (br. s., 2H). |
| 12 | ¹H NMR (500 MHz, DMSO-d₆) δ 10.07 (s, 1H), 8.82(s, 1H), 8.65 (d, J = 3.7 Hz, 1H), 8.24 (s, 1H), 7.82 (s, 1H), 7.73 (d, J = 8.5 Hz, 2H), 7.39 (d, J = 4.9 Hz, 1H), 6.90 (d, J = 9.2 Hz, 2H), 6.06 (s, 1H), 4.00 (s, 3H), 3.74 (s, 3H), 2.91 (td, J = 7.3, 3.7 Hz, 1H), 2.87 (d, J = 4.9 Hz, 3H), 0.88-0.72 (m, 2H), 0.60-0.47 (m, 2H). |
| 13 | ¹H NMR (500 MHz, DMSO-d₆) δ 10.11 (s, 1H), 8.78 (s, 1H), 8.65 (d, J = 3.7 Hz, 1H), 8.24 (s, 1H), 7.82 (s, 1H), 7.49 (d, J = 1.8 Hz, 1H), 7.39 (d, J = 4.9 Hz, 1H), 7.29 (dd, J = 8.5, 2.4 Hz, 1H), 6.87 (d, J = 8.5 Hz, 1H), 6.06 (s, 1H), 5.99 (s, 2H), 4.00 (s, 3H), 2.96-2.82 (m, 4H), 0.84-0.72 (m, 2H), 0.59-0.46 (m, 2H). |
| 14 | ¹H NMR (500 MHz, DMSO-d₆) δ 8.91 (s, 1H), 8.67 (d, J = 3.1 Hz, 1H), 8.22 (d, J = 4.9 Hz, 1H), 8.08 (s, 1H), 7.87 (s, 1H), 7.42 (d, J = 4.9 Hz, 1H), 5.99 (s, 1H), 5.01-4.76 (m, 1H), 3.90 (s, 3H), 2.97 (d, J = 4.3 Hz, 1H), 2.87 (d, J = 4.9 Hz, 3H), 2.76 (d, J = 4.9 Hz, 3H), 1.29-1.16 (m, 1H), 1.04-0.90 (m, 1H). |
| 15 | ¹H NMR (500 MHz, DMSO-d₆) δ 10.14(s, 1H), 8.81 (s, 1H), 8.72(d, J = 3.7 Hz, 1H), 8.20 (s, 1H), 7.89 (s, 1H), 7.82 (d, J = 7.9 Hz, 2H), 7.41 (d, J = 4.9 |

| Compound | ¹H NMR |
|---|---|
| | Hz, 1H), 7.34 (t, J = 7.9 Hz, 2H), 7.10 (t, J = 7.3 Hz, 1H), 6.09 (s, 1H), 5.00-4.80 (m, 1H), 3.99 (s, 3H), 2.98 (d, J = 4.3 Hz, 1H), 2.89 (d, J = 4.9 Hz, 3H), 1.32-1.19 (m, 1H), 1.06-0.88 (m, 1H). |
| 16 | ¹H NMR (500 MHz, DMSO-$d_6$) δ 8.90 (s, 1H), 8.64 (br. s., 1H), 8.32 (d, J = 3.7 Hz, 1H), 8.13 (s, 1H), 7.82 (s, 1H), 7.39 (d, J = 4.4 Hz, 1H), 5.99 (s, 1H), 3.92 (s, 3H), 2.95-2.78 (m, 5H), 0.78 (d, J = 5.4 Hz, 2H), 0.70-0.56 (m, 4H), 0.52 (br. s., 2H). |
| 17 | ¹H NMR (500 MHz, DMSO-$d_6$) δ 8.91 (s, 1H), 8.64 (d, J = 3.0 Hz, 1H), 8.26 (t, J = 6.1 Hz, 1H), 8.14 (s, 1H), 7.81 (s, 1H), 7.38 (d, J = 4.7 Hz, 1H), 5.99 (s, 1H), 3.94 (s, 3H), 3.07 (t, J = 6.6 Hz, 2H), 2.96-2.81 (m, 4H), 1.85 (dt, J = 13.5, 6.7 Hz, 1H), 0.86 (d, J = 6.4 Hz, 6H), 0.79 (d, J = 5.4 Hz, 2H), 0.54 (br. s., 2H) |
| 18 | ¹H NMR (500 MHz, DMSO-$d_6$) δ 9.33 (br. s., 1H), 8.82 (s, 1H), 8.63 (d, J = 3.0 Hz, 1H), 8.46 (t, J = 5.9 Hz, 1H), 8.19 (s, 1H), 7.83 (s, 1H), 5.97 (s, 1H), 3.95 (s, 2H), 3.07 (br. s., 2H), 2.86 (d, J = 4.4 Hz, 2H), 2.77 (d, J = 4.7 Hz, 5H), 2.53 (s, 3H), 2.51 (s, 3H), 1.95-1.78 (m, 2H), 0.79 (d, J = 5.4 Hz, 2H), 0.52 (br. s., 2H). |
| 19 | ¹H NMR (500 MHz, DMSO-$d_6$) δ 8.86 (s, 1H), 8.65 (d, J = 3.1 Hz, 1H), 8.47 (d, J = 7.9 Hz, 1H), 8.16 (s, 1H), 7.82 (s, 1H), 7.39 (d, J = 4.9 Hz, 1H), 6.00 (s, 1H), 4.50-4.36 (m, 1H), 3.95 (s, 3H), 2.99-2.82 (m, 4H), 2.23-2.09 (m, 4H), 1.73-1.55 (m, 2H), 0.88-0.69 (m, 2H), 0.58-0.47 (m, 2H). |
| 20 | ¹H NMR (500 MHz, DMSO-$d_6$) δ 8.90 (s, 1H), 8.64 (d, J = 3.0 Hz, 1H), 8.28 (t, J = 5.7 Hz, 1H), 8.13 (s, 1H), 7.81 (s, 1H), 7.38 (d, J = 4.7 Hz, 1H), 5.98 (s, 1H), 3.93 (s, 3H), 3.27 (t, J = 6.6 Hz, 2H), 2.97-2.83 (m, 4H), 1.10 (t, J = 7.1 Hz, 3H), 0.79 (d, J = 5.4 Hz, 2H), 0.53 (br. s., 2H). |
| 21 | ¹H NMR (500 MHz, DMSO-$d_6$) δ 10.43 (s, 1H), 8.76(s, 1H), 8.66(d, J = 3.0 Hz, 1H), 8.30 (s, 1H), 7.88-7.78 (m, 2H), 7.67 (d, J = 8.1 Hz, 1H), 7.47-7.32 (m, 2H), 6.93 (td, J = 8.4, 2.0 Hz, 1H), 6.11 (s, 1H), 4.03 (s, 3H), 3.00-2.81 (m, 4H), 0.89-0.71 (m, 2H), 0.62-0.42 (m, 2H). |
| 22 | ¹H NMR (500 MHz, DMSO-$d_6$) δ10.06(s, 1H), 8.81 (s, 1H), 8.66(d, J = 3.7 Hz, 1H), 8.27 (s, 1H), 7.84 (s, 1H), 7.75 (s, 1H), 7.58 (d, J = 8.5 Hz, 1H), 7.40 (d, J = 4.9 Hz, 1H), 7.22 (t, J = 7.6 Hz, 1H), 6.92 (d, J = 7.3 Hz, 1H), 6.10 (s, 1H), 4.02 (s, 3H), 2.95-2.82 (m, 4H), 2.31 (s, 3H), 0.85-0.76 (m, 2H), 0.60-0.48 (m, 2H). |
| 23 | ¹H NMR (500 MHz, DMSO-$d_6$) δ 10.30(s, 1H), 8.79(s, 1H), 8.66(d, J = 3.4 Hz, 1H), 8.28 (s, 1H), 7.92-7.74 (m, 3H), 7.41 (d, J = 4.7 Hz, 1H), 7.19 (t, J = 8.8 Hz, 2H), 6.08 (s, 1H), 4.02 (s, 3H), 2.98-2.80 (m, 4H), 0.87-0.71 (m, 2H), 0.63-0.43 (m, 2H). |
| 24 | ¹H NMR (500 MHz, DMSO-$d_6$) δ 10.51 (s, 1H), 9.30 (s, 1H), 8.82 (s, 1H), 8.72 (s, 1H), 8.67 (d, J = 3.0 Hz, 1H), 8.29 (s, 1H), 8.05 (d, J = 8.8 Hz, 1H), 7.94 (d, J = 8.8 Hz, 1H), 7.84 (s, 1H), 7.41 (d, J = 4.7 Hz, 1H), 6.07 (s, 1H), 4.04 (s, 3H), 3.00-2.80 (m, 4H), 0.81 (d, J = 5.7 Hz, 2H), 0.55 (br. s., 2H). |
| 25 | ¹H NMR (500 MHz, DMSO-$d_6$) δ 9.73 (br. s., 1H), 8.72 (br. s., 1H), 8.66 (br. s., 1H), 8.28 (br. s., 1H), 7.84 (br. s., 2H), 7.47-7.18 (m, 4H), 6.06 (br. s., 1H), 4.02 (br. s., 3H), 2.88 (d, J = 14.0 Hz, 4H), 0.80 (br. s., 2H), 0.53 (br. s., 2H). |
| 26 | ¹H NMR (500 MHz, DMSO-$d_6$) δ 10.46 (s, 1H), 9.24 (s, 1H), 8.79 (s, 1H), 8.67 (d, J = 3.7 Hz, 1H), 8.31 (s, 1H), 8.23 (s, 1H), 8.05 (d, J = 9.2 Hz, 2H), 7.87-7.80 (m, 3H), 7.41 (d, J = 4.9 Hz, 1H), 6.11 (s, 1H), 4.04 (s, 3H), 2.95-2.81 (m, 4H), 0.81 (d, J = 4.9 Hz, 2H), 0.54 (br. s., 2H). |
| 27 | ¹H NMR (500 MHz, DMSO-$d_6$) δ 10.00 (br. s., 1H), 8.85 (s, 1H), 8.67 (d, J = 3.4 Hz, 1H), 8.26 (s, 1H), 7.85 (s, 1H), 7.71 (d, J = 8.4 Hz, 2H), 6.89 (br. s., 2H), 6.08 (s, 1H), 4.01 (s, 3H), 2.93 (s, 6H), 2.88 (d, J = 4.0 Hz, 4H), 0.87-0.74 (m, 2H), 0.60-0.48 (m, 2H) one exchangeable proton missing. |

Example 28

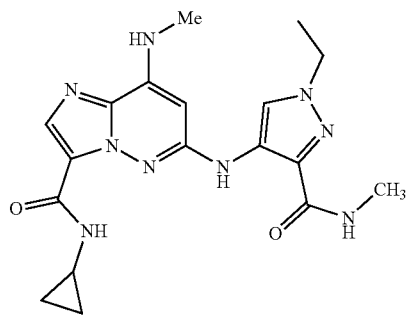

Example 28

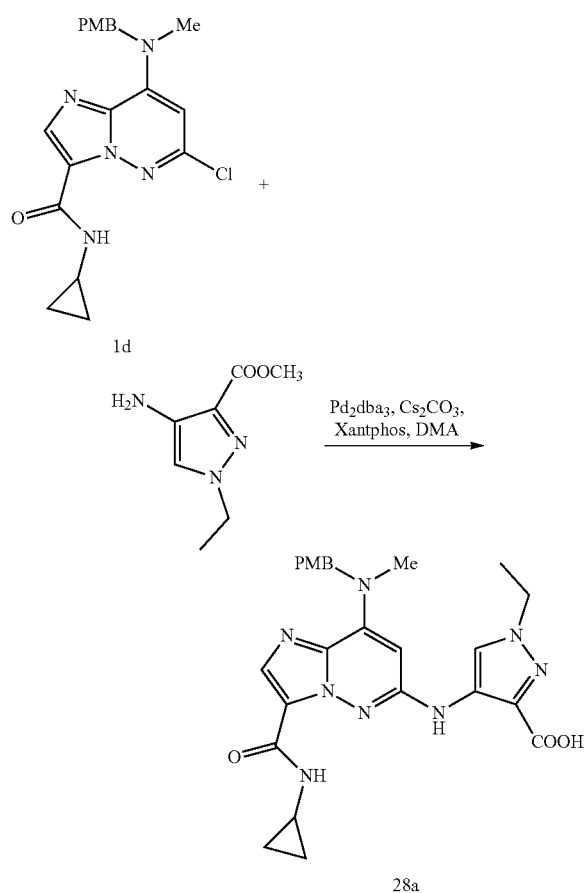

A mixture of 6-chloro-N-cyclopropyl-8-((4-methoxybenzyl)(methyl) amino)imidazo[1,2-b]pyridazine-3-carboxamide (1d) (125 mg, 0.324 mmol), methyl 4-amino-1-ethyl-1H-pyrazole-3-carboxylate [Free based (sodium bicarbonate solution/EtOAc) from HCl salt purchased from Princeton BioMolecular Research] (110 mg, 0.648 mmol), Pd2(dba)3 (29.7 mg, 0.032 mmol), XANTPHOS (37.5 mg, 0.065 mmol) and Cs2CO3 (422 mg, 1.296 mmol) in DMA (2 mL) was degassed by bubbling N$_2$ through the mixture for 5 minutes. The reaction vessel was sealed and heated to 125° C. for 8 hr. After cooling to rt, the reaction mixture was partitioned between EtOAc (30 ml) and water (20 ml). The organic layer was extracted with 1N NaOH (10 ml) and the combined aqueous layers were washed with EtOAc (20 ml). The aqueous layer was acidified to pH 1 with 1N HCl and the mixture was transferred to a separatory funnel and the aqueous layer was extracted with EtOAc (3×25 ml). The combined organic layers were washed with 10% LiCl solution (2×50 ml) and brine (50 ml). After drying (Na$_2$SO$_4$) and filtration the organic layer was concentrated to afford 4-((3-(cyclopropylcarbamoyl)-8-((4-methoxybenzyl)(methyl) amino)imidazo[1,2-b]pyridazin-6-yl)amino)-1-ethyl-1H-pyrazole-3-carboxylic acid (125 mg, 0.248 mmol, 76% yield) as a tan solid. LC retention time 2.67 min [C]. MS (E+) m/z: 505 (MH$^+$).

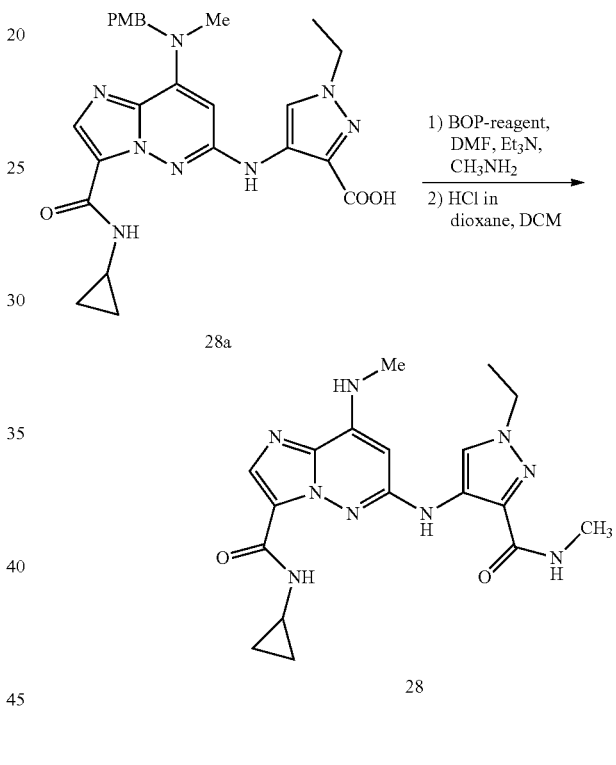

Example 28

A mixture of 4-((3-(cyclopropylcarbamoyl)-8-((4-methoxybenzyl)(methyl) amino)imidazo[1,2-b]pyridazin-6-yl)amino)-1-ethyl-1H-pyrazole-3-carboxylic acid (12 mg, 0.024 mmol), methanamine, 2M in THF (0.059 mL, 0.119 mmol), BOP (13.67 mg, 0.031 mmol) and triethylamine (9.95 µl, 0.071 mmol) in DMF (0.25 mL) was allowed to stand at rt for 1 hr. The volatiles were removed in vacuo to afford a yellow oil that was treated with HCl, 4N in dioxane (0.058 mL, 0.232 mmol) in DCM (0.2 mL) and was allowed to stand at rt for 1 hr. The reaction mixture was concentrated and the residue was purified via preparative LC/MS with the following conditions: Column: Waters XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 5-100% B over 15 minutes, then a 5-minute hold at 100% B; Flow: 20 mL/min. Fractions containing the desired product were combined and dried via centrifugal evaporation to afford N-cyclopropyl-6-((1-ethyl-3-(methylcarbamoyl)-1H-pyrazol-4-yl)amino)-8-(methylamino)imidazo[1,2-b]pyridazine-3-carboxamide (28) (5.8 mg, 0.015 mmol, 63% yield). LC retention time 1.04 min [D]. MS (E+) m/z: 398 (MH+). $^1$H NMR (500 MHz, DMSO-$d_6$) δ 8.90 (s, 1H), 8.60 (d, J=3.1 Hz, 1H), 8.24 (s, 1H), 8.18 (d, J=4.9 Hz, 1H), 7.81 (s, 1H), 7.37 (d, J=4.9 Hz, 1H), 5.97 (s, 1H), 4.20 (q, J=7.3 Hz, 2H), 2.93-2.83 (m, 4H), 2.77 (d, J=4.3 Hz, 3H), 1.47 (t, J=7.3 Hz, 3H), 0.81-0.70 (m, 2H), 0.58-0.47 (m, 2H).

The following Examples were prepared in a similar manner to Example 28

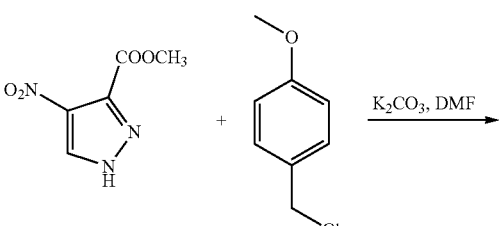

| Example number | R² | R⁴ | Rt (min) [Method] | m/z [M + H]⁺ |
|---|---|---|---|---|
| 29 | cyclopropyl | pyrimidinyl | 1.11 [D] | 462 |
| 30 | cyclopropyl | pyridyl | 0.93 [D] | 461 |
| 31 | cyclopropyl | phenyl | 1.59 [D] | 460 |

| Compound | $^1$H NMR |
|---|---|
| 29 | $^1$H NMR (500 MHz, DMSO-$d_6$) δ 10.65 (s, 1H), 9.24 (s, 2H), 8.91 (s, 1H), 8.71 (s, 1H), 8.59 (br. s., 1H), 8.48 (s, 1H), 7.83 (s, 1H), 7.39 (d, J = 4.3 Hz, 1H), 6.12 (s, 1H), 4.31 (q, J = 7.1 Hz, 2H), 2.87 (d, J = 4.9 Hz, 4H), 1.54 (t, J = 7.3 Hz, 3H), 0.77 (d, J = 5.5 Hz, 2H), 0.53 (br. s., 2H). |
| 30 | $^1$H NMR (500 MHz, DMSO-$d_6$) δ 10.47 (s, 1H), 9.06 (d, J = 1.8 Hz, 1H), 8.75 (s, 1H), 8.59 (d, J = 3.7 Hz, 1H), 8.45 (s, 1H), 8.33 (d, J = 4.3 Hz, 1H), 8.28 (d, J = 8.5 Hz, 1H), 7.83 (s, 1H), 7.45 (dd, J = 8.2, 4.6 Hz, 1H), 7.39 (d, J = 4.9 Hz, 1H), 6.09 (s, 1H), 4.30 (q, J = 6.9 Hz, 2H), 2.94-2.80 (m, 4H), 1.54 (t, J = 7.3 Hz, 3H), 0.83-0.70 (m, 2H), 0.57-0.45 (m, 2H). |
| 31 | $^1$H NMR (500 MHz, DMSO-$d_6$) δ 10.09 (s, 1H), 8.81 (s, 1H), 8.60 (d, J = 3.1 Hz, 1H), 8.40 (s, 1H), 7.88-7.76 (m, 2H), 7.45-7.25 (m, 3H), 7.09 (t, J = 7.3 Hz, 1H), 6.55 (s, 1H), 6.07 (s, 1H), 4.28 (q, J = 7.3 Hz, 2H), 2.94-2.81 (m, 4H), 1.53 (t, J = 7.3 Hz, 3H), 0.84-0.72 (m, 2H), 0.54 (d, J = 2.4 Hz, 2H). |

Example 32

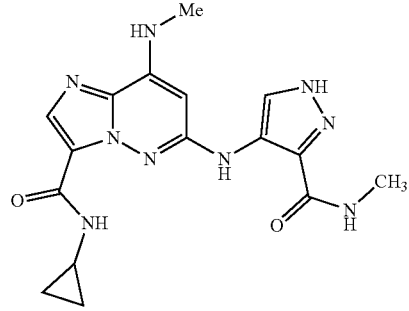

32a

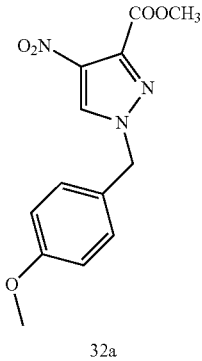

32a

A mixture of methyl 4-nitro-1H-pyrazole-3-carboxylate (commercially available from CombiBlocks) (342 mg, 1.999 mmol), potassium carbonate (552 mg, 4.00 mmol) and 4-methoxybenzyl chloride (0.299 mL, 2.199 mmol) in DMF (10 mL) was stirred for 18 hr. The reaction mixture was partitioned between EtOAc (40 ml) and water (40 ml). The organic layer was washed with 10% LiCl solution (2×40 ml) and brine (25 ml). After drying (Na$_2$SO$_4$) and filtration the organic layer was concentrated to a yellow oil that was chromatographed on a 40 gm ISCO silica gel cartridge, eluting with a 0-50% EtOAc/Hex gradient. The pure fractions were concentrated to afford methyl 1-(4-methoxybenzyl)-4-nitro-1H-pyrazole-3-carboxylate (32a) (481 mg, 1.651 mmol, 83% yield) as a colorless oil. LC retention time 1.96 min [C]. MS (E+) m/z: 292 (MH$^+$). $^1$H NMR (400 MHz, CHLOROFORM-d) δ 7.95 (s, 1H), 7.42-7.18 (m, 2H), 6.94 (d, J=8.8 Hz, 2H), 5.27 (s, 2H), 3.99 (s, 3H), 3.83 (s, 3H).

32b

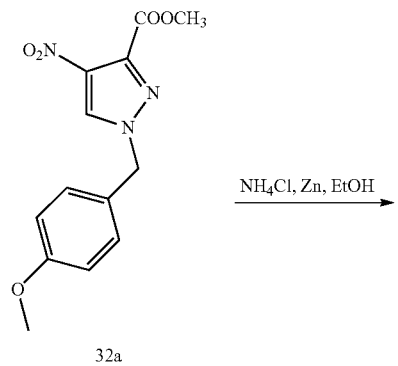

32a

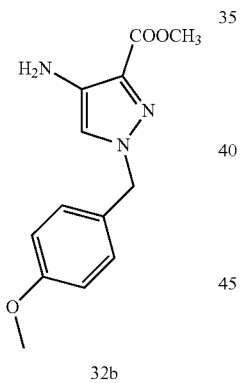

32b

To a mixture of methyl 1-(4-methoxybenzyl)-4-nitro-1H-pyrazole-3-carboxylate (475 mg, 1.631 mmol) and ammonium chloride (32a) (872 mg, 16.31 mmol) in EtOH (12 mL) and water (2 mL) at rt was added zinc (1066 mg, 16.31 mmol) and the resulting mixture was stirred at rt for 30 minutes. The reaction was then diluted with dichloromethane (50 ml), and filtered. The filtrate was washed with water (50 ml), dried (Na$_2$SO$_4$), and concentrated to afford methyl 4-amino-1-(4-methoxybenzyl)-1H-pyrazole-3-carboxylate (32b) (425 mg, 1.627 mmol, 100% yield) as a thick colorless oil. LC retention time 0.89 min [C]. MS (E+) m/z: 262 (MH$^+$). $^1$H NMR (400 MHz, CHLOROFORM-d) δ 7.19 (d, J=8.8 Hz, 2H), 6.87 (d, J=8.8 Hz, 2H), 6.84 (s, 1H), 5.18 (s, 2H), 4.05 (br. s., 2H), 3.93 (s, 3H), 3.80 (s, 3H).

32c

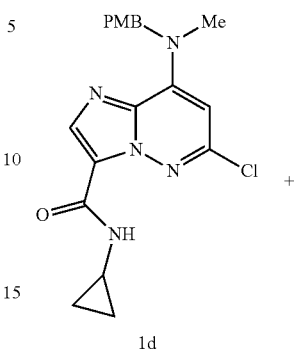

1d

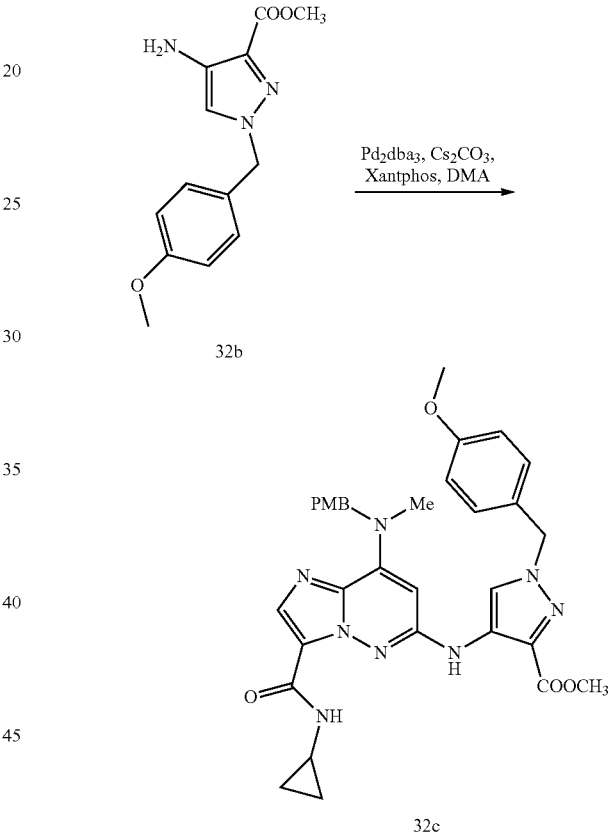

32c

A mixture of 6-chloro-N-cyclopropyl-8-((4-methoxybenzyl)(methyl) amino)imidazo[1,2-b]pyridazine-3-carboxamide (32b) (200 mg, 0.518 mmol), methyl 4-amino-1-(4-methoxybenzyl)-1H-pyrazole-3-carboxylate (203 mg, 0.778 mmol), Pd2(dba)3 (47.5 mg, 0.052 mmol), XANTPHOS (60.0 mg, 0.104 mmol) and Cs2CO3 (676 mg, 2.073 mmol) in DMA (3 mL) was degassed by bubbling N$_2$ through the mixture for 5 minutes. The reaction vessel was sealed and heated to 125° C. for 4 hr. After cooling to rt, the reaction mixture was partitioned between EtOAc (30 ml) and water (30 ml). The organic layer was washed with 10% LiCl (2×30 ml) and brine (30 ml). After drying (Na$_2$SO$_4$) and filtration, the organic layer was concentrated to an amber oil that was chromatographed on a 24 gm ISCO silica gel cartridge, eluting with a 0-100% EtOAc/Hex gradient. The pure fractions were concentrated to afford methyl 4-((3-(cyclopropylcarbamoyl)-8-((4-methoxybenzyl)(methyl)amino)imidazo

[1,2-b]pyridazin-6-yl)amino)-1-(4-methoxybenzyl)-1H-pyrazole-3-carboxylate (32c) (310 mg, 0.508 mmol, 98% yield) as a tan foam. LC retention time 3.30 min [C]. MS (E+) m/z: 611 (MH+).

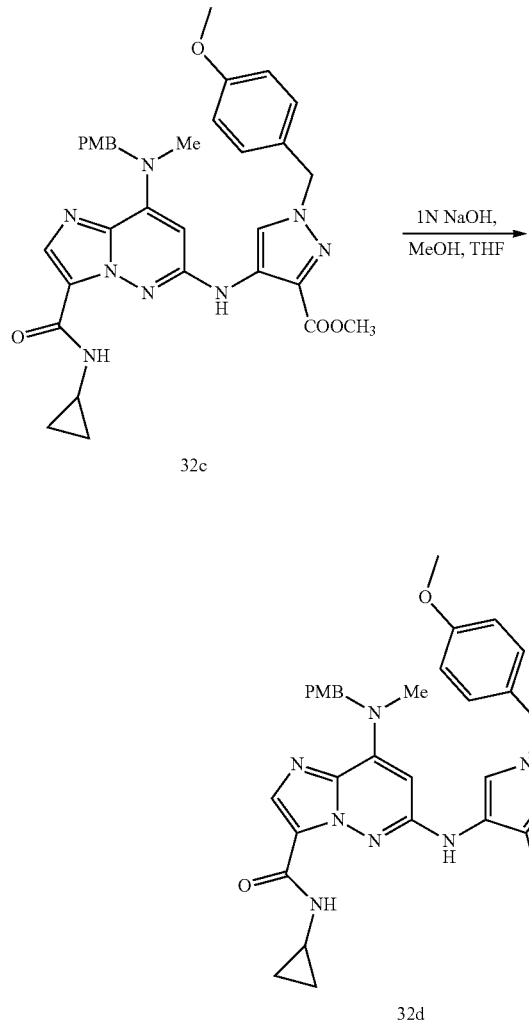

A mixture of methyl 4-((3-(cyclopropylcarbamoyl)-8-((4-methoxybenzyl) (methyl)amino)imidazo[1,2-b]pyridazin-6-yl)amino)-1-(4-methoxybenzyl)-1H-pyrazole-3-carboxylate (32c) (290 mg, 0.475 mmol) and NaOH, 1N (2.374 mL, 2.374 mmol) in MeOH (3 mL) and THF (3 mL) was allowed to stir at rt for 1 hr. The organic solvents were removed in vacuo and the residue was diluted with water. The aqueous layer was acidified to pH 1 with 1N HCl and the heterogeneous layer was transferred to a separatory funnel and was extracted with EtOAc (40 ml). The organic layer was washed with brine (25 ml) and was dried (Na₂SO₄) and concentrated to afford 4-((3-(cyclopropylcarbamoyl)-8-((4-methoxybenzyl)(methyl)amino)imidazo[1,2-b]pyridazin-6-yl)amino)-1-(4-methoxybenzyl)-1H-pyrazole-3-carboxylic acid (32d) (248 mg, 0.416 mmol, 88% yield) as a tan solid. LC retention time 3.15 min [C]. MS (E+) m/z: 597 (MH+).

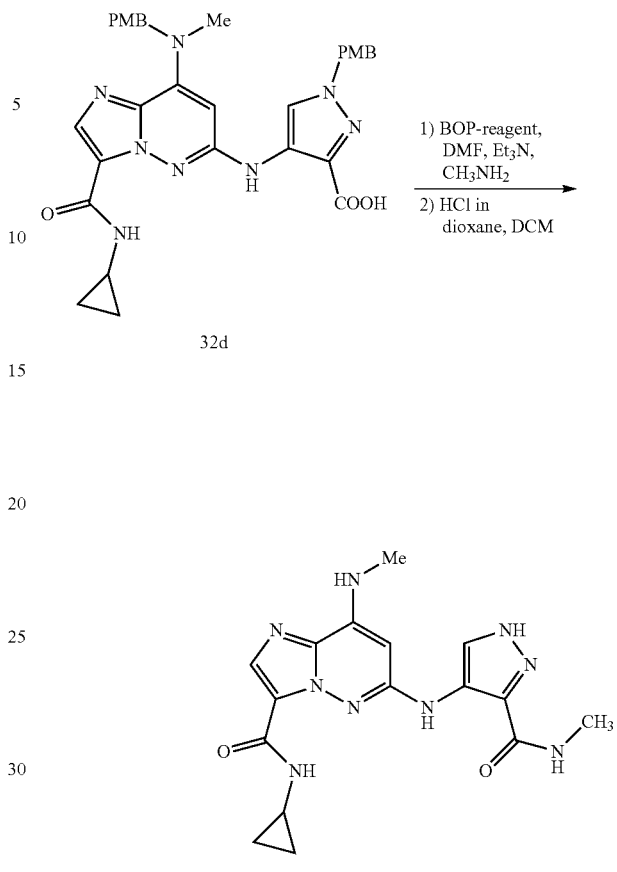

Example 32

A mixture of 4-((3-(cyclopropylcarbamoyl)-8-((4-methoxybenzyl) (methyl)amino)imidazo[1,2-b]pyridazin-6-yl)amino)-1-(4-methoxybenzyl)-1H-pyrazole-3-carboxylic acid (32d) (18 mg, 0.030 triethylamine (0.017 mL, 0.121 mmol) in DMF (0.25 mL) was agitated at rt for 2 hr. The volatiles were removed in vacuo to afford a yellow oil that was treated with TFA (0.5 mL) at 75° C. for 2 hr. The volatiles were removed in vacuo and the residue was purified via preparative LC/MS with the following conditions: Column: Waters XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 0-100% B over 20 minutes, then a 0-minute hold at 100% B; Flow: 20 mL/min. Fractions containing the desired product were combined and dried via centrifugal evaporation to afford N-cyclopropyl-6-((3-(methylcarbamoyl)-1H-pyrazol-4-yl) amino)-8-(methylamino)imidazo[1,2-b]pyridazine-3-carboxamide (32) (7.2 mg, 0.019 mmol, 64% yield). LC retention time 0.82 min [D]. MS (E+) m/z: 370 (MH+). ¹H NMR (500 MHz, DMSO-d₆) δ 13.28 (br. s., 1H), 8.85 (s, 1H), 8.61 (d, J=3.1 Hz, 1H), 8.30-8.17 (m, 2H), 7.82 (s, 1H), 7.32 (d, J=5.5 Hz, 1H), 5.97 (s, 1H), 2.92-2.82 (m, 4H), 2.78 (d, J=4.9 Hz, 3H), 0.77 (d, J=6.1 Hz, 2H), 0.52 (br. s., 2H).

The following Examples were prepared in a similar manner to Example 32

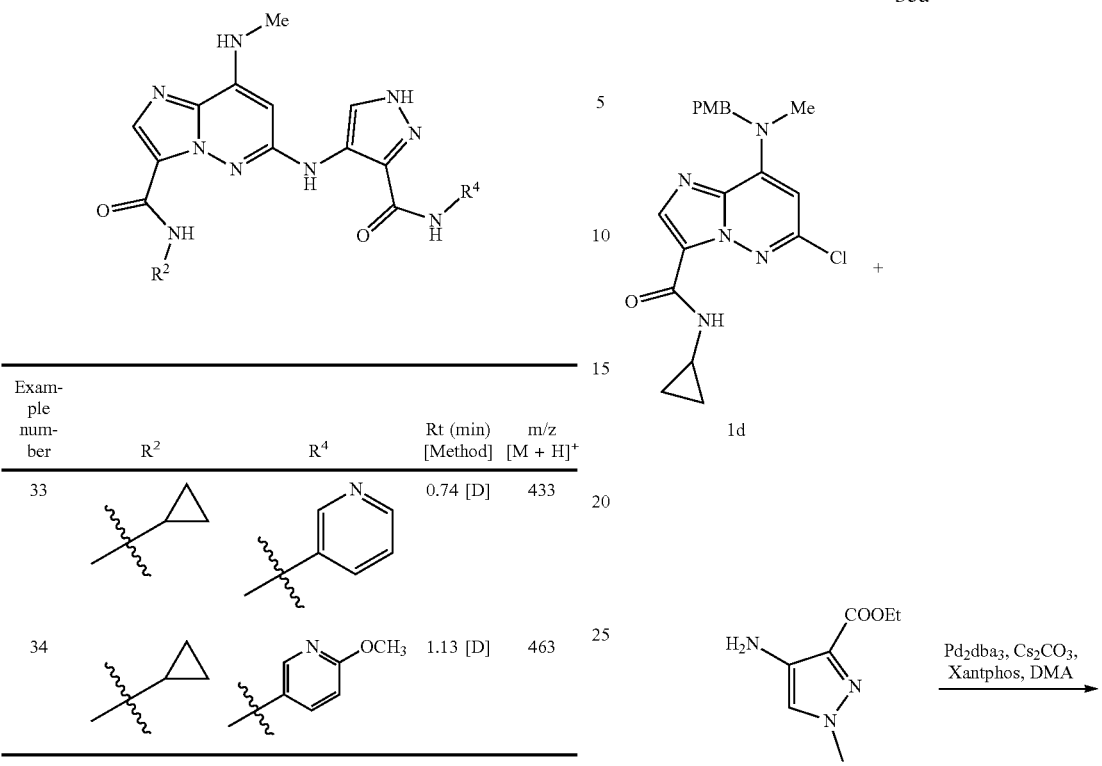

| Example number | R² | R⁴ | Rt (min) [Method] | m/z [M + H]⁺ |
|---|---|---|---|---|
| 33 | cyclopropyl | pyridin-3-yl | 0.74 [D] | 433 |
| 34 | cyclopropyl | 6-methoxypyridin-3-yl | 1.13 [D] | 463 |

| Compound | ¹H NMR |
|---|---|
| 33 | ¹H NMR (500 MHz, DMSO-d₆) δ 13.61 (br. s., 1H), 10.52 (br. s., 1H), 8.69 (s, 1H), 8.62 (br. s., 1H), 8.39 (br. s., 1H), 8.27 (d, J = 7.9 Hz, 1H), 7.83 (s, 1H), 7.47 (br. s., 1H), 7.33 (d, J = 3.7 Hz, 1H), 6.07 (s, 1H), 2.87 (d, J = 4.3 Hz, 4H), 0.77 (d, J = 6.1 Hz, 2H), 0.52 (br. s., 2H) 2 exchangeable protons missing. |
| 34 | ¹H NMR (500 MHz, DMSO-d₆) δ 13.53 (br. s., 1H), 10.29 (br. s., 1H), 8.73 (br. s., 1H), 8.68-8.51 (m, 2H), 8.39 (br. s., 1H), 8.09 (d, J = 8.5 Hz, 1H), 7.83 (s, 1H), 7.34 (br. s., 1H), 6.83 (d, J = 9.2 Hz, 1H), 6.06 (s, 1H), 3.83 (s, 3H), 2.87 (d, J = 4.3 Hz, 4H), 0.77 (d, J = 6.1 Hz, 2H), 0.53 (br. s., 2H). |

Example 35

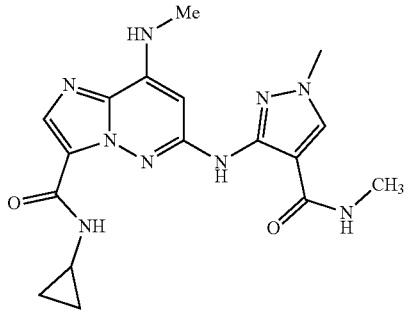

Example 35

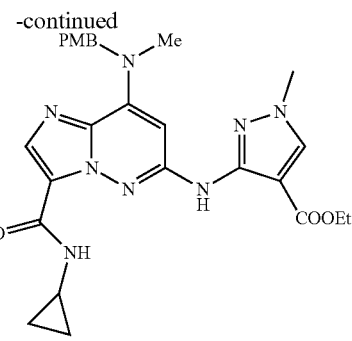

A mixture of 6-chloro-N-cyclopropyl-8-((4-methoxybenzyl)(methyl) amino)imidazo[1,2-b]pyridazine-3-carboxamide (1d) (125 mg, 0.324 mmol), ethyl 3-amino-1-methyl-1H-pyrazole-4-carboxylate (commercially available from J and W Chemicals) (82 mg, 0.486 mmol), Pd2(dba)3 (29.7 mg, 0.032 mmol), XANTPHOS (37.5 mg, 0.065 mmol) and Cs2CO₃ (422 mg, 1.296 mmol) in DMA (2 mL) was degassed by bubbling N₂ through the mixture for 5 minutes. The reaction vessel was sealed and heated to 125° C. for 1 hr. After cooling to rt, the reaction mixture was partitioned between EtOAc (50 ml) and water (50 ml). The organic layer was washed with 10% LiCl (2×50 ml) and brine (50 ml). After drying (MgSO₄) and filtration, the organic layer was concentrated to an amber oil that was chromatographed on a 12 gm ISCO silica gel cartridge, eluting with a 0-100% EtOAc/Hex gradient. The pure fractions were concentrated to afford ethyl 3-((3-(cyclopropylcarbamoyl)-8-((4-methoxybenzyl) (methyl)amino)imidazo[1,2-b]pyridazin-6-yl)amino)-1-methyl-1H-pyrazole-4-carboxylate (35a) (152 mg, 0.293 mmol, 90% yield) as a light yellow solid. LC retention time 3.16 min [C]. MS (E+) m/z: 519 (MH⁺).

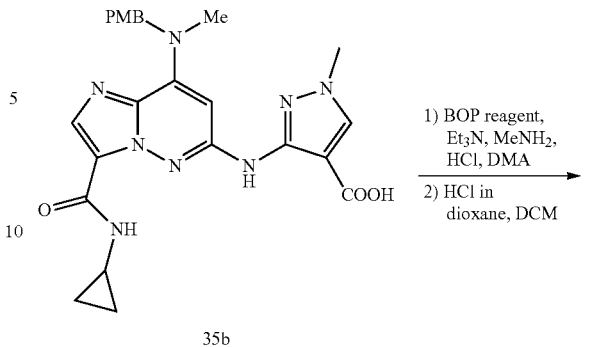

35b

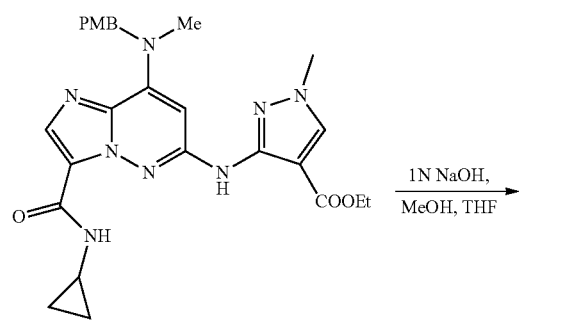

35a

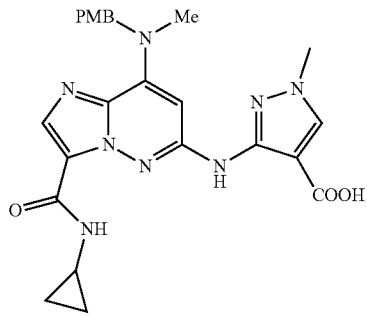

35b

A mixture of ethyl 3-((3-(cyclopropylcarbamoyl)-8-((4-methoxybenzyl) (methyl)amino)imidazo[1,2-b]pyridazin-6-yl)amino)-1-methyl-1H-pyrazole-4-carboxylate (35a) (140 mg, 0.270 mmol) and NaOH, 1N (1.350 mL, 1.350 mmol) in MeOH (1.5 mL) and THF (1.5 mL) was stirred at rt for 2 hr. The organic solvents were removed in vacuo and the residue was diluted with water. The aqueous layer was acidified to pH 1 with 1N HCl and the heterogeneous layer was transferred to a separatory funnel and was extracted with DCM (25 ml), CHCl₃ (25 ml) and EtOAc (25 ml). The organic layer was dried (Na₂SO₄) and concentrated to afford 3-((3-(cyclopropylcarbamoyl)-8-((4-methoxybenzyl) (methyl)amino)imidazo[1,2-b]pyridazin-6-yl)amino)-1-methyl-1H-pyrazole-4-carboxylic acid (35b) (130 mg, 0.265 mmol, 98% yield) as a light yellow solid. LC retention time 3.01 min [C]. MS (E+) m/z: 491 (MH⁺).

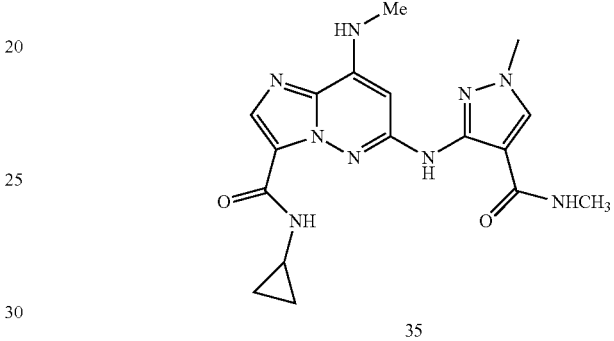

35

Example 35

A mixture of 3-((3-(cyclopropylcarbamoyl)-8-((4-methoxybenzyl) (methyl)amino)imidazo[1,2-b]pyridazin-6-yl)amino)-1-methyl-1H-pyrazole-4-carboxylic acid (35b) (15 mg, 0.031 mmol), methanamine, HCl (4.13 mg, 0.061 mmol), BOP (17.58 mg, 0.040 mmol) and Et₃N (0.021 mL, 0.153 mmol) in DMF (0.25 mL) was agitated at rt for 18 hr at rt. The volatiles were removed in vacuo to afford a yellow oil that was treated with HCl, 4N in dioxane (0.079 mL, 0.232 mmol) in DCM (1 mL) and was allowed to stand at rt for 1 hr. The reaction mixture was concentrated and the residue was purified via preparative LC/MS with the following conditions: Column: Waters XBridge C18, 19×250 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 0-100% B over 25 minutes, then a 5-minute hold at 100% B; Flow: 20 mL/min. Fractions containing the desired product were combined and dried via centrifugal evaporation to afford N-cyclopropyl-6-((1-methyl-4-(methylcarbamoyl)-1H-pyrazol-3-yl)amino)-8-(methylamino) imidazo[1,2-b]pyridazine-3-carboxamide (35) (5.9 mg, 0.015 mmol, 47% yield). LC retention time 0.89 min [D]. MS (E+) m/z: 384 (MH⁺). ¹H NMR (500 MHz, DMSO-d₆) δ 9.78 (s, 1H), 9.51 (d, J=2.4 Hz, 1H), 8.17 (d, J=4.9 Hz, 1H), 8.11 (s, 1H), 7.83 (s, 1H), 7.52 (d, J=4.9 Hz, 1H), 6.17 (s, 1H), 3.96-3.85 (m, 3H), 2.89 (d, J=5.5 Hz, 3H), 2.80 (dd, J=6.7, 3.7 Hz, 1H), 2.75 (d, J=4.9 Hz, 3H), 0.91-0.77 (m, 2H), 0.64-0.54 (m, 2H).

Example 36

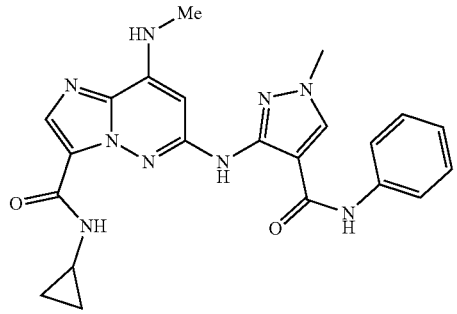

Example 36

Example 36 was prepared in a similar manner to Example 35: LC retention time 1.38 min [D]. MS (E+) m/z: 446 (MH+). $^1$H NMR (500 MHz, DMSO-$d_6$) δ 9.92 (br. s., 1H), 9.65-9.45 (m, 2H), 8.45 (s, 1H), 7.84 (s, 1H), 7.68 (d, J=7.3 Hz, 2H), 7.52 (br. s., 1H), 7.41-7.27 (m, 2H), 7.09 (br. s., 1H), 6.20 (s, 1H), 3.94 (s, 3H), 2.97-2.84 (m, 3H), 2.81 (br. s., 1H), 0.83 (d, J=4.9 Hz, 2H), 0.60 (br. s., 2H).

Example 37

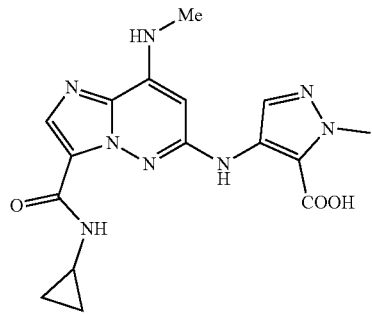

Example 37

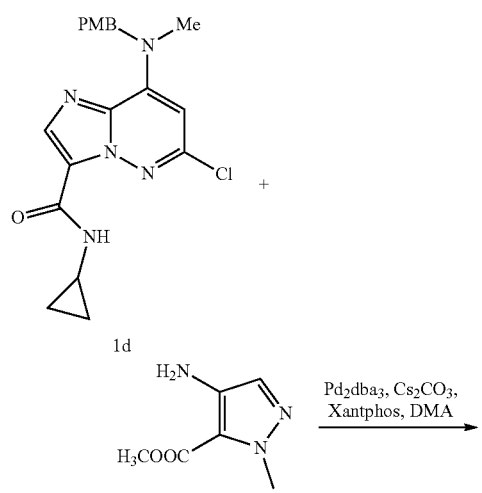

A mixture of 6-chloro-N-cyclopropyl-8-((4-methoxybenzyl)(methyl) amino)imidazo[1,2-b]pyridazine-3-carboxamide (1d) (100 mg, 0.259 mmol), methyl 4-amino-1-methyl-1H-pyrazole-5-carboxylate [Commercially available from ChemBridge](80 mg, 0.518 mmol), Pd$_2$(dba)3 (23.73 mg, 0.026 mmol), XANTPHOS (30.0 mg, 0.052 mmol) and Cs$_2$CO$_3$ (338 mg, 1.037 mmol) in DMA (2 mL) was degassed by bubbling N$_2$ through the mixture for 5 minutes. The reaction vessel was sealed and heated to 125° C. for 2 hr. After cooling to rt, water (5 ml), followed by 1N NaOH (1 ml) were added. After dilution with 10 ml of water, the mixture was transferred to a separatory funnel and was extracted with Et$_{20}$ (20 ml). The aqueous layer was acidified to ~pH 1 with 1N HCl. After extracting the aqueous with EtOAc (2×30 ml), the combined organics were washed with (10% LiCl solution (2×50 ml) and brine (50 ml). The organic layer was allowed to dry over Na$_2$SO$_4$ overnight. Concentration afforded 4-((3-(cyclopropylcarbamoyl)-8-((4-methoxybenzyl)(methyl)amino)imidazo[1,2-b]pyridazin-6-yl)amino)-1-methyl-1H-pyrazole-5-carboxylic acid (125 mg, 0.255 mmol, 98% yield) as a tan solid. LC retention time 2.79 min [C]. MS (E+) m/z: 491 (MH+).

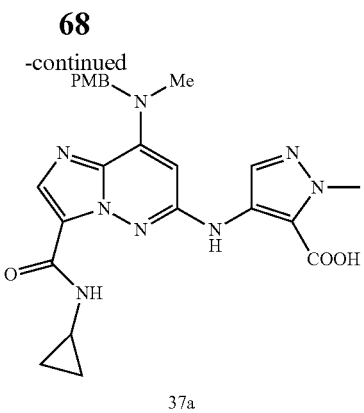

Example 37

A mixture of 4-((3-(cyclopropylcarbamoyl)-8-((4-methoxybenzyl)(methyl) amino)imidazo[1,2-b]pyridazin-6-yl)amino)-1-methyl-1H-pyrazole-5-carboxylic acid (18 mg, 0.037 mmol) and HCl, 4N in dioxane (0.183 mL, 0.734 mmol) in DCM were allowed to stand at rt for 1 hr. MeOH (1 ml) was added and the reaction mixture was concentrated to driness. The residue was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-75% B over 25 minutes, then a 5-minute hold at 75% B; Flow: 20 mL/min. Fractions containing the desired product were combined and dried via centrifugal evaporation to afford 4-((3-(cyclopropylcarbamoyl)-8-(methylamino)imidazo[1,2-b]pyridazin-6-yl)amino)-1-methyl-1H-pyrazole-5-carboxylic acid (7.8 mg, 0.021 mmol, 56% yield). LC retention time 0.88 min [D]. MS (E+) m/z: 371 (MH+). $^1$H NMR (500 MHz, DMSO-d$_6$) δ 8.58 (d, J=4.0 Hz, 1H), 8.35 (s, 1H), 7.92 (s, 1H), 7.81 (s, 1H), 7.43 (d, J=4.7 Hz, 1H), 6.04 (s, 1H), 4.07 (s, 3H), 2.93-2.82 (m, 4H), 0.78-0.66 (m, 2H), 0.56-0.46 (m, 2H) One exchangeable proton missing.

Example 38

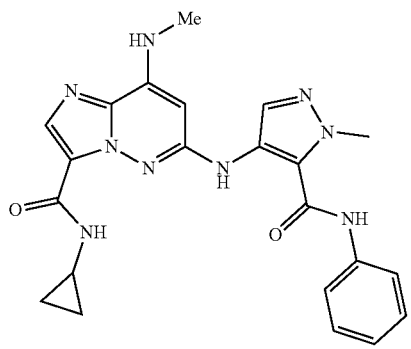

Example 38

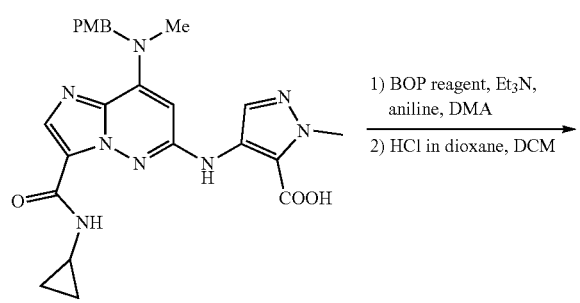

37a

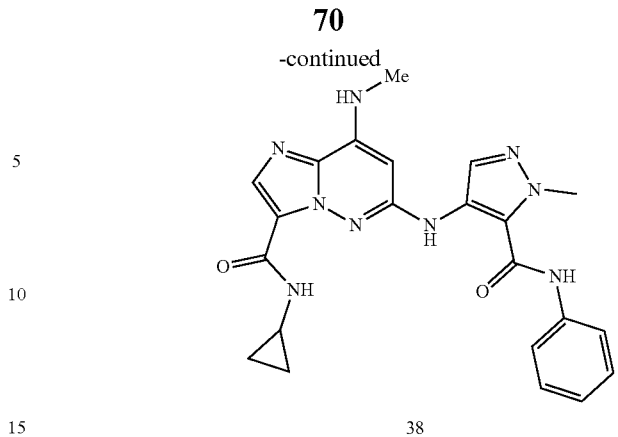

38

A mixture of 4-((3-(cyclopropylcarbamoyl)-8-((4-methoxybenzyl)(methyl) amino)imidazo[1,2-b]pyridazin-6-yl)amino)-1-methyl-1H-pyrazole-5-carboxylic acid (18 mg, 0.037 mmol), aniline (6.83 mg, 0.073 mmol), BOP (21.10 mg, 0.048 mmol) and Et3N (0.015 mL, 0.110 mmol) was agitated at rt for 2.5 hr. The volatiles were removed in vacuo to afford a yellow oil that was treated with HCl, 4N in dioxane (0.177 mL, 0.707 mmol) in DCM at rt for 1 hr. MeOH (1 ml) was added and the reaction mixture was concentrated to driness. The residue was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-50% B over 25 minutes, then a 10-minute hold at 50% B; Flow: 25 mL/min. Fractions containing the desired product were combined and dried via centrifugal evaporation N-cyclopropyl-6-((1-methyl-5-(methylcarbamoyl)-1H-pyrazol-4-yl)amino)-8-(methylamino)imidazo[1,2-b]pyridazine-3-carboxamide (7.8 mg, 0.021 mmol, 56% yield). LC retention time 1.14 min [D]. MS (E+) m/z: 446 (MH+). $^1$H NMR (500 MHz, DMSO-d$_6$) δ 8.64 (d, J=4.4 Hz, 1H), 7.77 (s, 1H), 7.70 (s, 1H), 7.59 (d, J=7.7 Hz, 2H), 7.43 (d, J=4.7 Hz, 1H), 7.31 (t, J=7.9 Hz, 2H), 7.14-7.06 (m, 1H), 5.77 (s, 1H), 4.02 (s, 3H), 2.83 (d, J=5.0 Hz, 4H), 0.80-0.60 (m, 2H), 0.45-0.31 (m, 2H) Two exchangeable proton missing.

Example 39

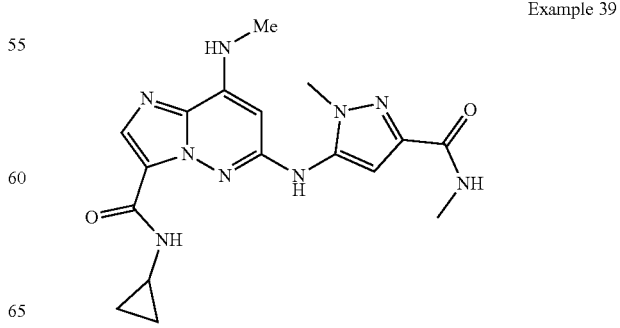

Example 39

1) BOP reagent, Et3N, aniline, DMA
2) HCl in dioxane, DCM

39a

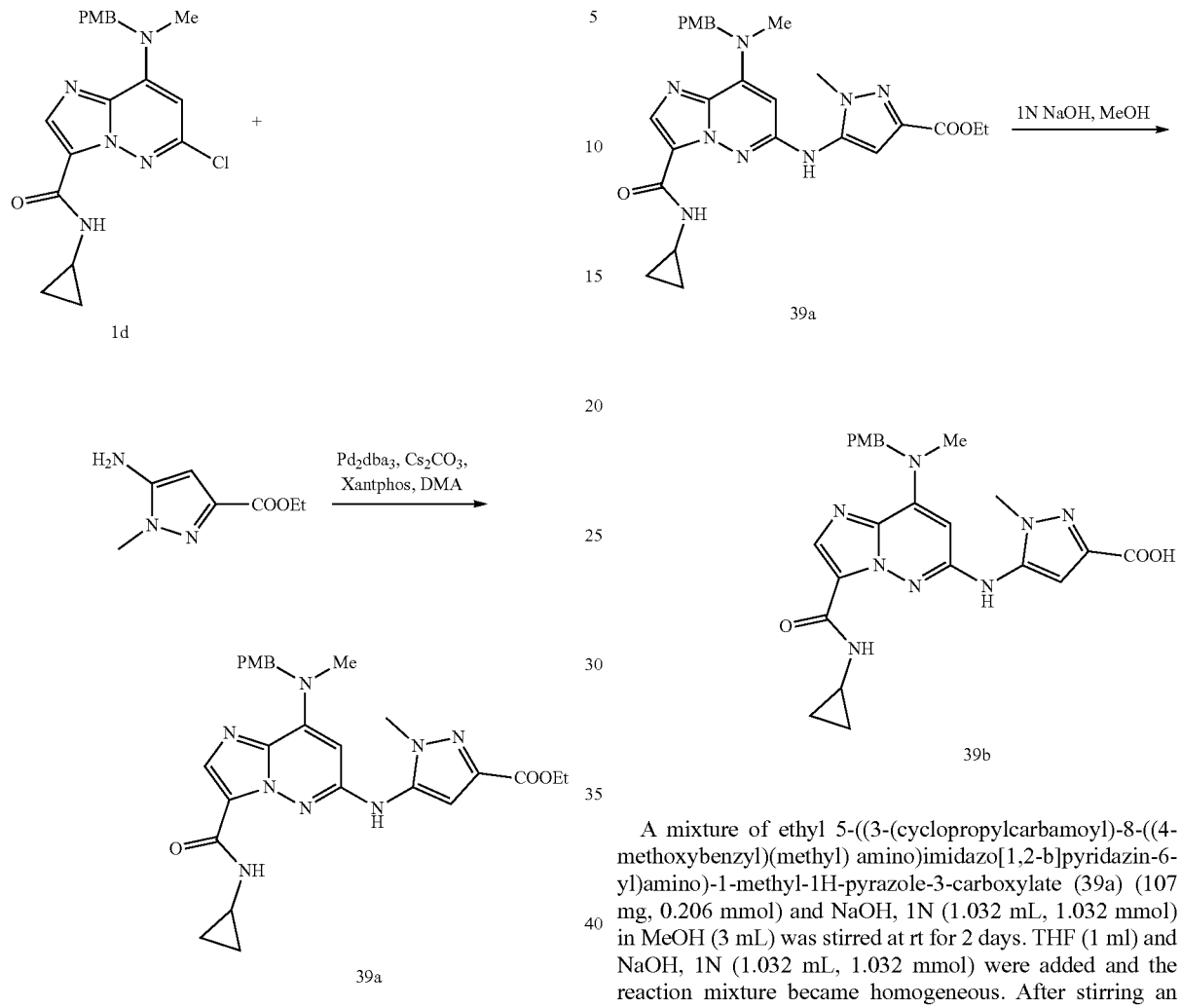

A mixture of 6-chloro-N-cyclopropyl-8-((4-methoxybenzyl)(methyl) amino)imidazo[1,2-b]pyridazine-3-carboxamide (1d) (125 mg, 0.324 mmol), ethyl 5-amino-1-methyl-1H-pyrazole-3-carboxylate [Free based (sodium bicarbonate solution/EtOAc) from HCl salt purchased from Acorn Pharma. Tech.] (88 mg, 0.518 mmol), Pd2(dba)3 (29.7 mg, 0.032 mmol), XANTPHOS (37.5 mg, 0.065 mmol) and Cs2CO3 (422 mg, 1.296 mmol) in DMA (2 mL) was degassed by bubbling $N_2$ through the mixture for 5 minutes. The reaction vessel was sealed and heated to 125° C. for 2 hr. After cooling to rt, the reaction mixture was partitioned between EtOAc (50 ml) and water (50 ml). The organic layer was washed with 10% LiCl solution (2×50 ml) and brine (50 ml). After drying ($Na_2SO_4$) and filtration the organic layer was concentrated to afford a tan solid that was chromatographed on a 12 gm ISCO silica gel cartridge, eluting with a 0-100% EtOAc/Hex gradient. The pure fractions were concentrated to afford ethyl 5-((3-(cyclopropylcarbamoyl)-8-((4-methoxybenzyl)(methyl)amino)imidazo[1,2-b]pyridazin-6-yl)amino)-1-methyl-1H-pyrazole-3-carboxylate (39a) (126 mg, 0.243 mmol, 75% yield) as a tan solid. LC retention time 2.77 min [C]. MS (E+) m/z: 519 (MH+).

39b

A mixture of ethyl 5-((3-(cyclopropylcarbamoyl)-8-((4-methoxybenzyl)(methyl) amino)imidazo[1,2-b]pyridazin-6-yl)amino)-1-methyl-1H-pyrazole-3-carboxylate (39a) (107 mg, 0.206 mmol) and NaOH, 1N (1.032 mL, 1.032 mmol) in MeOH (3 mL) was stirred at rt for 2 days. THF (1 ml) and NaOH, 1N (1.032 mL, 1.032 mmol) were added and the reaction mixture became homogeneous. After stirring an additional 24 hr, the MeOH and THF were removed on the rotovap and the aqueous mixture was acidified to pH 1 with 1N HCl. Filtered suspension. Dried under high vacuum to a hard pellet. This pellet was dissolved in DCM and MeOH and was transferred for concentration. Concentration and drying afforded 5-((3-(cyclopropylcarbamoyl)-8-((4-methoxybenzyl)(methyl)amino)imidazo[1,2-b]pyridazin-6-yl)amino)-1-methyl-1H-pyrazole-3-carboxylic acid (39b) (77 mg, 0.157 mmol, 76% yield) as a white solid. LC retention time 2.41 min [C]. MS (E+) m/z: 491 (MH+).

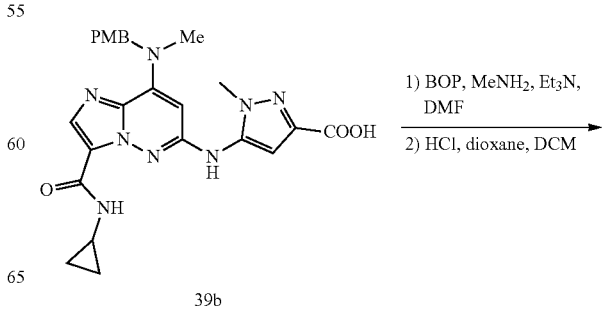

-continued

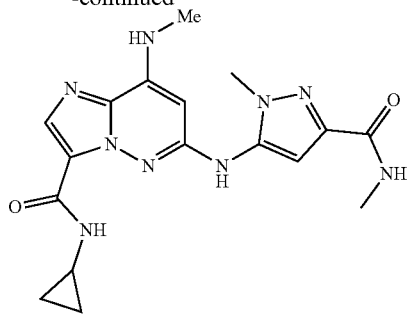

39

Example 39

A mixture of 5-((3-(cyclopropylcarbamoyl)-8-((4-methoxybenzyl)(methyl) amino)imidazo[1,2-b]pyridazin-6-yl)amino)-1-methyl-1H-pyrazole-3-carboxylic acid (39b) (12 mg, 0.024 mmol), methanamine, 2M in THF (0.061 mL, 0.122 mmol), BOP (14.07 mg, 0.032 mmol) and Et3N (10.23 μl, 0.073 mmol) was agitated at rt for 1 hr. The volatiles were removed in vacuo to afford a yellow oil that was treated with HCl, 4N in dioxane (0.089 mL, 0.357 mmol) in DCM (0.25 mL) at rt for 1 hr. The reaction mixture was concentrated and the residue was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-40% B over 25 minutes, then a 10-minute hold at 40% B; Flow: 25 mL/min. Fractions containing the desired product were combined and dried via centrifugal evaporation to afford N-cyclopropyl-6-((1-methyl-3-(methylcarbamoyl)-1H-pyrazol-5-yl)amino)-8-(methylamino)imidazo[1,2-b]pyridazine-3-carboxamide (39) (5.3 mg, 0.014 mmol, 57% yield). LC retention time 0.74 min [D]. MS (E+) m/z: 384 (MH+). $^1$H NMR (500 MHz, DMSO-d$_6$) δ 9.05 (s, 1H), 8.49 (d, J=4.3 Hz, 1H), 8.06 (d, J=4.9 Hz, 1H), 7.81 (s, 1H), 7.63 (d, J=4.9 Hz, 1H), 6.53 (s, 1H), 5.76 (s, 1H), 3.73 (s, 3H), 3.17 (d, J=4.9 Hz, 3H), 2.94-2.82 (m, 3H), 2.74 (s, 1H), 0.64-0.53 (m, 2H), 0.34-0.22 (m, 2H).

Example 40

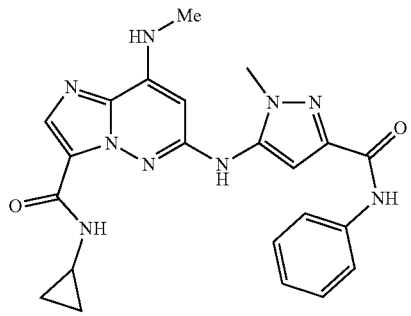

Example 40

Example 40

Example 40 was prepared in a similar manner to Example 39: LC retention time 1.23 min [D]. MS (E+) m/z: 446. $^1$H NMR (500 MHz, DMSO-d$_6$) δ 10.02 (s, 1H), 9.15 (s, 1H), 8.53 (d, J=4.3 Hz, 1H), 7.88-7.78 (m, 3H), 7.67 (d, J=4.9 Hz, 1H), 7.34 (t, J=7.9 Hz, 2H), 7.14-7.05 (m, 1H), 6.75 (s, 1H), 5.81 (s, 1H), 3.83 (s, 3H), 2.90 (d, J=4.9 Hz, 3H), 2.76 (d, J=4.3 Hz, 1H), 0.66-0.53 (m, 2H), 0.38-0.29 (m, 2H).

Example 41

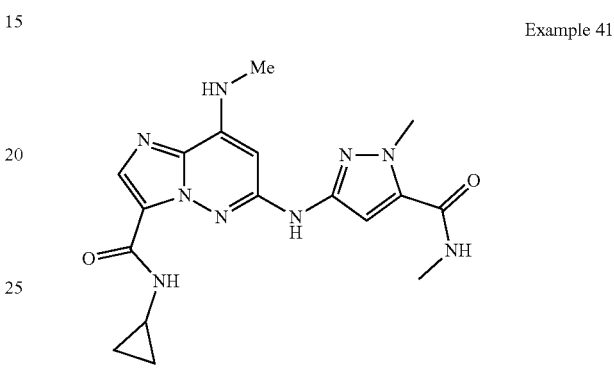

Example 41

41a

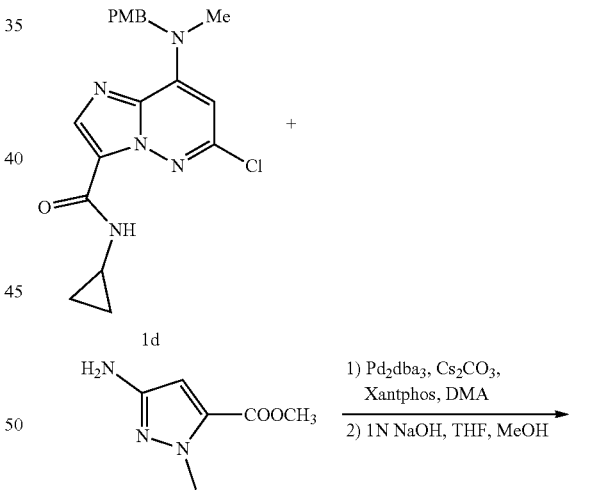

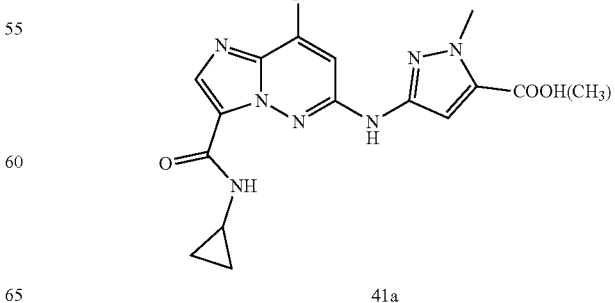

41a

A mixture of 6-chloro-N-cyclopropyl-8-((4-methoxybenzyl)(methyl)amino)imidazo[1,2-b]pyridazine-3-carboxamide (1d) (125 mg, 0.324 mmol), methyl 3-amino-1-methyl-1H-pyrazole-5-carboxylate [commercially available from Princeton Bio](101 mg, 0.648 mmol), Pd2(dba)3 (29.7 mg, 0.032 mmol), XANTPHOS (37.5 mg, 0.065 mmol) and Cs2CO3 (422 mg, 1.296 mmol) in DMA (2 mL) was degassed by bubbling $N_2$ through the mixture for 5 minutes. The reaction vessel was sealed and heated to 125° C. for 2 hr. LCMS indidated a roughly even mixture of ester and acid. After cooling to rt, 1N NaOH (1 ml) was added and stirring was continued at rt for 5 hr. The reaction mixture was partitioned between EtOAc (30 ml) and water (25 ml). The first aqueous layer was put aside. The organic layer was washed with 10% LiCl solution (2×25 ml) and brine (25 ml). After drying ($Na_2SO_4$) and filtration the organic layer was concentrated to a residue that was chromatographed on a 4 gm ISCO silica gel cartridge, eluting with a 0-100% EtOAc/Hex gradient. No product was isolated. Most partitioned into the organic extracted from the acidified aqueous and is being carried forward as a mixture of acid and ester into the hydrolysis step. The first aqueous layer was acidified to pH ~1 with 1N HCl and the cloudy mixture was transferred to a separatory funnel. The mixture was extracted with EtOAc (50 ml) and EtOAc:THF, 3:1 (40 ml). The combined organics were washed with 10% LiCl (2×40 ml) and brine (40 ml). After drying ($MgSO_4$) and filtration the organic layer was concentrated to afford a ~5:4 mixture of ester to acid that was unsuccessfully treated with additional 1N NaOH in MeOH and THF. The final ratio of ester to acid was 1:1. This material was used as is in future reactions. Ester: LC retention time 2.76 min [C]. MS (E+) m/z: 505. Acid: LC retention time 2.68 min [C]. MS (E+) m/z: 491.

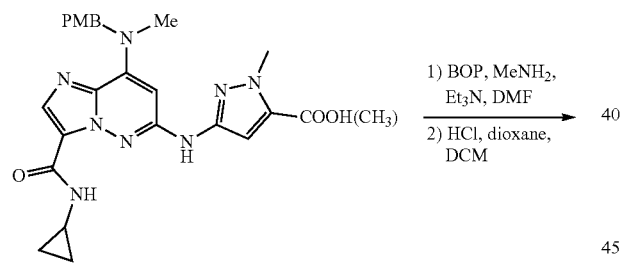

41a

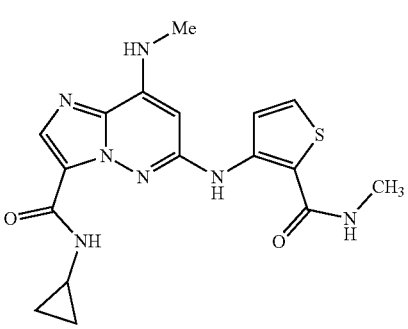

41

Example 41

A mixture of 41a (30 mg, 0.061 mmol), methanamine, 2M in THF (0.153 mL, 0.306 mmol), BOP (35.2 mg, 0.080 mmol) and $Et_3N$ (0.026 mL, 0.183 mmol) was agitated at rt for 1 hr. The volatiles were removed in vacuo to afford impure a yellow oil that was treated with HCl, 4N in dioxane (0.15 mL, 0.060 mmol) in DCM (1 mL) at rt for 1 hr. The volatiles were removed in vacuo and the residue was purified via preparative LC/MS with the following conditions: Column: Waters XBridge C18, 19×250 mm, 5-m particles; Mobile Phase A: 5:95 acetonitrile:water with 10-mM ammonium acetate; Mobile Phase B: 95:5 acetonitrile:water with 10-mM ammonium acetate; Gradient: 0-100% B over 25 minutes, then a 5-minute hold at 100% B; Flow: 20 mL/min. Fractions containing the desired product were combined and dried via centrifugal evaporation N-cyclopropyl-6-((1-methyl-5-(methylcarbamoyl)-1H-pyrazol-3-yl)amino)-8-(methylamino)imidazo[1,2-b]pyridazine-3-carboxamide (41) (5.5 mg, 0.014 mmol, 23% yield). LC retention time 0.77 min [D]. MS (E+) m/z: 384 (MH+). $^1$H NMR (500 MHz, DMSO-$d_6$) δ 9.41 (s, 1H), 8.93 (d, J=3.7 Hz, 1H), 8.44 (d, J=4.3 Hz, 1H), 7.82 (s, 1H), 7.49 (d, J=4.9 Hz, 1H), 6.76 (s, 1H), 5.85 (s, 1H), 4.02 (s, 3H), 2.86 (d, J=4.9 Hz, 3H), 2.82 (td, J=7.3, 3.7 Hz, 1H), 2.76 (d, J=4.9 Hz, 3H), 0.71-0.62 (m, 2H), 0.49-0.40 (m, 2H).

Example 42

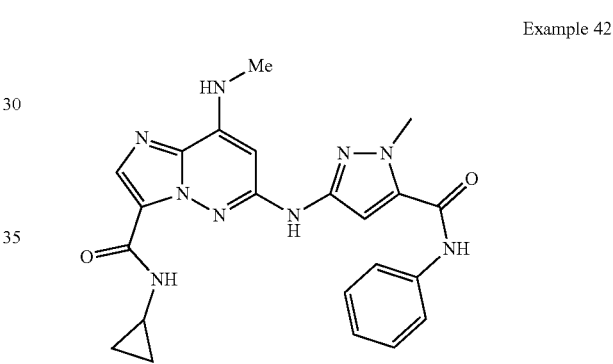

Example 42

Example 42 was prepared in a similar manner to Example 41: LC retention time 1.25 min [D]. MS (E+) m/z: 446. $^1$H NMR (500 MHz, DMSO-$d_6$) δ 10.22 (s, 1H), 9.52 (s, 1H), 8.94 (d, J=3.1 Hz, 1H), 7.73 (d, J=7.9 Hz, 2H), 7.50 (d, J=4.9 Hz, 1H), 7.36 (t, J=7.9 Hz, 2H), 7.16-7.07 (m, 3H), 5.86 (s, 1H), 4.05 (s, 3H), 2.86 (d, J=4.9 Hz, 3H), 2.75 (dt, J=7.3, 3.7 Hz, 1H), 0.62-0.49 (m, 2H), 0.46-0.36 (m, 2H).

Example 43

Example 43

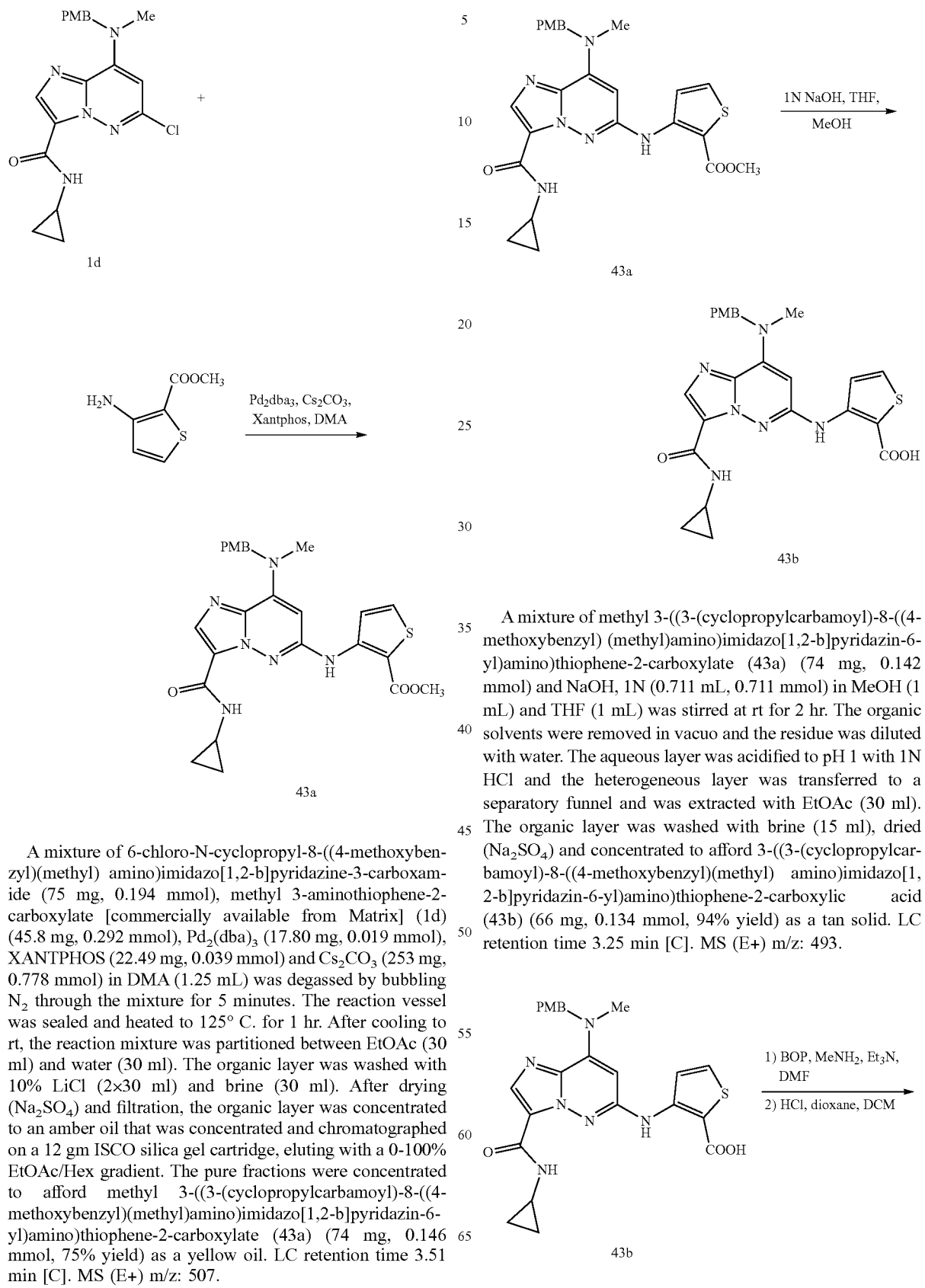

A mixture of 6-chloro-N-cyclopropyl-8-((4-methoxybenzyl) (methyl) amino)imidazo[1,2-b]pyridazine-3-carboxamide (75 mg, 0.194 mmol), methyl 3-aminothiophene-2-carboxylate [commercially available from Matrix] (1d) (45.8 mg, 0.292 mmol), Pd$_2$(dba)$_3$ (17.80 mg, 0.019 mmol), XANTPHOS (22.49 mg, 0.039 mmol) and Cs$_2$CO$_3$ (253 mg, 0.778 mmol) in DMA (1.25 mL) was degassed by bubbling N$_2$ through the mixture for 5 minutes. The reaction vessel was sealed and heated to 125° C. for 1 hr. After cooling to rt, the reaction mixture was partitioned between EtOAc (30 ml) and water (30 ml). The organic layer was washed with 10% LiCl (2×30 ml) and brine (30 ml). After drying (Na$_2$SO$_4$) and filtration, the organic layer was concentrated to an amber oil that was concentrated and chromatographed on a 12 gm ISCO silica gel cartridge, eluting with a 0-100% EtOAc/Hex gradient. The pure fractions were concentrated to afford methyl 3-((3-(cyclopropylcarbamoyl)-8-((4-methoxybenzyl)(methyl)amino)imidazo[1,2-b]pyridazin-6-yl)amino)thiophene-2-carboxylate (43a) (74 mg, 0.146 mmol, 75% yield) as a yellow oil. LC retention time 3.51 min [C]. MS (E+) m/z: 507.

A mixture of methyl 3-((3-(cyclopropylcarbamoyl)-8-((4-methoxybenzyl) (methyl)amino)imidazo[1,2-b]pyridazin-6-yl)amino)thiophene-2-carboxylate (43a) (74 mg, 0.142 mmol) and NaOH, 1N (0.711 mL, 0.711 mmol) in MeOH (1 mL) and THF (1 mL) was stirred at rt for 2 hr. The organic solvents were removed in vacuo and the residue was diluted with water. The aqueous layer was acidified to pH 1 with 1N HCl and the heterogeneous layer was transferred to a separatory funnel and was extracted with EtOAc (30 ml). The organic layer was washed with brine (15 ml), dried (Na$_2$SO$_4$) and concentrated to afford 3-((3-(cyclopropylcarbamoyl)-8-((4-methoxybenzyl)(methyl) amino)imidazo[1,2-b]pyridazin-6-yl)amino)thiophene-2-carboxylic acid (43b) (66 mg, 0.134 mmol, 94% yield) as a tan solid. LC retention time 3.25 min [C]. MS (E+) m/z: 493.

-continued

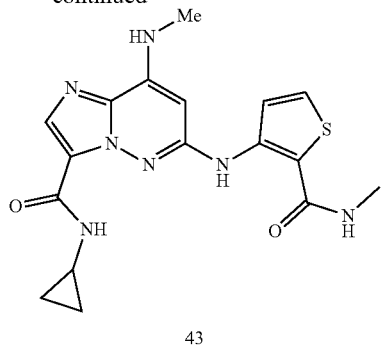

43

Example 43

A mixture of 3-((3-(cyclopropylcarbamoyl)-8-((4-methoxybenzyl)(methyl) amino)imidazo[1,2-b]pyridazin-6-yl)amino)thiophene-2-carboxylic acid (43b) (15 mg, 0.030 mmol), methanamine, HCl (4.11 mg, 0.061 mmol), BOP (17.51 mg, 0.040 mmol) and triethylamine (0.021 mL, 0.152 mmol) in DMF (0.25 mL) was agitated at rt for 60 hr. The volatiles were removed in vacuo to afford a yellow oil that was treated with HCl, 4N in dioxane (0.074 mL, 0.297 mmol) in DCM (2 mL) at rt for 3 hr. The volatiles were removed in vacuo and the residue was purified via preparative LC/MS with the following conditions: Column: Waters XBridge C18, 19×250 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 25 minutes, then a 7-minute hold at 100% B; Flow: 20 mL/min. Fractions containing the desired product were combined and dried via centrifugal evaporation to afford N-cyclopropyl-8-(methylamino)-6-((2-(methylcarbamoyl)thiophen-3-yl)amino)imidazo[1,2-b]pyridazine-3-carboxamide (43) (4 mg, 0.01 mmol, 33% yield). LC retention time 1.13 min [D]. MS (E+) m/z: 386. $^1$H NMR (500 MHz, DMSO-$d_6$) δ 10.22 (s, 1H), 8.56 (d, J=3.7 Hz, 1H), 8.12 (d, J=4.3 Hz, 1H), 7.84 (s, 1H), 7.80-7.75 (m, 1H), 7.74-7.70 (m, 1H), 7.54 (d, J=4.9 Hz, 1H), 5.91 (s, 1H), 2.94-2.81 (m, 4H), 2.76 (d, J=4.3 Hz, 3H), 0.75 (d, J=5.5 Hz, 2H), 0.49 (br. s., 2H).

The following Examples were prepared in a similar manner to Example 43.

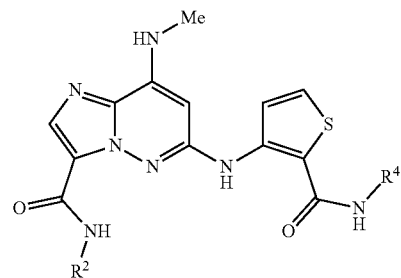

| Example number | R² | R⁴ | Rt (min) [Method] | m/z [M + H]⁺ |
|---|---|---|---|---|
| 44 | cyclopropyl | isopropyl | 1.37 [D] | 414 |
| 45 | cyclopropyl | 4-fluorophenyl | 1.59 [D] | 466 |
| 46 | cyclopropyl | 3-pyridyl | 0.90 [D] | 449 |
| 47 | cyclopropyl | C(CD₃)₂D (tert-butyl-d) | 1.08 [D] | 389 |
| 48 | -CH₂CH₂OCH₃ | C(CD₃)₂D | 1.03 [D] | 407 |
| 49 | -CH₂CH₂OH | C(CD₃)₂D | 0.87 [D] | 393 |

-continued

| Example number | R² | R⁴ | Rt (min) [Method] | m/z [M + H]⁺ |
|---|---|---|---|---|
| 50 |  |  | 1.23 [D] | 403 |

| Compound | ¹H NMR |
|---|---|
| 44 | ¹H NMR (500 MHz, DMSO-d₆) δ 10.25 (s, 1H), 8.55 (d, J = 3.7 Hz, 1H), 7.92 (d, J = 7.9 Hz, 1H), 7.84 (s, 1H), 7.78 (s, 1H), 7.71 (d, J = 4.9 Hz, 1H), 7.54 (d, J = 4.9 Hz, 1H), 5.91 (s, 1H), 4.16-4.02 (m, 1H), 2.94-2.80 (m, 4H), 1.15 (d, J = 6.1 Hz, 6H), 0.79-0.66 (m, 2H), 0.56-0.40 (m, 2H). |
| 45 | ¹H NMR (500 MHz, DMSO-d₆) δ 10.01 (d, J = 18.9 Hz, 1H), 8.57 (br. s., 1H), 7.99-7.76 (m, 3H), 7.68 (br. s., 2H), 7.57 (br. s., 1H), 7.19 (d, J = 8.5 Hz, 2H), 5.98 (br. s., 1H), 2.88 (br. s., 4H), 0.77 (br. s., 2H), 0.50 (br. s., 2H) One exchangeable proton missing. |
| 46 | ¹H NMR (500 MHz, DMSO-d₆) δ 10.13 (br. s., 2H), 8.85 (br. s., 1H), 8.58 (d, J = 3.7 Hz, 1H), 8.31 (br. s., 1H), 8.07 (d, J = 8.5 Hz, 1H), 7.93 (d, J = 5.5 Hz, 1H), 7.86 (s, 1H), 7.81 (d, J = 5.5 Hz, 1H), 7.55 (d, J = 4.3 Hz, 1H), 7.40 (d, J = 4.3 Hz, 1H), 6.00 (s, 1H), 2.93-2.80 (m, 4H), 0.76 (d, J = 4.9 Hz, 2H), 0.56-0.43 (m, 2H). |
| 47 | ¹H NMR (500 MHz, DMSO-d₆) δ 10.21 (s, 1H), 8.57 (d, J = 3.7 Hz, 1H), 8.09 (s, 1H), 7.84 (s, 1H), 7.80-7.75 (m, 1H), 7.73-7.67 (m, 1H), 7.53 (d, J = 4.9 Hz, 1H), 5.90 (s, 1H), 2.89 (d, J = 4.3 Hz, 4H), 0.75 (d, J = 5.5 Hz, 2H), 0.48 (br. s., 2H). |
| 48 | ¹H NMR (500 MHz, DMSO-d₆) δ 10.32 (s, 1H), 8.72 (br. s., 1H), 8.09 (s, 1H), 7.86 (s, 1H), 7.80-7.75 (m, 1H), 7.75-7.67 (m, 1H), 7.55 (d, J = 4.9 Hz, 1H), 5.91 (s, 1H), 3.21 (s, 3H), 2.90 (d, J = 4.9 Hz, 3H) Four protons obscurred by water peak.. |
| 49 | ¹H NMR (500 MHz, DMSO-d₆) δ 10.29 (s, 1H), 8.71 (t, J = 5.8 Hz, 1H), 8.09 (s, 1H), 7.86 (s, 1H), 7.81 (d, J = 5.5 Hz, 1H), 7.70 (d, J = 5.5 Hz, 1H), 7.49 (d, J = 4.9 Hz, 1H), 5.89 (s, 1H), 4.97 (t, J = 5.5 Hz, 1H), 3.55-3.47 (m, 2H), 3.41 (q, J = 5.5 Hz, 2H), 2.93-2.84 (m, 3H). |
| 50 | ¹H NMR (500 MHz, DMSO-d₆) δ 10.18 (s, 1H), 8.74 (d, J = 7.9 Hz, 1H), 8.09 (s, 1H), 7.83 (s, 1H), 7.81-7.77 (m, 2H), 7.53 (d, J = 4.9 Hz, 1H), 5.92 (s, 1H), 4.56-4.34 (m, 1H), 2.96-2.84 (m, 3H), 2.25 (d, J = 7.9 Hz, 2H), 1.95-1.81 (m, 2H), 1.77-1.58 (m, 2H). |

Example 51

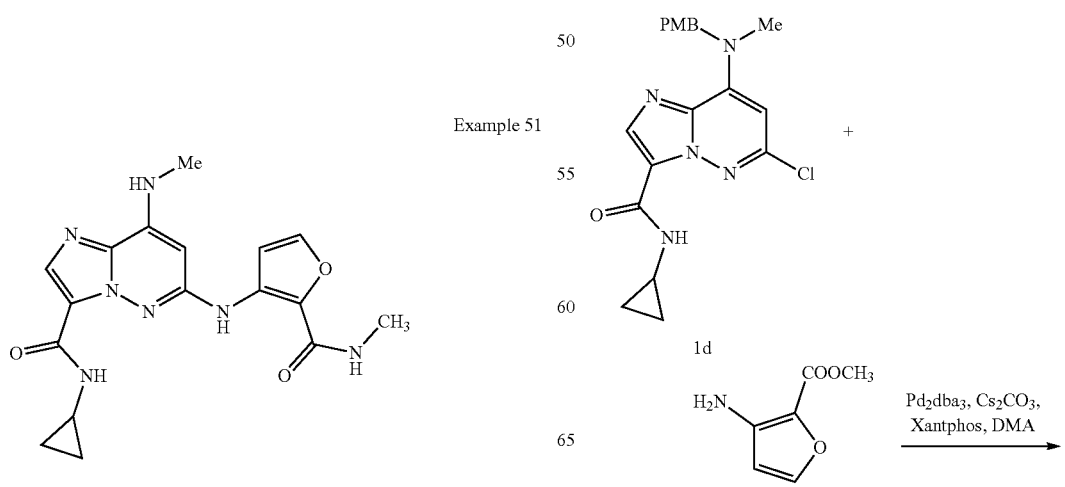

83

-continued

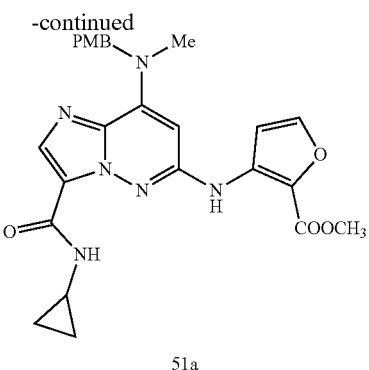

51a

A mixture of 6-chloro-N-cyclopropyl-8-((4-methoxybenzyl)(methyl) amino)imidazo[1,2-b]pyridazine-3-carboxamide (1d) (150 mg, 0.389 mmol), methyl 3-aminofuran-2-carboxylate [commercially available from Ark Chemical] (60.3 mg, 0.428 mmol), Pd$_2$(dba)$_3$ (35.6 mg, 0.039 mmol), XANTPHOS (45.0 mg, 0.078 mmol) and Cs$_2$CO$_3$ (507 mg, 1.555 mmol) in DMA (2.5 mL) was degassed by bubbling N$_2$ through the mixture for 5 minutes. The reaction vessel was sealed and heated to 125° C. for 1.5 hr. The reaction mixture was partitioned between EtOAc (30 ml) and water (30 ml). The first aqueous layer was reserved. The organic layer was washed with 10% LiCl solution (2×30 ml) and brine (30 ml). After drying (Na$_2$SO$_4$) and filtration the organic layer was concentrated to afford an amber oil that was chromatographed on a 12 gm ISCO silica gel cartridge, eluting with a 0-100% EtOAc/Hex gradient. The pure fractions were concentrated to afford methyl 3-((3-(cyclopropylcarbamoyl)-8-((4-methoxybenzyl)(methyl)amino)imidazo[1,2-b]pyridazin-6-yl)amino)furan-2-carboxylate (51a) (140 mg, 0.285 mmol, 73.4% yield) as a yellow oil. LC retention time 3.19 min [C]. MS (E+) m/z: 491.

51b

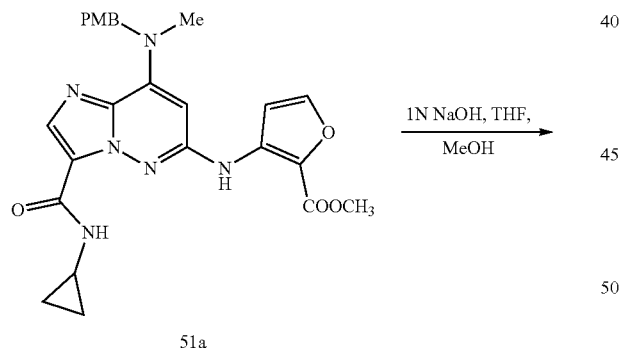

51b

84

A mixture of methyl 3-((3-(cyclopropylcarbamoyl)-8-((4-methoxybenzyl)(methyl) amino)imidazo[1,2-b]pyridazin-6-yl)amino)furan-2-carboxylate (51a) (128 mg, 0.261 mmol) and NaOH, 1N (1.305 mL, 1.305 mmol) in MeOH (2 mL) and THF (2 mL) was stirred at rt for 2 hr. The organic solvents were removed in vacuo and the residue was diluted with water. The aqueous layer was acidified to pH 1 with 1N HCl and the heterogeneous layer was transferred to a separatory funnel and was extracted with EtOAc (30 ml). The organic layer was washed with brine (15 ml), dried (Na$_2$SO$_4$) and concentrated to afford 3-((3-(cyclopropylcarbamoyl)-8-((4-methoxybenzyl)(methyl) amino)imidazo[1,2-b]pyridazin-6-yl)amino)furan-2-carboxylic acid (51b) (81 mg, 0.170 mmol, 65.1% yield) as a tan solid. LC retention time 2.93 min [C]. MS (E+) m/z: 477.

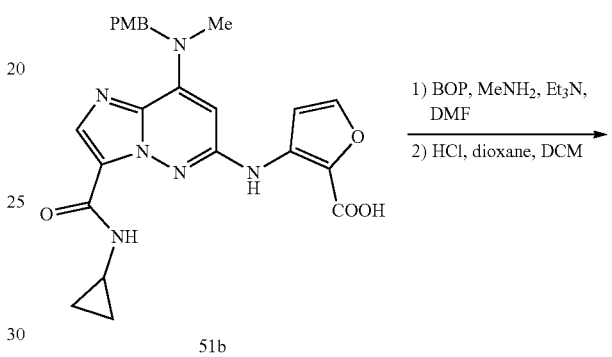

51b

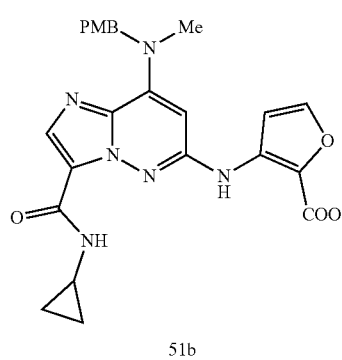

51

Example 51

A mixture of 3-((3-(cyclopropylcarbamoyl)-8-((4-methoxybenzyl)(methyl) amino)imidazo[1,2-b]pyridazin-6-yl)amino)furan-2-carboxylic acid (15 mg, 0.031 mmol), methanamine, HCl (4.25 mg, 0.063 mmol), BOP (18.10 mg, 0.041 mmol) and triethylamine (0.022 mL, 0.157 mmol) in DMF (0.25 mL) was agitated at rt for 60 hr. The volatiles were removed in vacuo to a yellow oil that was treated with HCl (0.077 mL, 0.306 mmol) in DCM (1 mL) at rt for 1 hr. The volatiles were removed and the residue was purified via preparative LC/MS with the following conditions: Column: Waters XBridge C18, 19×250 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 5-100% B over 25 minutes, then a 5-minute hold at 100% B; Flow: 20 mL/min. Fractions containing the desired product were combined and dried via centrifugal evaporation to afford N-cyclopropyl-8-(methylamino)-6-((2-(methylcarbamoyl)furan-3-yl) amino)imidazo[1,2-b]pyridazine-3-carboxamide (3.6 mg, 0.01 mmol, 31% yield). LC retention time 1.03 min [D]. MS (E+) m/z: 370. $^1$H NMR (500 MHz, DMSO-$d_6$) δ 8.86 (s, 1H), 8.63 (br. s., 1H), 8.19 (br. s., 1H), 7.84 (s, 1H), 7.76 (s, 1H), 7.41 (br. s., 1H), 7.17 (s, 1H), 6.02 (s, 1H), 2.86 (d, J=4.9 Hz, 4H), 2.75 (d, J=4.3 Hz, 3H), 0.75 (d, J=6.1 Hz, 2H), 0.49 (br. s., 2H).

The following Examples were prepared in a similar manner to Example 51.

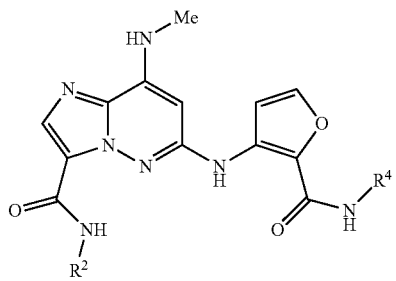

| Example number | R² | R⁴ | Rt (min) [Method] | m/z [M + H]⁺ |
|---|---|---|---|---|
| 52 | cyclopropyl | ethyl (CH₂CH₃) | 1.18 [D] | 384 |
| 53 | cyclopropyl | C(CD)₂ (d-labeled isopropyl) | 1.03 [D] | 373 |
| 54 | cyclopropyl | isopropyl | 1.33 [D] | 398 |
| 55 | cyclopropyl | 6-methoxypyridin-3-yl | 1.29 [D] | 463 |
| 56 | cyclopropyl | 4-fluorophenyl | 1.59 [D] | 450 |
| 57 | cyclopropyl | 2-methoxyethyl | 1.11 [D] | 413 |
| 58 | cyclopropyl | pyridin-3-yl | 0.87 [D] | 433 |

| Compound | $^1$H NMR |
|---|---|
| 52 | $^1$H NMR (500 MHz, DMSO-$d_6$) δ 8.89 (s, 1H), 8.63 (d, J = 3.7 Hz, 1H), 8.29 (t, J = 5.8 Hz, 1H), 7.84 (s, 1H), 7.77 (s, 1H), 7.42 (d, J = 4.9 Hz, 1H), 7.18 (s, 1H), 6.03 (s, 1H), 3.32-3.20 (m, 2H), 2.92-2.79 (m, 4H), 1.09 (t, J = 7.3 Hz, 3H), 0.75 (d, J = 5.5 Hz, 2H), 0.49 (br. s., 2H). |
| 53 | $^1$H NMR (500 MHz, DMSO-$d_6$) δ 8.90 (s, 1H), 8.63 (d, J = 3.7 Hz, 1H), 8.17 (s, 1H), 7.86 (s, 1H), 7.78 (s, 1H), 7.44 (br. s., 1H), 7.19 (s, 1H), 6.05 (s, 1H), 2.91-2.79 (m, 4H), 0.79-0.69 (m, 2H), 0.50 (br. s., 2H). |
| 55 | $^1$H NMR (500 MHz, DMSO-$d_6$) δ 10.23 (s, 1H), 8.92(s, 1H), 8.63 (d, J = 3.7 Hz, 1H), 8.47 (d, J = 2.4 Hz, 1H), 8.00 (dd, J = 9.2, 2.4 Hz, 1H), 7.89 (s, 1H), 7.85 (s, 1H), 7.44 (d, J = 4.9 Hz, 1H), 7.29 (s, 1H), 6.82 (d, J = 9.2 Hz, 1H), 6.11 (s, 1H), 3.81 (s, 3H), 2.90-2.80 (m, 4H), 0.76 (d, J = 5.5 Hz, 2H), 0.51 (d, J = 3.7 Hz, 2H). |
| 56 | $^1$H NMR (500 MHz, DMSO-$d_6$) δ 10.23 (s, 1H), 8.95 (s, 1H), 8.62(d, J = 3.7 Hz, 1H), 7.89 (s, 1H), 7.85 (s, 1H), 7.75 (dd, J = 8.9, 5.2 Hz, 2H), 7.46 (d, J = 4.3 Hz, 1H), 7.30 (s, 1H), 7.16 (t, J = 8.9 Hz, 2H), 6.11 (s, 1H), 2.87 (d, J = 3.7 Hz, 4H), 0.89-0.66 (m, 2H), 0.62-0.32 (m, 2H). |
| 57 | $^1$H NMR (500 MHz, DMSO-$d_6$) δ 8.86 (s, 1H), 8.63 (d, J = 3.7 Hz, 1H), 8.25-8.16 (m, 1H), 7.84 (s, 1H), 7.78 (s, 1H), 7.41 (d, J = 4.9 Hz, 1H), 7.19 (s, 1H), 6.04 (s, 1H), 3.48-3.35 (m, 4H), 3.23 (s, 3H), 2.91-2.80 (m, 4H), 0.80-0.69 (m, 2H), 0.49 (br. s., 2H). |
| 58 | $^1$H NMR (500 MHz, DMSO-$d_6$) δ 10.80 (s, 1H), 9.21 (br. s., 1H), 8.99 (s, 1H), 8.57 (br. s., 1H), 8.54-8.47 (m, 2H), 8.02 (s, 1H), 7.88 (s, 1H), 7.82-7.72 (m, 1H), 7.55 (br. s., 1H), 7.43 (s, 1H), 6.21 (s, 1H), 2.88 (br. s., 4H), 0.76 (d, J = 6.1 Hz, 2H), 0.54 (br. s., 2H). |

Example 59

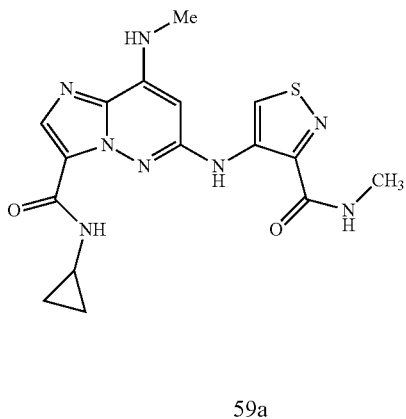

59a

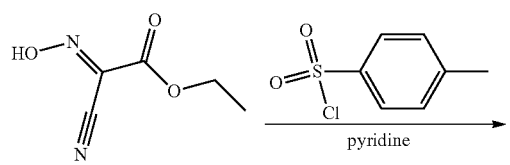

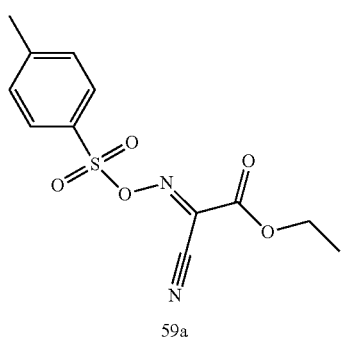

59a

A mixture of ethyl cyanoglyoxylate-2-oxime (5 g, 35.2 mmol) and p-toluenesulfonylchloride (7.38 g, 38.7 mmol) in pyridine (75 mL) was stirred at room temperature. After stirring over the weekend, the reaction was complete by LC-MS. The reaction mixture was concentrated to an orange oil, which was then redissolved in DCM and loaded onto a 120 g ISCO column for purification by flash chromatography, eluting with 0-100% EtOAc in hexanes. Concentration of pure fractions afforded (E)-ethyl 2-cyano-2-((tosyloxy)imino)acetate (59a) (7.75 g, 25.9 mmol, 73.6% yield) as a colorless oil that became a white crystalline solid on high vacuum.

LC retention time 1.07 min [A]. MS (E+) m/z: 298 (MH+). $^1$H NMR (400 MHz, METHANOL-$d_4$) δ 7.96-7.90 (m, 2H), 7.51 (d, J=8.1 Hz, 2H), 4.38 (q, J=7.0 Hz, 2H), 2.51-2.46 (m, 3H), 1.38-1.32 (m, 3H).

59b

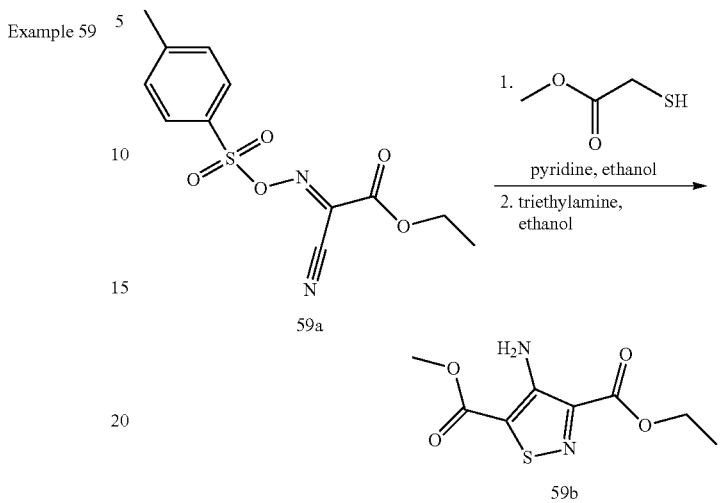

To a mixture of (E)-ethyl 2-cyano-2-((tosyloxy)imino)acetate (59a) (2.96 g, 9.99 mmol) and methyl thioglycolate (1.364 mL, 14.98 mmol) in absolute ethanol (5 mL) was added pyridine (1.022 mL, 12.64 mmol) dropwise. The mixture became a yellow solution over 20 minutes. After 30 minutes, the reaction mixture was partitioned between cold ether and ice water. The aqueous layer was extracted with cold ether twice. The combined ether layers were dried over sodium sulfate, filtered and concentrated. To a solution of this crude material in absolute ethanol (20 mL) was added triethylamine (1.858 mL, 13.33 mmol) dropwise. The yellow solution turned redder as the triethylamine was added. Within a few minutes after addition was complete a precipitate began to form after stirring 30 minutes at room temperature, the reaction mixture was filtered and dried to afford 3-ethyl 5-methyl 4-aminoisothiazole-3,5-dicarboxylate (59b) (1.1 g, 4.54 mmol, 45.4% yield) as a white solid. LC retention time 0.81 min [A]. MS (E+) m/z: 231 (MH+). $^1$H NMR (400 MHz, DMSO-$d_6$) δ 6.66 (br. s., 2H), 4.36 (q, J=7.2 Hz, 2H), 3.84 (s, 3H), 1.32 (t, J=7.0 Hz, 3H).

59c

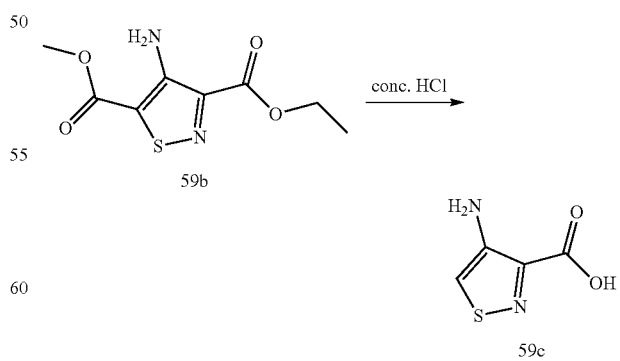

A mixture of 3-ethyl 5-methyl 4-aminoisothiazole-3,5-dicarboxylate (59b) (0.85 g, 3.69 mmol) in concentrated HCl (10 mL) was heated to reflux for 2 hours. The reaction was allowed to cool to room temperature, and then was placed on ice. The product precipitated out of solution, and was filtered off as a white solid. Drying overnight on vacuum afforded 4-aminoisothiazole-3-carboxylic acid (59c) (438 mg, 3.04 mmol, 82% yield) as a white solid. LC retention time 0.59 min [A]. $^1$H NMR (400 MHz, DMSO-$d_6$) δ 6.66 (br. s., 2H), 4.36 (q, J=7.2 Hz, 2H), 3.84 (s, 3H), 1.32 (t, J=7.0 Hz, 3H).

$^1$H NMR (400 MHz, DMSO-$d_6$) δ 14.08-13.54 (m, 1H), 7.75 (s, 1H), 6.69 (br. s., 2H)

59d

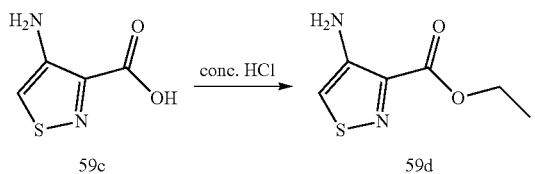

HCl gas was bubbled through a solution of 4-aminoisothiazole-3-carboxylic acid (0.21 g, 1.457 mmol) in ethanol (10 mL) at 0° C. for five minutes. The solution was then heated to reflux for 1 hour, whereupon the reaction was complete by LC-MS. Concentration and drying afforded ethyl 4-aminoisothiazole-3-carboxylate, HCl (59d) (237 mg, 1.124 mmol, 77% yield). as a white solid. LC retention time 0.96 min [A]. MS (E+) m/z: 173 (MH$^+$). $^1$H NMR (400 MHz, DMSO-$d_6$) δ 7.93 (s, 1H), 5.86 (br. s., 2H), 4.32 (q, J=7.0 Hz, 2H), 1.32 (t, J=7.2 Hz, 3H).

59e

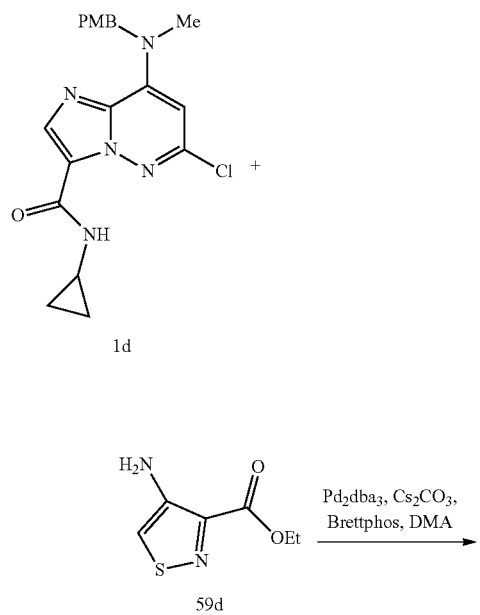

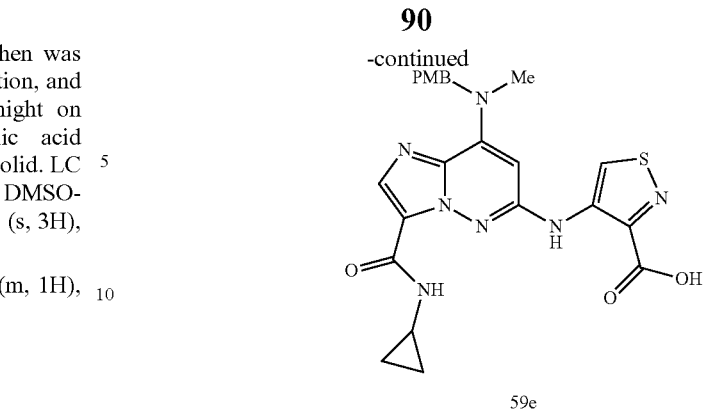

A mixture of 6-chloro-N-cyclopropyl-8-((4-methoxybenzyl)(methyl)amino)imidazo[1,2-b]pyridazine-3-carboxamide (1d) (175 mg, 0.454 mmol), ethyl 4-aminoisothiazole-3-carboxylate (59d) (172 mg, 0.998 mmol), BrettPhos (48.7 mg, 0.091 mmol) in DMA (3 mL) was degassed by bubbling N$_2$ through the mixture for 5 minutes. Pd$_2$(dba)$_3$ (83 mg, 0.091 mmol), and Cs$_2$CO$_3$ (517 mg, 1.587 mmol) were then added and the reaction vessel was sealed and heated to 110° C. overnight. The reaction mixture was heated further to 125° C. for 4 hours the following day. The reaction mixture was partitioned between EtOAc (30 ml) and water (30 ml). The aqueous layer was carefully acidified with 1N HCl (2 ml), and extracted with EtOAc (2×50 ml). This organic layer was washed with 10% LiCl solution (2×30 ml) and brine (30 ml). After drying (Na$_2$SO$_4$) and filtration the organic layer was concentrated to afford 4-((3-(cyclopropylcarbamoyl)-8-((4-methoxybenzyl)(methyl)amino)imidazo[1,2-b]pyridazin-6-yl)amino)isothiazole-3-carboxylic acid (59e) (135 mg, 0.191 mmol, 42.2% yield). as a tan solid. LC retention time 1.03 min [A]. MS (E+) m/z: 494.

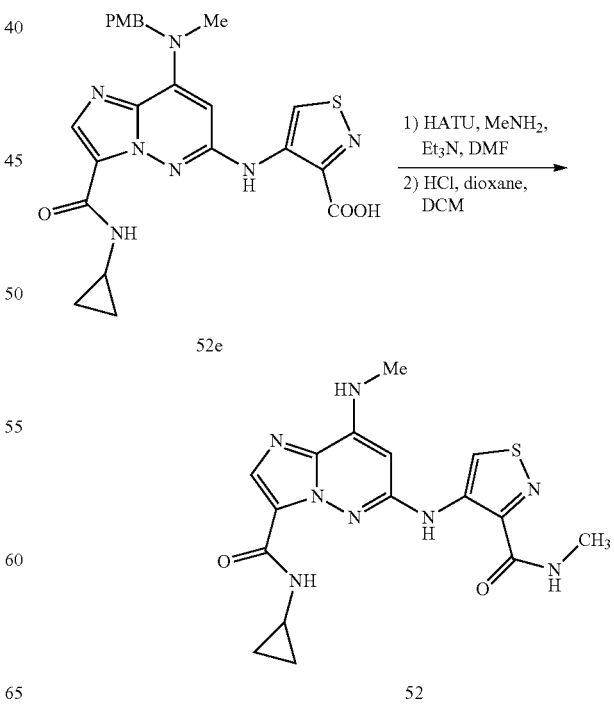

Example 59

A mixture of 4-((3-(cyclopropylcarbamoyl)-8-((4-methoxybenzyl)(methyl) amino)imidazo[1,2-b]pyridazin-6-yl)amino)isothiazole-3-carboxylic acid (59e) (30 mg, 0.061 mmol), methylamine,hydrochloride (12.3 mg, 0.182 mmol), HATU (30 mg, 0.079 mmol) and N,N-diisopropylethylamine (0.064 mL, 0.365 mmol) in DMF (1 mL) was agitated at rt for 2.5 hr. The volatiles were removed in vacuo to afford a yellow oil that was treated with HCl (0.111 mL, 0.444 mmol) in DCM (1 mL) at rt for 30 minutes. The volatiles were removed and the residue was purified via preparative LC/MS with the following conditions: Column: Waters XBridge C18, 19×250 mm, 5-m particles; Mobile Phase A: 5:95 acetonitrile: water with 0.1% trifluoroacetic acid; Mobile Phase B: 95:5 acetonitrile: water with 0.1% trifluoroacetic acid; Gradient: 5-100% B over 25 minutes, then a 5-minute hold at 100% B; Flow: 20 mL/min. Fractions containing the desired product were combined and dried via centrifugal evaporation to afford 4-((3-(cyclopropylcarbamoyl)-8-(methylamino)imidazo[1,2-b]pyridazin-6-yl)amino)-N-methylisothiazole-3-carboxamide (59) (3.2 mg, 0.0081 mmol, 27% yield). LC retention time 1.19 min [D]. MS (E+) m/z: 387. $^1$H NMR (500 MHz, DMSO-$d_6$) δ 10.05 (s, 1H), 9.40 (s, 1H), 8.96 (d, J=4.3 Hz, 1H), 8.49 (d, J=3.7 Hz, 1H), 7.89 (s, 1H), 7.50 (d, J=4.9 Hz, 1H), 5.99 (s, 1H), 2.92-2.86 (m, 4H), 2.84 (d, J=4.3 Hz, 3H), 0.79-0.73 (m, 2H), 0.59-0.54 (m, 2H).

The following Examples were prepared in a similar manner to Example 59.

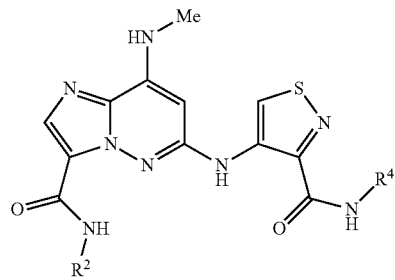

| Example number | R² | R⁴ | Rt (min) [Method] | m/z [M + H]⁺ |
|---|---|---|---|---|
| 60 | cyclopropyl | phenyl | 1.69 [D] | 449 |
| 61 | cyclopropyl | isopropyl | 1.55 [D] | 415 |
| 62 | cyclopropyl | ethyl | 1.37 [D] | 401 |
| 63 | cyclopropyl | 4-methoxyphenyl | 1.71 [D] | 479 |
| 64 | cyclopropyl | trans-2-fluorocyclopropyl | 1.33 [D] | 431 |
| 65 | cyclopropyl | CD₃ | 1.11 [D] | 413 |
| 66 | cyclopropyl | 4-fluorophenyl | 1.78 [D] | 467 |

-continued
| Example number | R² | R⁴ | Rt (min) [Method] | m/z [M + H]⁺ |
|---|---|---|---|---|
| 67 | 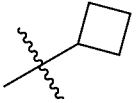 [SMILES: *C1CCC1] | 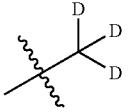 | 1.33 [D] | 404 |
| 68 | 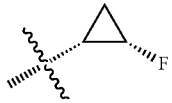 | 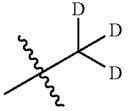 | 1.16 [D] | 408 |
| 69 | 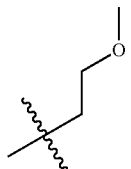 | 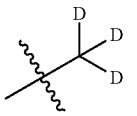 [SMILES: *C([2H])([2H])[2H]] | 1.15 [D] | 408 |
| 70 | 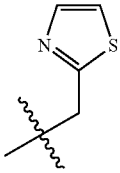 | 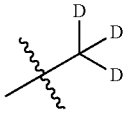 [SMILES: *C([2H])([2H])[2H]] | 1.17 [D] | 447 |
| 71 | 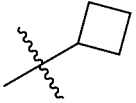 [SMILES: *C1CCC1] | 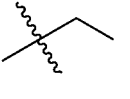 [SMILES: *CC] | 1.51 [D] | 415 |
| 72 | 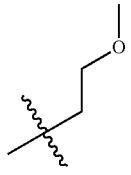 | 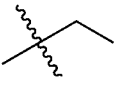 [SMILES: *CC] | 1.32 [D] | 419 |
| 73 | 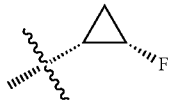 | 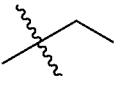 | 1.32 [D] | 419 |
| 74 | 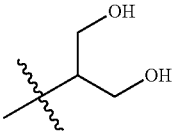 [SMILES: *C(CO)CO] |  | 0.93 [D] | 435 |
| 75 | 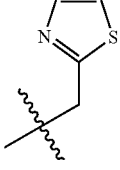 |  | 1.32 [D] | 458 |
| 76 | 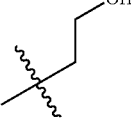 |  | 1.21 [D] | 405 |

-continued

| Example number | R² | R⁴ | Rt (min) [Method] | m/z [M + H]⁺ |
|---|---|---|---|---|
| 77 | (structure: CH with CH₂F branch) | (structure: isopropyl) | 1.35 [D] | 407 |

| Compound | ¹H NMR |
|---|---|
| 60 | ¹H NMR (500 MHz, DMSO-d₆) δ 10.82 (s, 1H), 9.75 (s, 1H), 9.50 (s, 1H), 8.52 (d, J = 3.7 Hz, 1H), 7.90 (s, 1H), 7.87 (d, J = 7.9 Hz, 2H), 7.51 (d, J = 4.9 Hz, 1H), 7.40 (t, J = 7.9 Hz, 2H), 7.20-7.15 (m, 1H), 6.09 (s, 1H), 2.93-2.87 (m, 4H), 0.79-0.74 (m, 2H), 0.60-0.55 (m, 2H) |
| 61 | ¹H NMR (500 MHz, DMSO-d₆) δ 10.02 (s, 1H), 9.39 (s, 1H), 8.77 (d, J = 7.9 Hz, 1H), 8.51 (br. s., 1H), 7.89 (s, 1H), 7.48 (br. s., 1H), 6.00 (s, 1H), 4.21-4.12(m, 1H), 2.90 (d, J = 4.9 Hz, 4H), 1.22 (d, J = 6.1 Hz, 6H), 0.76 (d, J = 5.5 Hz, 2H), 0.56 (br. s., 2H) |
| 62 | ¹H NMR (500 MHz, DMSO-d₆) δ 10.05 (s, 1H), 9.39 (s, 1H), 9.03 (t, J = 5.5 Hz, 1H), 8.51 (d, J = 3.1 Hz, 1H), 7.89 (s, 1H), 7.47 (d, J = 4.3 Hz, 1H), 5.99 (s, 1H), 3.34 (quin, J = 6.9 Hz, 2H), 2.92-2.86 (m, 4H), 1.15 (t, J = 7.3 Hz, 3H), 0.78-0.73 (m, 2H), 0.56 (br. s., 2H) |
| 63 | ¹H NMR (500 MHz, DMSO-d₆) δ 10.72 (s, 1H), 9.81 (s, 1H), 9.47 (s, 1H), 8.52 (d, J = 3.7 Hz, 1H), 7.90 (s, 1H), 7.76 (d, J = 9.2 Hz, 2H), 7.49 (d, J = 4.9 Hz, 1H), 6.96 (d, J = 8.5 Hz, 2H), 6.06 (s, 1H), 3.77 (s, 3H), 2.94-2.86 (m, 4H), 0.79-0.74 (m, 2H), 0.60-0.54 (m, 2H) |
| 64 | ¹H NMR (500 MHz, DMSO-d₆) δ 9.93 (s, 1H), 9.42 (s, 1H), 9.12 (d, J = 3.7 Hz, 1H), 8.50 (d, J = 3.7 Hz, 1H), 7.89 (s, 1H), 7.49 (d, J = 4.9 Hz, 1H), 6.03 (s, 1H), 4.88-4.71 (m, 1H), 4.16 (q, J = 5.5 Hz, 2H), 2.94-2.82 (m, 4H), 1.43-1.33 (m, 1H), 1.20-1.10 (m, 1H), 0.79-0.72 (m, 2H), 0.59-0.53 (m, 2H) |
| 65 | ¹H NMR (500 MHz, DMSO-d₆) δ 10.03 (s, 1H), 9.39 (s, 1H), 8.92 (s, 1H), 8.51 (d, J = 3.7 Hz, 1H), 7.89 (s, 1H), 7.47 (d, J = 4.9 Hz, 1H), 5.98 (s, 1H), 2.93-2.85 (m, 3H), 2.73 (s, 3H), 0.78-0.73 (m, 2H), 0.58-0.53 (m, 2H) |
| 66 | ¹H NMR (500 MHz, DMSO-d₆) δ 10.90 (s, 1H), 9.73 (s, 1H), 9.48 (s, 1H), 8.54 (br. s., 1H), 7.90 (s, 1H), 7.89-7.85 (m, 2H), 7.24 (t, J = 8.9 Hz, 2H), 6.07 (s, 1H), 2.92-2.86 (m, 5H), 0.76 (d, J = 6.1 Hz, 2H), 0.56 (br. s., 2H) |
| 67 | ¹H NMR (500 MHz, DMSO-d₆) δ 10.03 (s, 1H), 9.39 (s, 1H), 8.93 (s, 1H), 8.63 (d, J = 7.9 Hz, 1H), 7.89 (s, 1H), 7.50 (d, J = 4.9 Hz, 1H), 6.00 (s, 1H), 4.52-4.45 (m, 1H), 2.94-2.89 (m, 3H), 2.28 (br. s., 2H), 2.04-1.95 (m, 2H), 1.70 (dt, J = 9.8, 4.9 Hz, 2H) |
| 68 | ¹H NMR (500 MHz, DMSO-d₆) δ 10.09 (s, 1H), 9.33 (s, 1H), 8.93 (s, 1H), 8.57 (d, J = 3.7 Hz, 1H), 7.95 (s, 1H), 7.52 (d, J = 4.9 Hz, 1H), 6.00 (s, 1H), 4.94-4.76 (m, 1H), 2.99-2.86 (m, 4H), 1.26-1.16 (m, 1H), 1.09-0.99 (m, 1H) |
| 69 | ¹H NMR (500 MHz, DMSO-d₆) δ 10.14 (s, 1H), 9.20(s, 1H), 8.94(s, 1H), 8.65 (t, J = 5.8 Hz, 1H), 7.90 (s, 1H), 7.55 (d, J = 4.9 Hz, 1H), 5.99 (s, 1H), 3.60-3.55 (m, 2H), 3.54-3.50 (m, 2H), 3.28 (s, 3H), 2.94-2.89 (m, 3H) |
| 70 | ¹H NMR (500 MHz, DMSO-d₆) δ 10.09 (s, 1H), 9.23 (s, 1H), 8.89 (s, 1H), 7.98-7.92 (m, 2H), 7.76 (br. s., 1H), 7.65 (s, 1H), 7.47 (br. s., 1H), 5.98 (s, 1H), 4.91 (br. s., 2H), 2.94-2.88 (m, 3H) |
| 71 | ¹H NMR (500 MHz, DMSO-d₆) δ 9.97 (s, 1H), 9.32 (s, 1H), 8.99 (t, J = 5.8 Hz, 1H), 8.67 (d, J = 7.3 Hz, 1H), 7.87 (s, 1H), 7.41 (d, J = 4.3 Hz, 1H), 5.96 (s, 1H), 4.45 (sxt, J = 8.3 Hz, 1H), 3.33 (quin, J = 6.9 Hz, 2H), 2.90 (d, J = 4.9 Hz, 3H), 2.31-2.23 (m, 2H), 2.01-1.90 (m, 2H), 1.73-1.65 (m, 2H), 1.14 (t, J = 7.3 Hz, 3H) |
| 72 | ¹H NMR (500 MHz, DMSO-d₆) δ 10.12(s, 1H), 9.17(s, 1H), 9.02 (t, J = 5.8 Hz, 1H), 8.71-8.62 (m, 1H), 7.90 (s, 1H), 7.50 (d, J = 4.3 Hz, 1H), 5.97 (s, 1H), 3.33 (quin, J = 6.7 Hz, 2H), 3.51 (d, J = 4.9 Hz, 4H), 3.26 (s, 3H), 2.94-2.88 (m, 3H), 1.15 (t, J = 7.0 Hz, 3H) |
| 73 | ¹H NMR (500 MHz, DMSO-d₆) δ 10.07 (s, 1H), 9.29 (s, 1H), 9.01 (t, J = 5.5 Hz, 1H), 8.58 (d, J = 3.1 Hz, 1H), 7.94 (s, 1H), 7.48 (d, J = 4.9 Hz, 1H), 5.98 (s, 1H), 4.94-4.75 (m, 1H), 3.33 (quin, J = 6.7 Hz, 2H), 2.98-2.87 (m, 4H), 1.25-1.17 (m, 1H), 1.15 (t, J = 7.0 Hz, 3H), 1.07-0.97 (m, 1H) |
| 74 | ¹H NMR (500 MHz, DMSO-d₆) δ 10.14 (s, 1H), 9.24 (s, 1H), 9.04 (br. s., 1H), 8.37 (d, J = 8.5 Hz, 1H), 7.90 (s, 1H), 7.55 (d, J = 4.3 Hz, 1H), 6.00 (s, 1H), 5.01 (br. s., 2H), 4.24-4.07 (m, 2H), 3.90 (s, 1H), 3.36-3.33 (m, 2H), 3.17 (d, J = 4.9 Hz, 1H), 2.95-2.88 (m, 4H), 1.15 (t, J = 7.0 Hz, 3H) |
| 75 | ¹H NMR (500 MHz, DMSO-d₆) δ 10.13 (br. s., 1H), 9.25 (br. s., 2H), 9.02 (br. s., 1H), 7.97 (br. s., 2H), 7.78 (br. s., 1H), 7.66 (br. s., 1H), 7.52 (br. s., 1H), 6.59 (br. s., 1H), 6.00 (br. s., 1H), 2.91 (br. s., 3H), 2.74 (br. s., 2H), 1.15 (br. s., 3H) |

| Compound | ¹H NMR |
|---|---|
| 76 | ¹H NMR (500 MHz, DMSO-d₆) δ 10.13 (br. s., 1H), 9.24 (br. s., 1H), 9.02 (br. s., 1H), 8.61 (br. s., 1H), 7.89 (br. s., 1H), 7.50 (br. s., 1H), 5.96 (br. s., 1H), 5.11 (br. s., 2H), 3.34 (br. s., 4H), 2.91 (br. s., 4H), 1.15 (d, J = 7.3 Hz, 3H) |
| 77 | ¹H NMR (500 MHz, DMSO-d₆) δ 8.88 (s, 1H), 8.64 (d, J = 3.1 Hz, 1H), 8.21 (d, J = 4.3 Hz, 1H), 7.85 (s, 1H), 7.78 (s, 1H), 7.43 (d, J = 4.9 Hz, 1H), 7.19 (s, 1H), 6.04 (s, 1H), 2.92-2.82 (m, 4H), 2.77 (d, J = 4.3 Hz, 3H), 0.76 (d, J = 5.5 Hz, 2H), 0.51 (br. s., 2H) |

Example 78

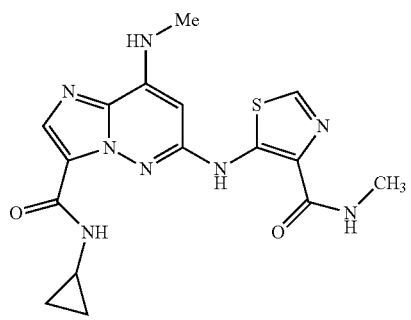

Example 78

78a

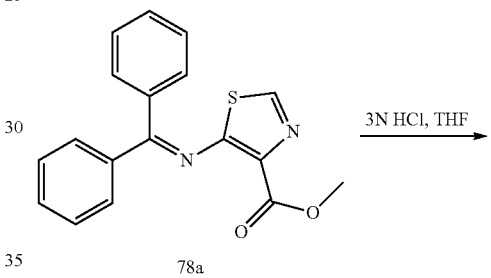

78a

A mixture of methyl 5-bromothiazole-4-carboxylate (1.14 g, 5.13 mmol), benzophenone imine (1.287 ml, 7.70 mmol), cesium carbonate (3.68 g, 11.29 mmol), xanthphos (0.535 g, 0.924 mmol) and tris(dibenzylideneacetone)dipalladium-chloroform ddduct (0.292 g, 0.282 mmol) in toluene (12 mL) was heated to 80° C. overnight. After stirring overnight, the reaction was cooled to room temperature. Analysis by LC-MS indicated reaction was complete. After evaporating away most of the toluene, the crude material was suspended in 150 mL DCM and the insoluble cesium carbonate was filtered off. The resulting solution was then concentrated and was purified by flash chromatography eluting with 0-100% EtOAc in hexanes on an 80 g column. Clean fractions were concentrated to afford methyl 5-((diphenylmethylene)amino)thiazole-4-carboxylate (1.55 g, 4.81 mmol, 94% yield) (78a) as a yellow oil. LC retention time 0.98 min [A]. MS (E+) m/z: 323 (MH⁺).

78b

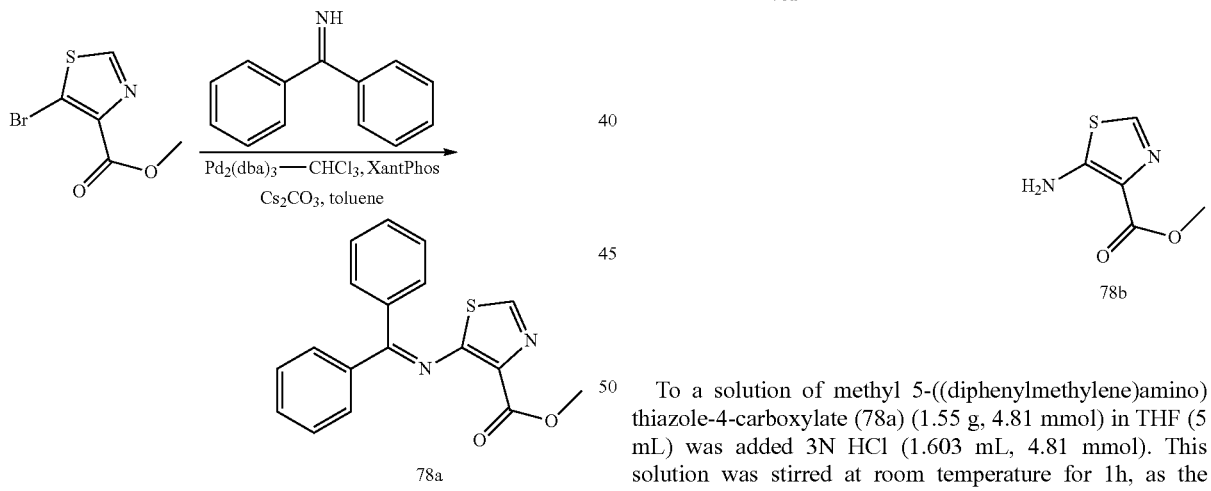

To a solution of methyl 5-((diphenylmethylene)amino)thiazole-4-carboxylate (78a) (1.55 g, 4.81 mmol) in THF (5 mL) was added 3N HCl (1.603 mL, 4.81 mmol). This solution was stirred at room temperature for 1h, as the product began to precipitate out of solution. After filtering off an off-white solid, it was partitioned this between EtOAc and saturated aqueous sodium bicarbonate. The aqueous layer was extracted with EtOAc twice. The combined organic layers were washed with brine. After drying over sodium sulfate and filtering, the crude material was loaded onto a 24 g column for purification by flash chromatography, eluting with 0-100% EtOAc in hexanes. Concentration of the pure fraction afforded methyl 5-aminothiazole-4-carboxylate (78b) (687 mg, 4.34 mmol, 90% yield) as a white solid. LC retention time 0.46 min [A]. MS (E+) m/z: 159 (MH⁺). ¹H NMR (400 MHz, CHLOROFORM-d) δ 7.88 (s, 1H), 6.01 (br. s., 2H), 1.58 (s, 3H).

78c

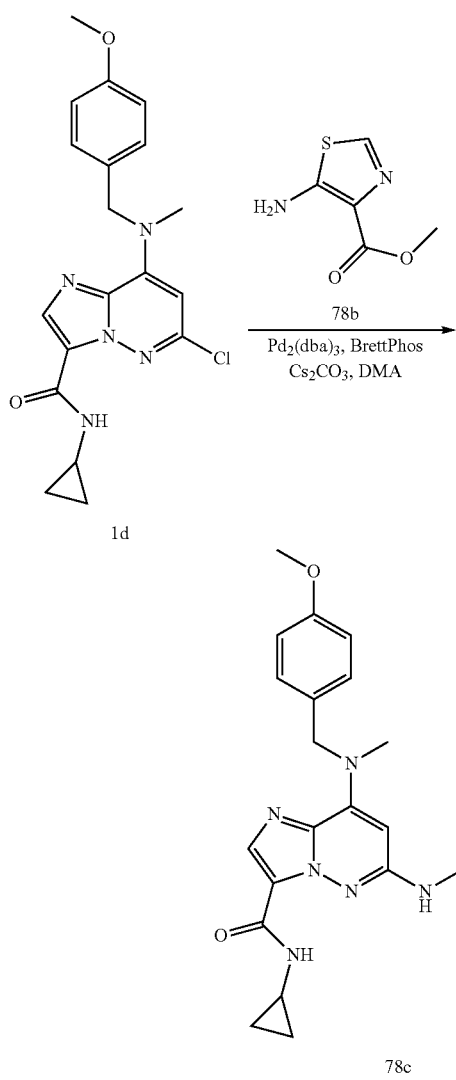

boxylate (78c) (108 mg, 0.202 mmol, 67.8% yield) as a tan solid. LC retention time 0.93 min [A]. MS (E+) m/z: 508 (MH+).

78d

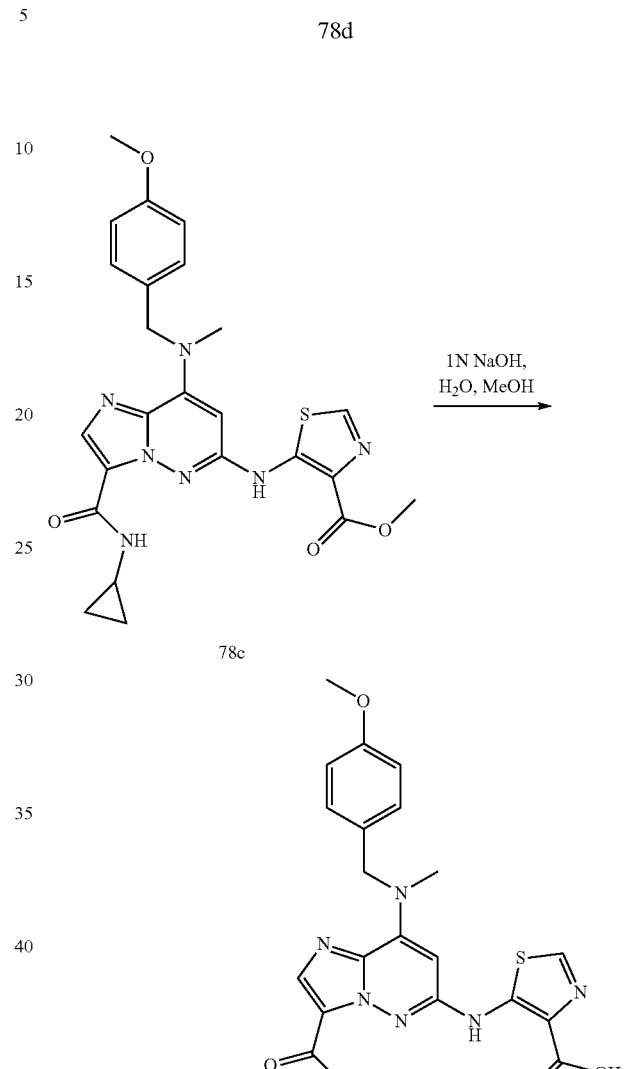

A flask containing a mixture of 6-chloro-N-cyclopropyl-8-((4-methoxybenzyl)(methyl)amino)imidazo[1,2-b]pyridazine-3-carboxamide (1d) (115 mg, 0.298 mmol), methyl 5-aminothiazole-4-carboxylate (78b) (70.7 mg, 0.447 mmol) and BrettPhos (40.0 mg, 0.075 mmol) was flushed with nitrogen. DMA (2.5 mL) was added and the heterogeneous mixture was sparged with nitrogen for a few minutes. Cesium carbonate (388 mg, 1.192 mmol) was added, followed by Pd$_2$dba$_3$ (68.2 mg, 0.075 mmol) and the resulting mixture was heated to 90° C. for 72 hours. After the reaction was complete, the reaction was cooled to room temperature. Analysis by LC-MS indicated that the reaction was complete. 15 mL water was added, and the slurry was extracted with EtOAc (3×40 ml). The combined EtOAc layers were washed 10% LiCl (40 ml) and brine (40 ml). Drying over sodium sulfate filtration and concentration afforded a residue that was purified by flash chromatography eluting with 0-100% EtOAc in hexanes on a 12 g column. Clean fractions were concentrated to afford methyl 5-((3-(cyclopropylcarbamoyl)-8-((4-methoxybenzyl)(methyl)amino)imidazo[1,2-b]pyridazin-6-yl)amino)thiazole-4-car- To a solution of methyl 5-((3-(cyclopropylcarbamoyl)-8-((4-methoxybenzyl)(methyl)amino)imidazo[1,2-b]pyridazin-6-yl)amino)thiazole-4-carboxylate (78c) (88 mg, 0.173 mmol) in THF (1.5 mL) and methanol (0.15 mL) was added 1N NaOH (2.081 mL, 2.081 mmol). The resulting solution was stirred at 50° C. overnight. After stirring overnight, water (15 ml) was added, followed by 2.2 mL 1N HCl to acidify the reaction. The resulting mixture was extracted with EtOAc (3×) and the combined organic layers were dried over sodium sulfate. Filtration and concentration afforded 5-((3-(cyclopropylcarbamoyl)-8-((4-methoxybenzyl)(methyl)amino)imidazo[1,2-b]pyridazin-6-yl)amino)thiazole-4-carboxylic acid (78d) (79 mg, 0.152 mmol, 88% yield). as a white solid. LC retention time 0.83 min [A]. MS (E+) m/z: 494 (MH+).

Example 78

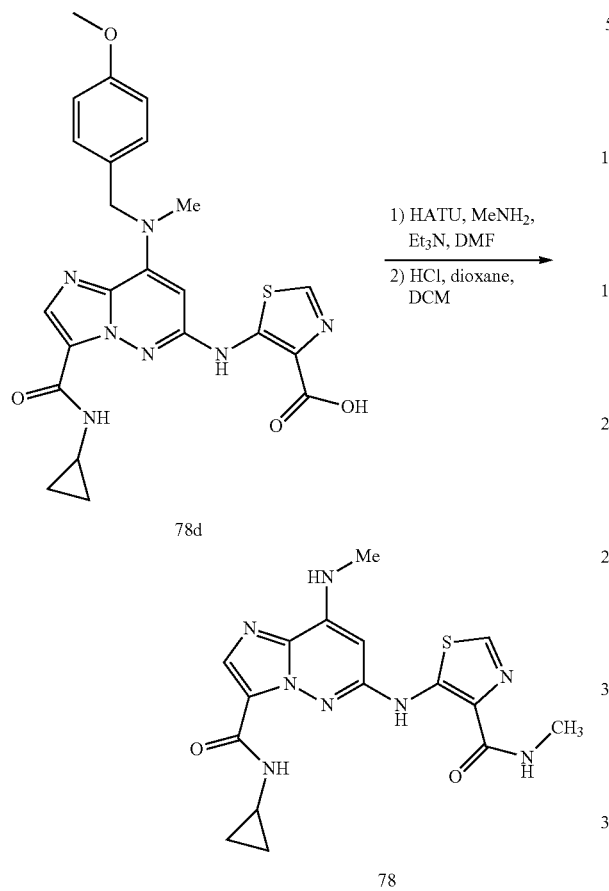

A mixture of 5-((3-(cyclopropylcarbamoyl)-8-((4-methoxybenzyl)(methyl)amino)imidazo[1,2-b]pyridazin-6-yl)amino)thiazole-4-carboxylic acid (78d) (13 mg, 0.026 mmol), methanamine, HCl (2.454 mg, 0.079 mmol), BOP (23.30 mg, 0.053 mmol) and DIEA (0.028 mL, 0.158 mmol) in DMF (1 mL) was stirred at room temperature for one hour whereupon the reaction was complete by LC-MS. The reaction mixture was concentrated to a pale yellow solid. To a solution of this crude 5-((3-(cyclopropylcarbamoyl)-8-((4-methoxybenzyl)(methyl)amino)imidazo[1,2-b]pyridazin-6-yl)amino)-N-methylthiazole-4-carboxamide (13 mg, 0.026 mmol) in DCM (1 mL) was added 4N HCl in 1,4-dioxane (0.096 mL, 0.385 mmol). This solution was stirred at room temperature for 30 minutes. The volatiles were removed and the residue was purified via preparative LC/MS with the following conditions: Column: Waters XBridge C18, 19×250 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 5-100% B over 25 minutes, then a 5-minute hold at 100% B; Flow: 20 mL/min. Fractions containing the desired product were combined and dried via centrifugal evaporation to afford 5-((3-(cyclopropylcarbamoyl)-8-(methylamino)imidazo[1,2-b]pyridazin-6-yl)amino)-N-methylthiazole-4-carboxamide (77) (3.8 mg, 9.44 μmol, 36.8% yield). LC retention time 1.18 min [D]. MS (E+) m/z: 387. $^1$H NMR (500 MHz, DMSO-$d_6$) δ 11.19 (s, 1H), 8.69 (s, 1H), 8.53-8.45 (m, 2H), 7.90 (s, 1H), 7.72 (d, J=4.9 Hz, 1H), 6.15 (s, 1H), 2.95-2.88 (m, 4H), 2.84 (d, J=4.9 Hz, 3H), 0.87-0.81 (m, 2H), 0.67 (d, J=2.4 Hz, 2H).

The following examples were prepared in a similar manner to Example 78.

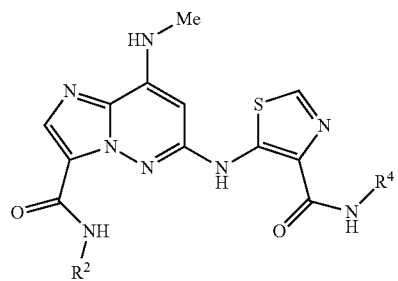

| Example number | R² | R⁴ | Rt (min) [Method] | m/z [M + H]⁺ |
|---|---|---|---|---|
| 79 | cyclopropyl | ethyl | 1.35 [D] | 401 |
| 80 | cyclopropyl | n-propyl | 1.52 [D] | 415 |
| 81 | cyclopropyl | isopropyl | 1.53 [D] | 415 |
| 82 | cyclopropyl | benzyl | 1.78 [D] | 449 |
| 83 | cyclopropyl | (pyridin-3-yl)methyl | 0.95 [D] | 450 |

| Compound | $^1$H NMR |
|---|---|
| 79 | $^1$H NMR (500 MHz, DMSO-$d_6$) δ 11.12 (s, 1H), 8.64 (s, 1H), 8.50 (br. s., 2H), 7.91-7.84 (m, 1H), 7.62 (br. s., 1H), 6.10 (s, 1H), 2.90 (d, J = 4.3 Hz, 2H), 2.88 (bs, 4H), 1.13 (t, J = 7.0 Hz, 3H), 0.84 (d, J = 5.5 Hz, 2H), 0.64 (br. s., 2H) |
| 80 | $^1$H NMR (500 MHz, DMSO-$d_6$) δ 11.21 (s, 1H), 8.69 (s, 1H), 8.53 (t, J = 6.1 Hz, 1H), 8.47 (d, J = 2.4 Hz, 1H), 7.90 (s, 1H), 7.71 (d, J = 5.5 Hz, |

-continued

| Compound | ¹H NMR |
|---|---|
|  | 1H), 6.17 (s, 1H), 3.27 (q, J = 6.7 Hz, 2H), 2.94-2.87 (m, 4H), 1.57 (sxt, J = 7.3 Hz, 2H), 0.89 (t, J = 7.3 Hz, 3H), 0.86-0.81 (m, 2H), 0.69-0.64 (m, 2H) |
| 81 | ¹H NMR (500 MHz, DMSO-d₆) δ 11.19 (s, 1H), 8.69(s, 1H), 8.47 (d, J = 3.1 Hz, 1H), 8.20 (d, J = 8.5 Hz, 1H), 7.90 (s, 1H), 7.71 (d, J = 4.9 Hz, 1H), 6.17 (s, 1H), 4.22-4.12 (m, 1H), 2.96-2.87 (m, 4H), 1.22 (d, J = 6.7 Hz, 6H), 0.86-0.82 (m, 2H), 0.69-0.64 (m, 2H) |
| 82 | ¹H NMR (500 MHz, DMSO-d₆) δ 10.99(s, 1H), 10.28 (s, 1H), 8.79(s, 1H), 8.48 (d, J = 3.1 Hz, 1H), 7.92(s, 1H), 7.87 (d, J = 7.9 Hz, 2H), 7.74 (d, J = 4.3 Hz, 1H), 7.37 (t, J = 7.6 Hz, 2H), 7.16-7.10 (m, 1H), 6.30 (s, 1H), 2.97-2.88 (m, 4H), 0.85 (d, J = 5.5 Hz, 2H), 0.68 (br. s., 2H) |
| 83 | ¹H NMR (500 MHz, DMSO-d₆) δ 10.90(s, 1H), 10.58 (s, 1H), 9.05 (s, 1H), 8.79 (s, 1H), 8.48 (br. s., 1H), 8.33 (d, J = 4.3 Hz, 1H), 8.25 (d, J = 7.9 Hz, 1H), 7.92 (s, 1H), 7.74 (d, J = 4.9 Hz, 1H), 7.42 (dd, J = 8.5, 4.9 Hz, 1H), 6.31 (s, 1H), 2.97-2.90 (m, 4H), 0.85 (d, J = 5.5 Hz, 2H), 0.67 (br. s., 2H) |

Example 84

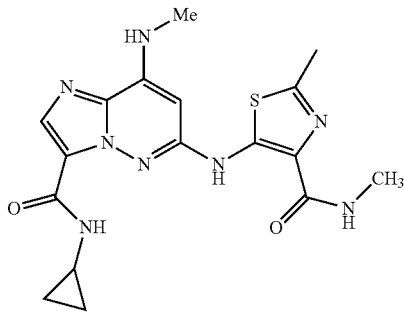

84a

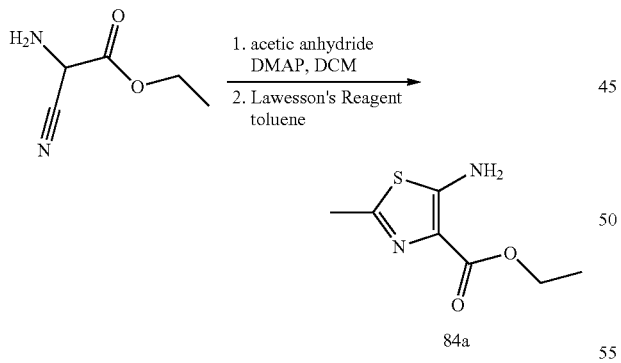

Ethyl 2-amino-2-cyanoacetate, p-toluenesulfonate salt (1 g, 3.34 mmol) was free-based by dissolving it in 10 mL saturated aqueous sodium bicarbonate, then extracting with dichloromethane (3×10 ml). The combined dichloromethane layers were dried overs sodium sulfate, filtered and concentrated to ~25 mL volume. To this solution was added N,N-dimethylaminopyridine (0.041 g, 0.334 mmol), followed by acetic anhydride (0.347 mL, 3.67 mmol). After the stirring 1 h at room temperature, the reaction mixture was quenched with 5 ml of sat. aq. sodium bicarbonate, and 5 ml of water. The reaction mixture was extracted with DCM (3×25 ml). The combined DCM layers were dried over sodium sulfate, filtered and concentrated to afford the crude product, ethyl 2-acetamido-2-cyanoacetate (0.51 g, 3.00 mmol, 90% yield) as a yellow solid. A portion of this material (334 mg, 1.963 mmol) was then dissolved in toluene (7 mL). To this solution was added Lawesson's reagent (397 mg, 0.981 mmol) and the resulting mixture was stirred at 80° C. overnight. After cooling to room temperature, the reaction mixture was evaporated onto Celite. The material was purified first by 24 g silica gel column, eluting with 0-100% EtOAc in hexanes, and then by a second 24 g silica gel column purification, eluting with 0-10% MeOH in DCM. Concentration of the pure fractions afforded ethyl 5-amino-2-methylthiazole-4-carboxylate (84a) (35 mg, 0.188 mmol, 10% yield) as a colorless oil. LC retention time 0.54 min [A]. MS (E+) m/z: 187 (MH⁺). ¹H NMR (400 MHz, CHLOROFORM-d) δ 6.03-5.76 (m, 2H), 4.39 (q, J=7.0 Hz, 2H), 2.60-2.51 (m, 3H), 1.45-1.37 (m, 3H).

84b

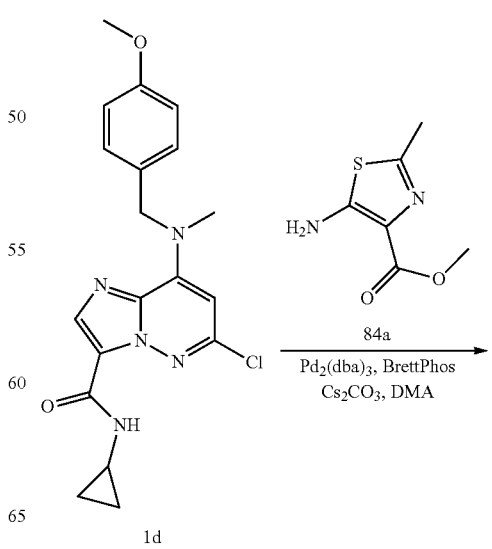

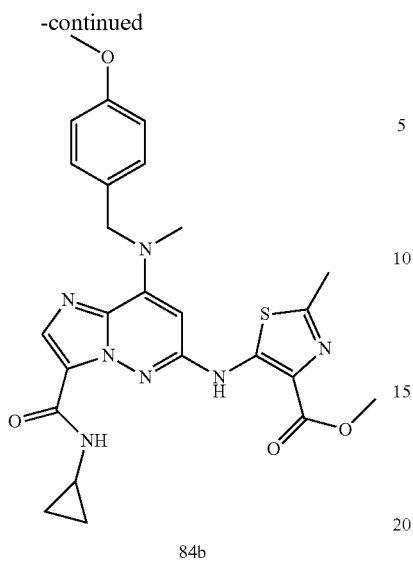

84b

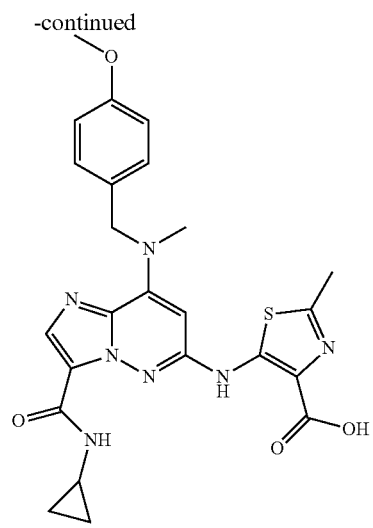

84c 6-chloro-N-cyclopropyl-8-((4-methoxybenzyl)(methyl) amino)imidazo[1,2-b]pyridazine-3-carboxamide (1d) (44 mg, 0.114 mmol), ethyl 5-amino-2-methylthiazole-4-carboxylate (84a) (31.9 mg, 0.171 mmol), and BrettPhos (12.24 mg, 0.023 mmol) were added to a flask and that was subsequently flushed with nitrogen. N,N-dimethylacetamide (1 mL) was added and the heterogeneous mixture was sparged with nitrogen for a few minutes. Cesium carbonate (111 mg, 0.342 mmol) and Pd2dba3 (20.88 mg, 0.023 mmol) were added, and the resulting mixture was then heated to 115° C. overnight. After cooling to rt, water (15 ml) was added and the resulting mixture was extracted with EtOAc (3×40 ml). The combined organic layers were washed with 10% LiCl (40 ml), brine (40 ml), dried over sodium sulfate. This solution was filtered, concentrated, and purified by flash chromatography eluting with 0-100% EtOAc in hexanes on a 12 g column. The clean fractions were concentrated to afford ethyl 5-((3-(cyclopropylcarbamoyl)-8-((4-methoxybenzyl)(methyl)amino)imidazo[1,2-b] pyridazin-6-yl)amino)-2-methylthiazole-4-carboxylate (84b) (51 mg, 0.095 mmol, 83% yield) as a tan solid. LC retention time 0.98 min [A]. MS (E+) m/z: 536 (MH+).

84c

To a solution of ethyl 5-((3-(cyclopropylcarbamoyl)-8-((4-methoxybenzyl) (methyl)amino)imidazo[1,2-b] pyridazin-6-yl)amino)-2-methylthiazole-4-carboxylate (84b) (50 mg, 0.093 mmol) in THF (1 mL) and methanol (0.1 mL) was added 1N NaOH (0.467 mL, 0.467 mmol), and the resulting solution was stirred at room temperature overnight at 40° C. Upon cooling to rt, the reaction mixture was acidified with 1 mL 1N HCl. The resulting mixture was then extracted with EtOAc (2×). The combined organics were washed with brine and dried over sodium sulfate. Filtration and evaporation afforded 5-((3-(cyclopropylcarbamoyl)-8-((4-methoxybenzyl)(methyl) amino)imidazo[1,2-b] pyridazin-6-yl)amino)-2-methylthiazole-4-carboxylic acid (84c) (37 mg, 0.073 mmol, 78% yield) as a light brown solid. LC retention time 0.85 min [A]. MS (E+) m/z: 508 (MH+).

Example 84

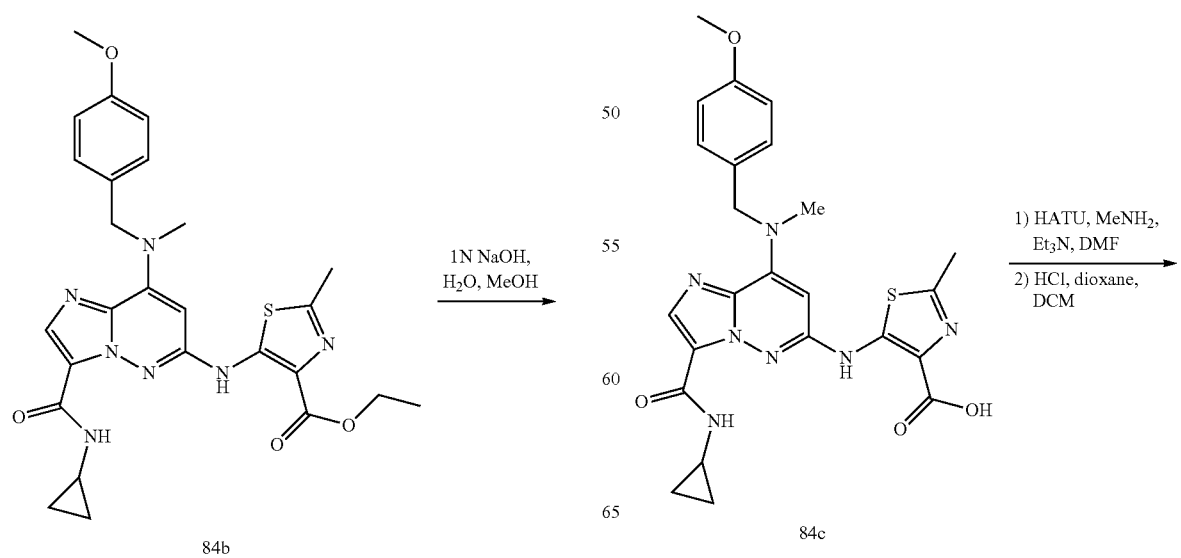

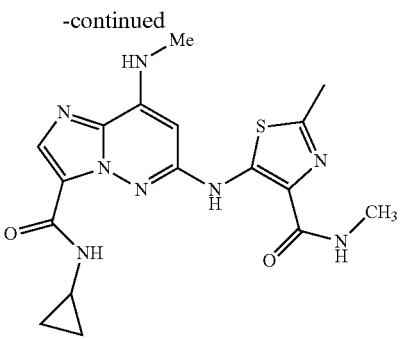

84

A mixture of 5-((3-(cyclopropylcarbamoyl)-8-((4-methoxybenzyl)(methyl) amino)imidazo[1,2-b]pyridazin-6-yl)amino)-2-methylthiazole-4-carboxylic acid (13 mg, 0.026 mmol), methylamine hydrochloride (5.19 mg, 0.077 mmol), BOP (22.66 mg, 0.051 mmol) and N,N-diisopropylethylamine (0.027 mL, 0.154 mmol) in DMF (1 mL) was stirred at room temperature for 30 minutes, whereupon the reaction was complete by LC-MS. The reaction mixture was concentrated to a pale yellow solid. To a solution of this crude 5-((3-(cyclopropylcarbamoyl)-8-((4-methoxybenzyl)(methyl)amino)imidazo[1,2-b]pyridazin-6-yl)amino)-N,2-dimethylthiazole-4-carboxamide (13 mg, 0.025 mmol) in DCM (1 mL) was added 4N HCl in 1,4-dioxane (0.094 mL, 0.375 mmol). This solution was stirred at room temperature for 30 minutes. The volatiles were removed and the residue was purified via preparative LC/MS with the following conditions: Column: Waters XBridge C18, 19×250 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 5-100% B over 25 minutes, then a 5-minute hold at 100% B; Flow: 20 mL/min. Fractions containing the desired product were combined and dried via centrifugal evaporation to afford 5-((3-(cyclopropylcarbamoyl)-8-(methylamino) imidazo[1,2-b]pyridazin-6-yl)amino)-N,2-dimethylthiazole-4-carboxamide (84) (1.26 mg, 2.93 μmol, 11.72% yield). LC retention time 1.24 min [D]. MS (E+) m/z: 401 (MH$^+$). $^1$H NMR (500 MHz, DMSO-d$_6$) δ 11.08 (s, 1H), 8.50 (d, J=2.4 Hz, 1H), 8.32 (d, J=4.3 Hz, 1H), 7.90 (s, 1H), 7.70 (d, J=4.9 Hz, 1H), 6.11 (s, 1H), 3.90 (s, 1H), 3.17 (d, J=5.5 Hz, 3H), 2.81 (d, J=4.3 Hz, 3H), 2.64 (s, 3H), 0.90-0.84 (m, 2H), 0.69 (d, J=4.9 Hz, 2H).

Example 85

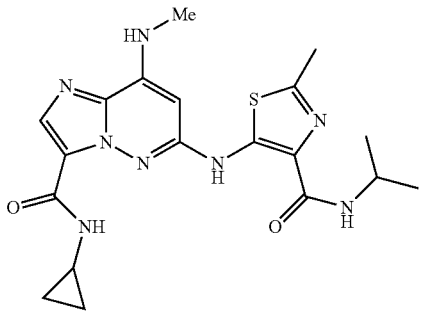

85

Example 85 was prepared in a similar manner to Example 84: LC retention time 1.60 min [D]. MS (E+) m/z: 429 (MH$^+$). $^1$H NMR (500 MHz, DMSO-d$_6$) δ 11.08 (s, 1H), 8.51 (br. s., 1H), 8.01 (d, J=8.5 Hz, 1H), 7.90 (s, 1H), 7.71 (d, J=4.9 Hz, 1H), 6.14 (s, 1H), 4.20-4.10 (m, 1H), 2.96-2.86 (m, 4H), 2.64 (s, 3H), 1.20 (d, J=6.7 Hz, 6H), 0.87 (d, J=4.9 Hz, 2H), 0.69 (br. s., 2H).

Biological Assays

The following assays are used to show the activity for compounds of the invention.

Probe Displacement Assay

The probe displacement assay is conducted as follows: In a 385 well plate, test compounds along with recombinantly expressed His-tagged protein corresponding to amino acids 575-869 of human Tyk2 (sequence shown below) at 2.5 nM, 40 nM ((R)—N-(1-(3-(8-methyl-5-(methylamino)-8H-imidazo[4,5-d]thiazolo[5,4-b]pyridin-2-yl)phenyl)ethyl)-2-([$^3$H]methylsulfonyl)benzamide) (preparation described below) and 80 μg/mL Copper His-Tag scintillation proximity assay beads (Perkin Elmer, Catalog #RPNQ0095) in 50 mM HEPES, pH 7.5, containing 100 μg/mL bovine serum albumin and 5% DMSO were incubated for 30 minutes at room temperature. The amount of radiolabeled probe (preparation described below) bound to Tyk2 was then quantified by scintillation counting, and the inhibition by the test compound calculated by comparison to wells either with no inhibitor (0% inhibition) or without Tyk2 (100% inhibition). The IC50 value is defined as the concentration of test compound required to inhibit radiolabeled probe binding by 50%.

Protein Sequence of recombinant Hig-tagged Tyk2 (575-869):

```
                                              (SEQ ID NO: 1)
MGSSHHHHHH SSGETVRFQG HMNLSQLSFH RVDQKEITQL

SHLGQGTRTN VYEGRLRVEG SGDPEEGKMDDEDPLVPGRD

RGQELRVVLK VLDPSHHDIA LAFYETASLM SQVSHTHLAF

VHGVCVRGPE NIMVTEYVEHGPLDVWLRRE RGHVPMAWKM

VVAQQLASAL SYLENKNLVH GNVCGRNILL ARLGLAEGTS

PFIKLSDPGVGLGALSREER VERIPWLAPE CLPGGANSLS

TAMDKWGFGA TLLEICFDGE APLQSRSPSE

KEHFYQRQHRLPEPSCPQLA TLTSQCLTYE PTQRPSFRTI

LRDLTRL.
```

The preparation of radiolabeled probe, (R)—N-(1-(3-(8-methyl-5-(methylamino)-8H-imidazo[4,5-d]thiazolo[5,4-b]pyridin-2-yl)phenyl)ethyl)-2-([$^3$H]methylsulfonyl)benzamide, was performed as described below:

2-([$^3$H]methylsulfonyl)benzoic acid

2-Mercaptobenzoic acid (2.3 mg, 0.015 mmol) and cesium carbonate (2 mg, 0.006 mmol) were added to a 5 mL round-bottomed flask. The flask was attached to a ported glass vacuum line and anhydrous DMF (0.5 mL) was introduced with magnetic stirring. An ampoule of tritiated methyl iodide (200 mCi, Perkin-Elmer lot 3643419) was added to the reaction flask and stirring was maintained at rt for 3 h. In-process HPLC analysis with radiometric detection indicated 80% conversion to the desired product by comparison with authentic standard. Without purification, the crude product was reacted with mCPBA (10 mg, 0.058 mmol) pre-dissolved in $CH_2Cl_2$ (1 mL) at room temperature with stirring. The reaction was stirred for 7 h and additional mCPBA (10 mg, 0.058 mmol) was added. The reaction was stirred for approximately 24 h and HPLC analysis indicated 35-40% conversion to the desired sulfonate product. The crude product was purified by semi-preparative HPLC (Luna 5 um C18 (10×250 cm); A: MeOH/$H_2O$=15/85 (0.1% TFA); B: MeOH; 270 nm; 0-8 min 0% B 1 ml/min; 8-10 min 0% B 1-3 ml/min; 10-55 min 0% B 3 ml/min; 55-65 min 0-10% B 3 ml/min; 65-75 min 10-50% B 3 ml/min; 75-80 min 50-100% B 3 ml/min) to give 81 mCi (40% radiochemical yield) of 2-([$^3$H]methylsulfonyl)benzoic acid product identified by its HPLC co-elution with an authentic standard. The radiochemical purity was measured by HPLC to be 99% (Luna 5u C18 (4.6×150 cm); A: $H_2O$ (0.1% TFA); B: MeOH; 1.2 ml/min; 270 nm; 0-10 min 20% B; 10-15 min 20-100% B; 15-25 min 100% B. The product was dissolved in anhydrous acetonitrile to give a final solution activity of 5.8 mCi/mL. (R)—N-(1-(3-(8-methyl-5-(methylamino)-8H-imidazo[4,5-d]thiazolo[5,4-b]pyridin-2-yl)phenyl)ethyl)-2-([$^3$H]methylsulfonyl)benzamide: A solution of 2-([$^3$H]methylsulfonyl)benzoic acid (23.2 mCi) in acetonitrile was added to a 5 mL round-bottomed flask which was then attached to a vacuum line and carefully evaporated to dryness. (R)-2-(3-(1-aminoethyl)phenyl)-N,8-dimethyl-8H-imidazo[4,5-d]thiazolo[5,4-b]pyridin-5-amine (prepared as described in WO 2004/106293 and Dyckman et al., *Bioorganic and Medicinal Chemistry Letters*, 383-386 (2011)) (1.1 mg, 0.0033 mmol) and PyBOP (2 mg, 0.0053 mmol) dissolved in anhydrous DMF (1.5 mL) were added to the flask followed by N,N-diisopropylethylamine (0.010 mL). The resulting clear solution was stirred at room temperature for 18 h. HPLC analysis (Luna 5u C18 (4.6×150 cm); A: $H_2O$ (0.1% TFA); B: MeOH; 1.2 ml/min; 335 nm; 0-20 min 50% B; 20-25 min 50-100% B; 25-30 min 100% B) indicated approximately a 20% conversion to the desired product by retention time comparison to a sample of non-radiolabeled (R)—N-(1-(3-(8-methyl-5-(methylamino)-8H-imidazo[4,5-d]thiazolo[5,4-b]pyridin-2-yl)phenyl)ethyl)-2-(methylsulfonyl)benzamide. The crude reaction mixture was purified by semi-preparative HPLC (Luna 5u C18 (10×250 cm); A: MeOH/$H_2O$=50/50 (0.1% TFA); B: MeOH; 335 nm; 0-40 min 0% B 3 ml/min; 40-45 min 0-100% B 3 ml/min). The purification routine was performed a second time to yield a total of 1.7 mCi (7% radiochemical yield) of the desired product in 99.9% radiochemical purity. Mass spectral analysis of the tritiated product (m/z M+H 527.33) was used to establish the specific activity at 80.6 Ci/mmol.

Probe Displacement Data

| Example | Probe Displacement EC50 (uM) |
|---|---|
| 1 | 0.02 |
| 2 | 0.0030 |
| 3 | |
| 4 | 7.60E−03 |
| 5 | 0.01 |
| 6 | 3.84E−03 |
| 7 | 0.02 |
| 8 | 7.67E−03 |
| 9 | 0.03 |
| 10 | 0.03 |
| 11 | 0.02 |
| 12 | 7.59E−03 |
| 13 | 7.77E−03 |
| 14 | 0.01 |
| 15 | 9.37E−03 |
| 16 | 4.49E−03 |
| 17 | 0.04 |
| 18 | 0.05 |
| 19 | 0.10 |
| 20 | 0.03 |
| 21 | 0.05 |
| 22 | 0.02 |
| 23 | 0.02 |
| 24 | 8.40E−03 |
| 25 | 8.89E−03 |
| 26 | |
| 27 | 6.80E−03 |
| 28 | 0.02 |
| 29 | 0.10 |
| 30 | |
| 31 | 9.39E−03 |
| 32 | 3.00E−02 |
| 33 | 3.00E−02 |
| 34 | 2.47E−03 |
| 35 | 4.83E−03 |
| 36 | 0.13 |
| 37 | 0.05 |
| 38 | 0.05 |
| 39 | 1.27 |
| 40 | 0.08 |
| 41 | 0.03 |
| 42 | 0.36 |
| 43 | 0.49 |
| 44 | 0.01 |
| 45 | 0.02 |
| 46 | 8.00E−03 |
| 47 | 5.13E−03 |
| 48 | 0.02 |
| 49 | 0.04 |
| 50 | 0.03 |
| 51 | 3.79E−03 |
| 52 | 6.73E−03 |
| 53 | 2.82E−03 |
| 54 | 6.06E−03 |
| 55 | 2.87E−03 |
| 56 | 2.08E−03 |
| 57 | 2.73E−03 |
| 58 | 3.61E−03 |
| 59 | 1.93E−03 |
| 60 | 0.002695 |
| 61 | |
| 62 | 9.30E−03 |
| 63 | 6.04E−03 |
| 64 | 1.99E−03 |
| 65 | 0.03 |
| 66 | 0.01 |
| 67 | 0.04 |
| 68 | 2.78E−03 |
| 69 | 2.29E−03 |
| 70 | 0.02 |
| 71 | 8.09E−03 |
| 72 | 5.78E−03 |
| 73 | 0.02 |
| 74 | 7.25E−03 |
| 75 | 0.01 |
| 76 | |
| 77 | 0.02 |
| 78 | 0.01 |
| 79 | 0.02 |
| 80 | 0.02 |
| 81 | 3.24E−03 |
| 82 | 3.95E−03 |
| 83 | 0.01 |
| 84 | 4.51E−03 |
| 85 | 0.02666 |

Kit225 T Cell Assay

Kit225 T cells with a stably-integrated STAT-dependent luciferase reporter were plated in RPMI (GIBCO) containing 10% heat-inactivated FBS (GIBCO) and 100 U/mL PenStrep (GIBCO). The cells were then stimulated with either 20 ng/mL human recombinant IL-23 or 200 U/mL human recombinant IFNα (PBL InterferonSource) for 5-6 hours. Luciferase expression was measured using the STEADY-GLO® Luciferase Assay System (PROMEGA®) according to the manufacturer's instructions. Inhibition data were calculated by comparison to no inhibitor control wells for 0% inhibition and non-stimulated control wells for 100% inhibition. Dose response curves were generated to determine the concentration required to inhibit 50% of cellular response (IC50) as derived by non-linear regression analysis.

| Kit225 T Cell Inhibition Data | | |
|---|---|---|
| Ex. # | IL-23 Kit225 Reporter, LE (IC50, uM) | IFNa Kit225 Reporter, LE (IC50, uM) |
| 1 | 1.32 | 0.37 |
| 2 | 0.94 | 0.68 |
| 3 | 1.21 | 1.52 |
| 4 | 0.35 | 0.24 |
| 5 | 0.34 | 0.07 |
| 6 | 0.07 | 0.19 |
| 7 | 0.32 | 0.19 |
| 8 | 0.26 | 0.22 |
| 9 | 0.65 | 0.48 |
| 10 | 0.96 | 0.40 |
| 11 | 0.52 | 0.48 |
| 12 | 0.12 | 0.11 |
| 13 | 0.33 | 0.21 |
| 14 | 0.28 | 0.25 |
| 15 | 0.20 | 0.11 |
| 16 | 0.25 | 0.14 |
| 17 | 0.16 | 0.49 |
| 18 | 0.47 | 0.77 |
| 19 | 0.59 | 12.50 |
| 20 | 1.12 | 0.81 |
| 21 | 0.24 | 0.50 |
| 22 | 0.27 | 0.35 |
| 23 | 0.43 | 0.81 |
| 24 | 0.28 | 0.34 |
| 25 | 0.13 | 0.19 |
| 26 | 0.64 | 0.42 |
| 27 | 0.02 | 0.16 |
| 28 | 0.21 | 0.40 |
| 29 | 0.24 | 1.04 |
| 30 | 0.65 | 0.18 |
| 31 | 0.72 | 0.30 |
| 32 | 0.83 | 1.65 |
| 33 | 1.00 | 5.82 |
| 34 | 0.58 | 0.81 |
| 35 | 1.09 | 0.47 |
| 36 | 3.33 | 11.93 |
| 37 | 2.34 | 1.39 |
| 38 | 4.46 | 12.50 |
| 39 | 12.50 | 12.50 |
| 40 | 12.50 | 12.50 |
| 41 | 12.50 | 12.50 |
| 42 | 12.50 | 12.50 |
| 43 | 16.14 | 12.50 |
| 44 | 0.14 | 0.07 |
| 45 | 0.22 | 0.13 |
| 46 | 0.10 | 0.12 |
| 47 | 0.06 | 0.05 |
| 48 | 0.15 | 0.08 |
| 49 | 0.27 | 0.26 |
| 50 | 0.45 | 1.00 |
| 51 | 0.05 | 0.04 |
| 52 | 0.10 | 0.06 |
| 53 | 0.06 | 0.07 |
| 54 | 0.17 | 0.05 |
| 55 | 0.06 | 0.03 |
| 56 | 0.03 | 0.02 |
| 57 | 0.05 | 0.10 |
| 58 | 0.15 | 0.11 |
| 59 | 0.01 | 0.03 |
| 60 | 0.2115 | 0.06623 |
| 61 | 0.17 | 0.25 |
| 62 | 0.54 | 0.18 |
| 63 | | 0.29 |
| 64 | 0.08 | 0.06 |
| 65 | 0.75 | 0.49 |
| 66 | 0.40 | 0.11 |
| 67 | 0.47 | 0.23 |
| 68 | 0.14 | 0.05 |
| 69 | 0.05 | 0.01 |
| 70 | 0.42 | 0.11 |
| 71 | 0.20 | 0.21 |
| 72 | 0.14 | 0.07 |
| 73 | 0.16 | 0.20 |
| 74 | 0.07 | 0.02 |
| 75 | 3.31 | 2.29 |
| 76 | 0.06 | 0.15 |
| 77 | 0.57 | 0.22 |
| 78 | 0.12 | 0.26 |
| 79 | 0.32 | 0.15 |
| 80 | 0.14 | 0.13 |
| 81 | 0.30 | 0.31 |
| 82 | 0.19 | 0.35 |
| 83 | 0.16 | 1.76 |
| 84 | 0.11 | 0.18 |
| 85 | 0.2556 | 0.2238 |
| 86 | 0.27 | 0.39 |

What is claimed is:

1. A compound of formula (I)

wherein
- A is a 5 membered heteroaryl group containing 1-2 heteroatoms independently selected from —N—, —O— or —S— substituted with 0-2 $R^x$;
- $R^x$ is H or $C_1$-$C_6$ alkyl;
- $R^1$ is H, $C_1$-$C_6$ alkyl, $C_3$-$C_8$ cycloalkyl, hydroxy $C_1$-$C_6$ alkyl or alkoxy $C_1$-$C_6$ alkyl;
- $R^2$ is H, $C_1$-$C_6$ alkyl, $C_3$-$C_8$ cycloalkyl, hydroxy $C_1$-$C_6$ alkyl, alkoxy $C_1$-$C_6$ alkyl, $C_3$-$C_8$ cycloalkyl $C_1$-$C_6$ alkyl-, di ($C_1$-$C_4$) alkyl aminoalkyl-, aryl, heteroaryl, or heterocyclyl $C_1$-$C_6$ alkyl-, substituted with 0-2 $R^{2a}$;
- $R^{2a}$ is halo or $C_1$-$C_6$ alkyl;
- $R^3$ is H, $C_1$-$C_6$ alkyl, $C_3$-$C_8$ cycloalkyl, hydroxy $C_1$-$C_6$ alkyl or alkoxy $C_1$-$C_6$ alkyl;
- $R^4$ is H, $CD_3$, $C_1$-$C_6$ alkyl, alkoxy $C_1$-$C_6$ alkyl, 3- to 10-membered mono or bicyclic cycloalkyl, 4- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-2 $R^{4a}$;
- $R^{4a}$ is H, $NR^5R^6$, $C_1$-$C_6$ alkyl, $C_3$-$C_8$ cycloalkyl, hydroxy $C_1$-$C_6$ alkyl or alkoxy $C_1$-$C_6$ alkyl;
- $R^5$ and $R^6$ are independently H or $C_1$-$C_4$ alkyl; or
- $R^5$ and $R^6$ are taken together with the nitrogen atom to which they are attached to form a 3-10 membered heterocyclyl ring substituted with 0-2 substituents selected from H, $C_1$-$C_4$ alkyl and OH;

or a pharmaceutically acceptable salt, tautomer or stereoisomer thereof.

2. The compound according to claim 1 of formula II wherein
A is

- $R^x$ is H or $C_1$-$C_6$ alkyl;
- $R^1$ is H, $C_1$-$C_6$ alkyl, $C_3$-$C_8$ cycloalkyl, hydroxy $C_1$-$C_6$ alkyl or alkoxy $C_1$-$C_6$ alkyl;
- $R^2$ is H, $C_1$-$C_6$ alkyl, $C_3$-$C_8$ cycloalkyl, hydroxy $C_1$-$C_6$ alkyl, alkoxy $C_1$-$C_6$ alkyl, $C_3$-$C_8$ cycloalkyl $C_1$-$C_6$ alkyl-, di ($C_1$-$C_4$) alkyl aminoalkyl-, aryl, heteroaryl, or heterocyclyl $C_1$-$C_6$ alkyl-, substituted with 0-2 $R^{2a}$;
- $R^{2a}$ is halo or $C_1$-$C_6$ alkyl;
- $R^3$ is H, $C_1$-$C_6$ alkyl, $C_3$-$C_8$ cycloalkyl, hydroxy $C_1$-$C_6$ alkyl or alkoxy $C_1$-$C_6$ alkyl;
- $R^4$ is H, $CD_3$, $C_1$-$C_6$ alkyl, alkoxy $C_1$-$C_6$ alkyl, 3- to 10-membered mono or bicyclic cycloalkyl, 4- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-2 $R^{4a}$;
- $R^{4a}$ is H, $NR^5R^6$, $C_1$-$C_6$ alkyl, $C_3$-$C_8$ cycloalkyl, hydroxy $C_1$-$C_6$ alkyl or alkoxy $C_1$-$C_6$ alkyl;
- $R^5$ and $R^6$ are independently H or $C_1$-$C_4$ alkyl; or
- $R^5$ and $R^6$ are taken together with the nitrogen atom to which they are attached to form a 3-10 membered heterocyclyl ring substituted with 0-2 substituents selected from H, $C_1$-$C_4$ alkyl and OH;

or a pharmaceutically acceptable salt, tautomer or stereoisomer thereof.

3. The compound according to claim 2

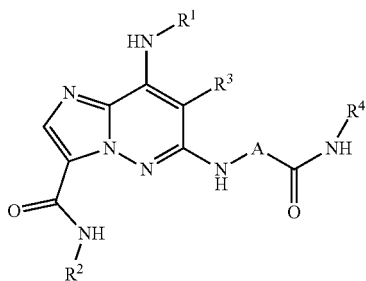

(I)

wherein
A is

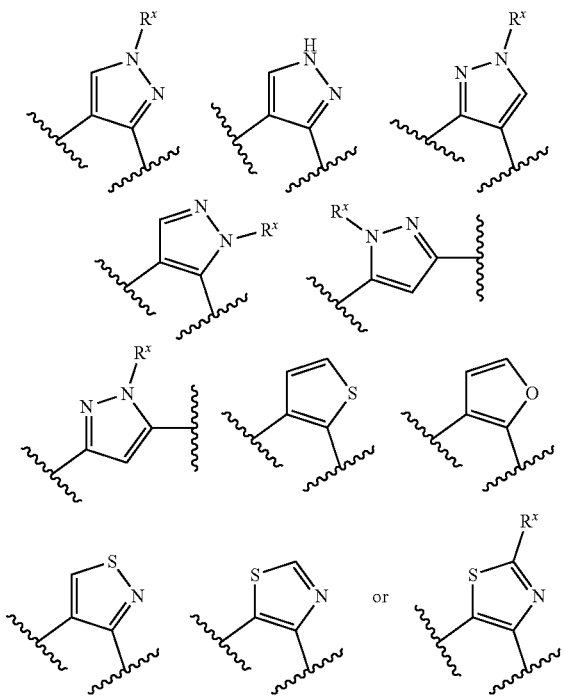

$R^x$ is $C_1$-$C_3$ alkyl;
$R^1$ is H, $C_1$-$C_6$ alkyl, $C_3$-$C_8$ cycloalkyl, hydroxy $C_1$-$C_6$ alkyl or alkoxy $C_1$-$C_6$ alkyl;
$R^2$ is H, $C_1$-$C_6$ alkyl, $C_3$-$C_8$ cycloalkyl, hydroxy $C_1$-$C_6$ alkyl, alkoxy $C_1$-$C_6$ alkyl, $C_3$-$C_8$ cycloalkyl $C_1$-$C_6$ alkyl-, di ($C_1$-$C_4$) alkyl aminoalkyl-, aryl, heteroaryl, or heterocyclyl $C_1$-$C_6$ alkyl-, substituted with 0-2 $R^{2a}$;
$R^{2a}$ is halo or $C_1$-$C_6$ alkyl;
$R^3$ is H, $C_1$-$C_6$ alkyl, $C_3$-$C_8$ cycloalkyl, hydroxy $C_1$-$C_6$ alkyl or alkoxy $C_1$-$C_6$ alkyl;
$R^4$ is H, $CD_3$, $C_1$-$C_6$ alkyl, alkoxy $C_1$-$C_6$ alkyl, 3- to 10-membered mono or bicyclic cycloalkyl, 4- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-2 $R^{4a}$;
$R^{4a}$ is H, $NR^5R^6$, $C_1$-$C_6$ alkyl, $C_3$-$C_8$ cycloalkyl, hydroxy $C_1$-$C_6$ alkyl or alkoxy $C_1$-$C_6$ alkyl;

$R^5$ and $R^6$ are independently H or $C_1$-$C_4$ alkyl; or
$R^5$ and $R^6$ are taken together with the nitrogen atom to which they are attached to form a 3-10 membered heterocyclyl ring substituted with 0-2 substituents selected from H, $C_1$-$C_4$ alkyl and OH;
or a pharmaceutically acceptable salt, tautomer or stereoisomer thereof.

4. The compound according to claim 3

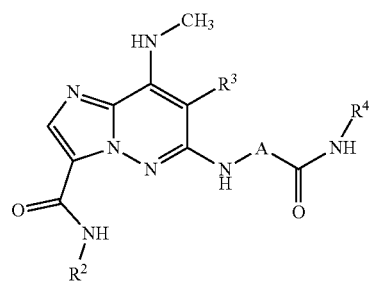

wherein
A is

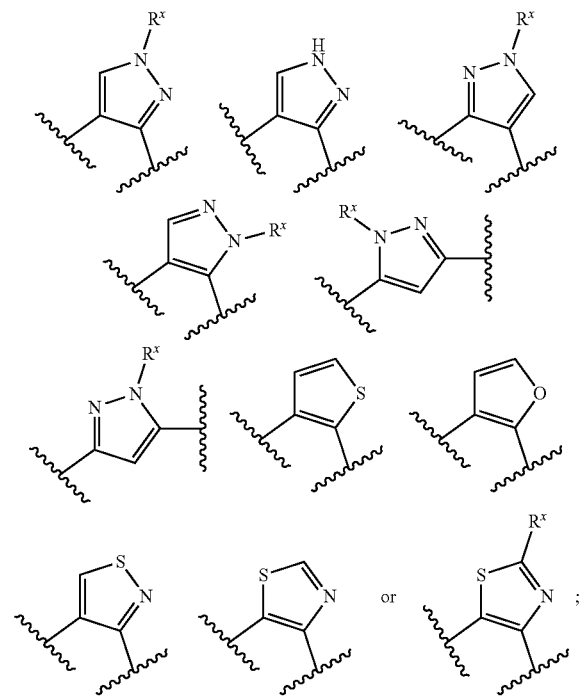

$R^x$ is $C_1$-$C_3$ alkyl;
$R^2$ is H, $C_1$-$C_6$ alkyl, $C_3$-$C_8$ cycloalkyl, hydroxy $C_1$-$C_6$ alkyl, alkoxy $C_1$-$C_6$ alkyl, $C_3$-$C_8$ cycloalkyl $C_1$-$C_6$ alkyl-, di ($C_1$-$C_4$) alkyl aminoalkyl-, aryl, heteroaryl, or heterocyclyl $C_1$-$C_6$ alkyl-, substituted with 0-2 $R^{2a}$;
$R^{2a}$ is halo or $C_1$-$C_6$ alkyl;
$R^3$ is H, $C_1$-$C_6$ alkyl, $C_3$-$C_8$ cycloalkyl, hydroxy $C_1$-$C_6$ alkyl or alkoxy $C_1$-$C_6$ alkyl;
$R^4$ is H, $CD_3$, $C_1$-$C_6$ alkyl, alkoxy $C_1$-$C_6$ alkyl, 3- to 10-membered mono or bicyclic cycloalkyl, 4- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-2 $R^{4a}$;
$R^{4a}$ is H, $NR^5R^6$, $C_1$-$C_6$ alkyl, $C_3$-$C_8$ cycloalkyl, hydroxy $C_1$-$C_6$ alkyl or alkoxy $C_1$-$C_6$ alkyl;
$R^5$ and $R^6$ are independently H or $C_1$-$C_4$ alkyl; or
$R^5$ and $R^6$ are taken together with the nitrogen atom to which they are attached to form a 3-10 membered heterocyclyl ring substituted with 0-2 substituents selected from H, $C_1$-$C_4$ alkyl and OH;
or a pharmaceutically acceptable salt, tautomer or stereoisomer thereof.

5. The compound according to claim 4

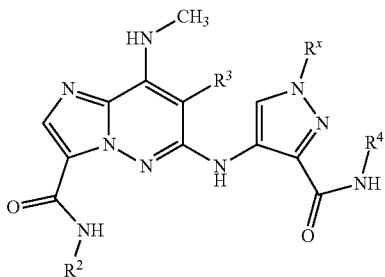

wherein
$R^x$ is $C_1$-$C_3$ alkyl;
$R^2$ is H, $C_1$-$C_6$ alkyl, $C_3$-$C_8$ cycloalkyl, hydroxy $C_1$-$C_6$ alkyl, alkoxy $C_1$-$C_6$ alkyl, $C_3$-$C_8$ cycloalkyl $C_1$-$C_6$ alkyl-, di ($C_1$-$C_4$) alkyl aminoalkyl-, aryl, heteroaryl, or heterocyclyl $C_1$-$C_6$ alkyl-, substituted with 0-2 $R^{2a}$;
$R^{2a}$ is halo or $C_1$-$C_6$ alkyl;
$R^3$ is H, $C_1$-$C_6$ alkyl, $C_3$-$C_8$ cycloalkyl, hydroxy $C_1$-$C_6$ alkyl or alkoxy $C_1$-$C_6$ alkyl;
$R^4$ is H, $CD_3$, $C_1$-$C_6$ alkyl, alkoxy $C_1$-$C_6$ alkyl, 3- to 10-membered mono or bicyclic cycloalkyl, 4- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-2 $R^{4a}$;
$R^{4a}$ is H, $NR^5R^6$, $C_1$-$C_6$ alkyl, $C_3$-$C_8$ cycloalkyl, hydroxy $C_1$-$C_6$ alkyl or alkoxy $C_1$-$C_6$ alkyl;
$R^5$ and $R^6$ are independently H or $C_1$-$C_4$ alkyl; or
$R^5$ and $R^6$ are taken together with the nitrogen atom to which they are attached to form a 3-10 membered heterocyclyl ring substituted with 0-2 substituents selected from H, $C_1$-$C_4$ alkyl and OH;
or a pharmaceutically acceptable salt, tautomer or stereoisomer thereof.

6. The compound according to claim 4

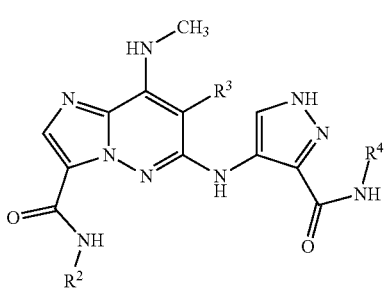

wherein
$R^2$ is H, $C_1$-$C_6$ alkyl, $C_3$-$C_8$ cycloalkyl, hydroxy $C_1$-$C_6$ alkyl, alkoxy $C_1$-$C_6$ alkyl, $C_3$-$C_8$ cycloalkyl $C_1$-$C_6$ alkyl-, di ($C_1$-$C_4$) alkyl aminoalkyl-, aryl, heteroaryl, or heterocyclyl $C_1$-$C_6$ alkyl-, substituted with 0-2 $R^{2a}$;
$R^{2a}$ is halo or $C_1$-$C_6$ alkyl;
$R^3$ is H, $C_1$-$C_6$ alkyl, $C_3$-$C_8$ cycloalkyl, hydroxy $C_1$-$C_6$ alkyl or alkoxy $C_1$-$C_6$ alkyl;
$R^4$ is H, $CD_3$, $C_1$-$C_6$ alkyl, alkoxy $C_1$-$C_6$ alkyl, 3- to 10-membered mono or bicyclic cycloalkyl, 4- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-2 $R^{4a}$;
$R^{4a}$ is H, $NR^5R^6$, $C_1$-$C_6$ alkyl, $C_3$-$C_8$ cycloalkyl, hydroxy $C_1$-$C_6$ alkyl or alkoxy $C_1$-$C_6$ alkyl;
$R^5$ and $R^6$ are independently H or $C_1$-$C_4$ alkyl; or
$R^5$ and $R^6$ are taken together with the nitrogen atom to which they are attached to form a 3-10 membered heterocyclyl ring substituted with 0-2 substituents selected from H, $C_1$-$C_4$ alkyl and OH;
or a pharmaceutically acceptable salt, tautomer or stereoisomer thereof.

7. The compound according to claim 4

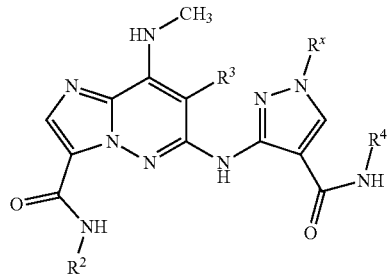

wherein
$R^x$ is $C_1$-$C_3$ alkyl;
$R^2$ is H, $C_1$-$C_6$ alkyl, $C_3$-$C_8$ cycloalkyl, hydroxy $C_1$-$C_6$ alkyl, alkoxy $C_1$-$C_6$ alkyl, $C_3$-$C_8$ cycloalkyl $C_1$-$C_6$ alkyl-, di ($C_1$-$C_4$) alkyl aminoalkyl-, aryl, heteroaryl, or heterocyclyl $C_1$-$C_6$ alkyl-, substituted with 0-2 $R^{2a}$;
$R^{2a}$ is halo or $C_1$-$C_6$ alkyl;
$R^3$ is H, $C_1$-$C_6$ alkyl, $C_3$-$C_8$ cycloalkyl, hydroxy $C_1$-$C_6$ alkyl or alkoxy $C_1$-$C_6$ alkyl;
$R^4$ is H, $CD_3$, $C_1$-$C_6$ alkyl, alkoxy $C_1$-$C_6$ alkyl, 3- to 10-membered mono or bicyclic cycloalkyl, 4- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-2 $R^{4a}$;
$R^{4a}$ is H, $NR^5R^6$, $C_1$-$C_6$ alkyl, $C_3$-$C_8$ cycloalkyl, hydroxy $C_1$-$C_6$ alkyl or alkoxy $C_1$-$C_6$ alkyl;
$R^5$ and $R^6$ are independently H or $C_1$-$C_4$ alkyl; or
$R^5$ and $R^6$ are taken together with the nitrogen atom to which they are attached to form a 3-10 membered heterocyclyl ring substituted with 0-2 substituents selected from H, $C_1$-$C_4$ alkyl and OH;
or a pharmaceutically acceptable salt, tautomer or stereoisomer thereof.

8. The compound according to claim 4

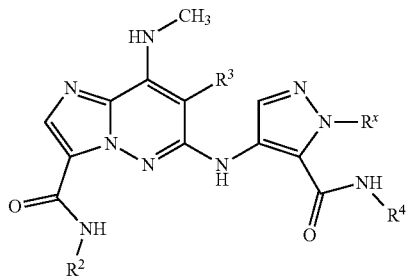

wherein $R^x$ is $C_1$-$C_3$ alkyl;

$R^2$ is H, $C_1$-$C_6$ alkyl, $C_3$-$C_8$ cycloalkyl, hydroxy $C_1$-$C_6$ alkyl, alkoxy $C_1$-$C_6$ alkyl, $C_3$-$C_8$ cycloalkyl $C_1$-$C_6$ alkyl-, di ($C_1$-$C_4$) alkyl aminoalkyl-, aryl, heteroaryl, or heterocyclyl $C_1$-$C_6$ alkyl-, substituted with 0-2 $R^{2a}$;

$R^{2a}$ is halo or $C_1$-$C_6$ alkyl;

$R^3$ is H, $C_1$-$C_6$ alkyl, $C_3$-$C_8$ cycloalkyl, hydroxy $C_1$-$C_6$ alkyl or alkoxy $C_1$-$C_6$ alkyl;

$R^4$ is H, $CD_3$, $C_1$-$C_6$ alkyl, alkoxy $C_1$-$C_6$ alkyl, 3- to 10-membered mono or bicyclic cycloalkyl, 4- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-2 $R^{4a}$;

$R^{4a}$ is H, $NR^5R^6$, $C_1$-$C_6$ alkyl, $C_3$-$C_8$ cycloalkyl, hydroxy $C_1$-$C_6$ alkyl or alkoxy $C_1$-$C_6$ alkyl;

$R^5$ and $R^6$ are independently H or $C_1$-$C_4$ alkyl; or $R^5$ and $R^6$ are taken together with the nitrogen atom to which they are attached to form a 3-10 membered heterocyclyl ring substituted with 0-2 substituents selected from H, $C_1$-$C_4$ alkyl and OH;

or a pharmaceutically acceptable salt, tautomer or stereoisomer thereof.

9. The compound according to claim 4

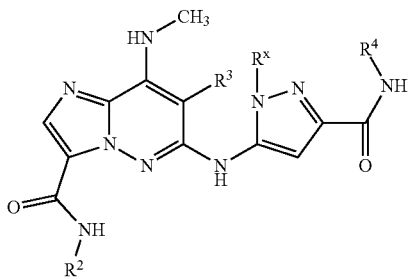

wherein $R^x$ is $C_1$-$C_3$ alkyl;

$R^2$ is H, $C_1$-$C_6$ alkyl, $C_3$-$C_8$ cycloalkyl, hydroxy $C_1$-$C_6$ alkyl, alkoxy $C_1$-$C_6$ alkyl, $C_3$-$C_8$ cycloalkyl $C_1$-$C_6$ alkyl-, di ($C_1$-$C_4$) alkyl aminoalkyl-, aryl, heteroaryl, or heterocyclyl $C_1$-$C_6$ alkyl-, substituted with 0-2 $R^{2a}$;

$R^{2a}$ is halo or $C_1$-$C_6$ alkyl;

$R^3$ is H, $C_1$-$C_6$ alkyl, $C_3$-$C_8$ cycloalkyl, hydroxy $C_1$-$C_6$ alkyl or alkoxy $C_1$-$C_6$ alkyl;

$R^4$ is H, $CD_3$, $C_1$-$C_6$ alkyl, alkoxy $C_1$-$C_6$ alkyl, 3- to 10-membered mono or bicyclic cycloalkyl, 4- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-2 $R^{4a}$;

$R^{4a}$ is H, $NR^5R^6$, $C_1$-$C_6$ alkyl, $C_3$-$C_8$ cycloalkyl, hydroxy $C_1$-$C_6$ alkyl or alkoxy $C_1$-$C_6$ alkyl;

$R^5$ and $R^6$ are independently H or $C_1$-$C_4$ alkyl; or $R^5$ and $R^6$ are taken together with the nitrogen atom to which they are attached to form a 3-10 membered heterocyclyl ring substituted with 0-2 substituents selected from H, $C_1$-$C_4$ alkyl and OH;

or a pharmaceutically acceptable salt, tautomer or stereoisomer thereof.

10. The compound according to claim 4

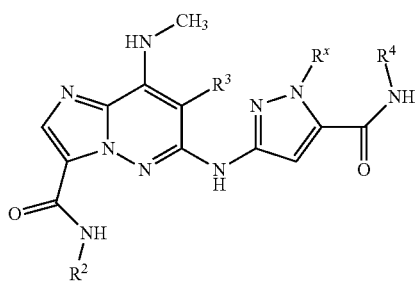

wherein $R^x$ is $C_1$-$C_3$ alkyl;

$R^2$ is H, $C_1$-$C_6$ alkyl, $C_3$-$C_8$ cycloalkyl, hydroxy $C_1$-$C_6$ alkyl, alkoxy $C_1$-$C_6$ alkyl, $C_3$-$C_8$ cycloalkyl $C_1$-$C_6$ alkyl-, di ($C_1$-$C_4$) alkyl aminoalkyl-, aryl, heteroaryl, or heterocyclyl $C_1$-$C_6$ alkyl-, substituted with 0-2 $R^{2a}$;

$R^{2a}$ is halo or $C_1$-$C_6$ alkyl;

$R^3$ is H, $C_1$-$C_6$ alkyl, $C_3$-$C_8$ cycloalkyl, hydroxy $C_1$-$C_6$ alkyl or alkoxy $C_1$-$C_6$ alkyl;

$R^4$ is H, $CD_3$, $C_1$-$C_6$ alkyl, alkoxy $C_1$-$C_6$ alkyl, 3- to 10-membered mono or bicyclic cycloalkyl, 4- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-2 $R^{4a}$;

$R^{4a}$ is H, $NR^5R^6$, $C_1$-$C_6$ alkyl, $C_3$-$C_8$ cycloalkyl, hydroxy $C_1$-$C_6$ alkyl or alkoxy $C_1$-$C_6$ alkyl;

$R^5$ and $R^6$ are independently H or $C_1$-$C_4$ alkyl; or $R^5$ and $R^6$ are taken together with the nitrogen atom to which they are attached to form a 3-10 membered heterocyclyl ring substituted with 0-2 substituents selected from H, $C_1$-$C_4$ alkyl and OH;

or a pharmaceutically acceptable salt, tautomer or stereoisomer thereof.

11. The compound according to claim 4

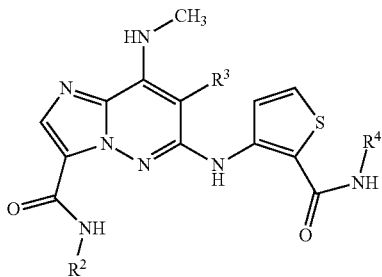

wherein
R$^2$ is H, C$_1$-C$_6$ alkyl, C$_3$-C$_8$ cycloalkyl, hydroxy C$_1$-C$_6$ alkyl, alkoxy C$_1$-C$_6$ alkyl, C$_3$-C$_8$ cycloalkyl C$_1$-C$_6$ alkyl-, di (C$_1$-C$_4$) alkyl aminoalkyl-, aryl, heteroaryl, or heterocyclyl C$_1$-C$_6$ alkyl-, substituted with 0-2 R$^{2a}$;
R$^{2a}$ is halo or C$_1$-C$_6$ alkyl;
R$^3$ is H, C$_1$-C$_6$ alkyl, C$_3$-C$_8$ cycloalkyl, hydroxy C$_1$-C$_6$ alkyl or alkoxy C$_1$-C$_6$ alkyl;
R$^4$ is H, CD$_3$, C$_1$-C$_6$ alkyl, alkoxy C$_1$-C$_6$ alkyl, 3- to 10-membered mono or bicyclic cycloalkyl, 4- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-2 R$^{4a}$;
R$^{4a}$ is H, NR$^5$R$^6$, C$_1$-C$_6$ alkyl, C$_3$-C$_8$ cycloalkyl, hydroxy C$_1$-C$_6$ alkyl or alkoxy C$_1$-C$_6$ alkyl;
R$^5$ and R$^6$ are independently H or C$_1$-C$_4$ alkyl; or
R$^5$ and R$^6$ are taken together with the nitrogen atom to which they are attached to form a 3-10 membered heterocyclyl ring substituted with 0-2 substituents selected from H, C$_1$-C$_4$ alkyl and OH;
or a pharmaceutically acceptable salt, tautomer or stereoisomer thereof.

12. The compound according to claim 4

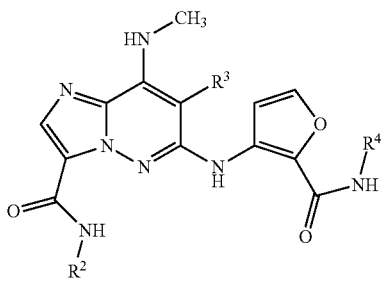

wherein
R$^2$ is H, C$_1$-C$_6$ alkyl, C$_3$-C$_8$ cycloalkyl, hydroxy C$_1$-C$_6$ alkyl, alkoxy C$_1$-C$_6$ alkyl, C$_3$-C$_8$ cycloalkyl C$_1$-C$_6$ alkyl-, di (C$_1$-C$_4$) alkyl aminoalkyl-, aryl, heteroaryl, or heterocyclyl C$_1$-C$_6$ alkyl-, substituted with 0-2 R$^{2a}$;
R$^{2a}$ is halo or C$_1$-C$_6$ alkyl;
R$^3$ is H, C$_1$-C$_6$ alkyl, C$_3$-C$_8$ cycloalkyl, hydroxy C$_1$-C$_6$ alkyl or alkoxy C$_1$-C$_6$ alkyl;
R$^4$ is H, CD$_3$, C$_1$-C$_6$ alkyl, alkoxy C$_1$-C$_6$ alkyl, 3- to 10-membered mono or bicyclic cycloalkyl, 4- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-2 R$^{4a}$;
R$^{4a}$ is H, NR$^5$R$^6$, C$_1$-C$_6$ alkyl, C$_3$-C$_8$ cycloalkyl, hydroxy C$_1$-C$_6$ alkyl or alkoxy C$_1$-C$_6$ alkyl;
R$^5$ and R$^6$ are independently H or C$_1$-C$_4$ alkyl; or
R$^5$ and R$^6$ are taken together with the nitrogen atom to which they are attached to form a 3-10 membered heterocyclyl ring substituted with 0-2 substituents selected from H, C$_1$-C$_4$ alkyl and OH;
or a pharmaceutically acceptable salt, tautomer or stereoisomer thereof.

13. The compound according to claim 4

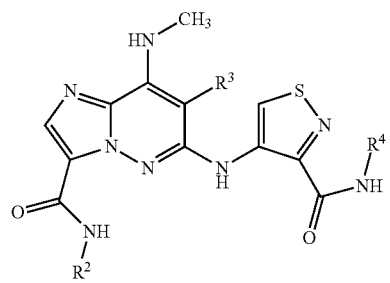

wherein
R$^2$ is H, C$_1$-C$_6$ alkyl, C$_3$-C$_8$ cycloalkyl, hydroxy C$_1$-C$_6$ alkyl, alkoxy C$_1$-C$_6$ alkyl, C$_3$-C$_8$ cycloalkyl C$_1$-C$_6$ alkyl-, di (C$_1$-C$_4$) alkyl aminoalkyl-, aryl, heteroaryl, or heterocyclyl C$_1$-C$_6$ alkyl-, substituted with 0-2 R$^{2a}$;
R$^{2a}$ is halo or C$_1$-C$_6$ alkyl;
R$^3$ is H, C$_1$-C$_6$ alkyl, C$_3$-C$_8$ cycloalkyl, hydroxy C$_1$-C$_6$ alkyl or alkoxy C$_1$-C$_6$ alkyl;
R$^4$ is H, CD$_3$, C$_1$-C$_6$ alkyl, alkoxy C$_1$-C$_6$ alkyl, 3- to 10-membered mono or bicyclic cycloalkyl, 4- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-2 R$^{4a}$;
R$^{4a}$ is H, NR$^5$R$^6$, C$_1$-C$_6$ alkyl, C$_3$-C$_8$ cycloalkyl, hydroxy C$_1$-C$_6$ alkyl or alkoxy C$_1$-C$_6$ alkyl;
R$^5$ and R$^6$ are independently H or C$_1$-C$_4$ alkyl; or
R$^5$ and R$^6$ are taken together with the nitrogen atom to which they are attached to form a 3-10 membered heterocyclyl ring substituted with 0-2 substituents selected from H, C$_1$-C$_4$ alkyl and OH;
or a pharmaceutically acceptable salt, tautomer or stereoisomer thereof.

14. The compound according to claim 4

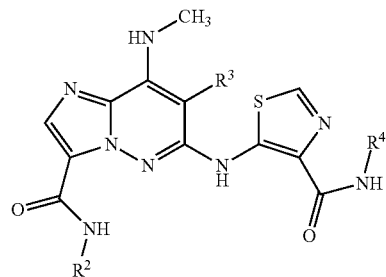

wherein

R$^2$ is H, C$_1$-C$_6$ alkyl, C$_3$-C$_8$ cycloalkyl, hydroxy C$_1$-C$_6$ alkyl, alkoxy C$_1$-C$_6$ alkyl, C$_3$-C$_8$ cycloalkyl C$_1$-C$_6$ alkyl-, di (C$_1$-C$_4$) alkyl aminoalkyl-, aryl, heteroaryl, or heterocyclyl C$_1$-C$_6$ alkyl-, substituted with 0-2 R$^{2a}$;

R$^{2a}$ is halo or C$_1$-C$_6$ alkyl;

R$^3$ is H, C$_1$-C$_6$ alkyl, C$_3$-C$_8$ cycloalkyl, hydroxy C$_1$-C$_6$ alkyl or alkoxy C$_1$-C$_6$ alkyl;

R$^4$ is H, CD$_3$, C$_1$-C$_6$ alkyl, alkoxy C$_1$-C$_6$ alkyl, 3- to 10-membered mono or bicyclic cycloalkyl, 4- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-2 R$^{4a}$;

R$^{4a}$ is H, NR$^5$R$^6$, C$_1$-C$_6$ alkyl, C$_3$-C$_8$ cycloalkyl, hydroxy C$_1$-C$_6$ alkyl or alkoxy C$_1$-C$_6$ alkyl;

R$^5$ and R$^6$ are independently H or C$_1$-C$_4$ alkyl; or

R$^5$ and R$^6$ are taken together with the nitrogen atom to which they are attached to form a 3-10 membered heterocyclyl ring substituted with 0-2 substituents selected from H, C$_1$-C$_4$ alkyl and OH;

or a pharmaceutically acceptable salt, tautomer or stereoisomer thereof.

15. The compound according to claim 4

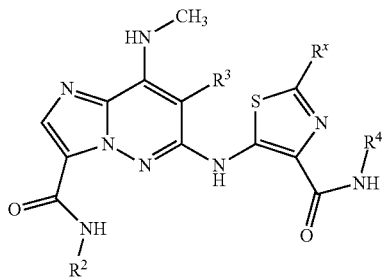

wherein

R$^x$ is C$_1$-C$_3$ alkyl;

R$^2$ is H, C$_1$-C$_6$ alkyl, C$_3$-C$_8$ cycloalkyl, hydroxy C$_1$-C$_6$ alkyl, alkoxy C$_1$-C$_6$ alkyl, C$_3$-C$_8$ cycloalkyl C$_1$-C$_6$ alkyl-, di (C$_1$-C$_4$) alkyl aminoalkyl-, aryl, heteroaryl, or heterocyclyl C$_1$-C$_6$ alkyl-, substituted with 0-2 R$^{2a}$;

R$^{2a}$ is halo or C$_1$-C$_6$ alkyl;

R$^3$ is H, C$_1$-C$_6$ alkyl, C$_3$-C$_8$ cycloalkyl, hydroxy C$_1$-C$_6$ alkyl or alkoxy C$_1$-C$_6$ alkyl;

R$^4$ is H, CD$_3$, C$_1$-C$_6$ alkyl, alkoxy C$_1$-C$_6$ alkyl, 3- to 10-membered mono or bicyclic cycloalkyl, 4- to 10-membered mono or bicyclic aryl, 4- to 10-membered mono or bicyclic heterocyclyl, or substituted 4- to 10-mono or bicyclic heteroaryl, each heterocyclyl or heteroaryl containing 1-3 heteroatoms selected from N, O, and S, any of said groups other than H substituted with 0-2 R$^{4a}$;

R$^{4a}$ is H, NR$^5$R$^6$, C$_1$-C$_6$ alkyl, C$_3$-C$_8$ cycloalkyl, hydroxy C$_1$-C$_6$ alkyl or alkoxy C$_1$-C$_6$ alkyl;

R$^5$ and R$^6$ are independently H or C$_1$-C$_4$ alkyl; or

R$^5$ and R$^6$ are taken together with the nitrogen atom to which they are attached to form a 3-10 membered heterocyclyl ring substituted with 0-2 substituents selected from H, C$_1$-C$_4$ alkyl and OH;

or a pharmaceutically acceptable salt, tautomer or stereoisomer thereof.

16. A pharmaceutical composition comprising one or more compounds according to claim 1 and a pharmaceutically acceptable carrier or diluent.

\* \* \* \* \*